(12) United States Patent
Mackay et al.

(10) Patent No.: US 10,585,094 B2
(45) Date of Patent: Mar. 10, 2020

(54) DEVICES AND METHODS FOR NANOPARTICLE ENHANCED IMPEDANCE-BASED MOLECULAR SENSING

(71) Applicant: The Governors of the University of Alberta, Edmonton (CA)

(72) Inventors: Scott Mackay, Edmonton (CA); Jie Chen, Edmonton (CA); Peter Hermansen, Edmonton (CA); David Scott Wishart, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 15/694,286

(22) Filed: Sep. 1, 2017

(65) Prior Publication Data

US 2018/0059101 A1    Mar. 1, 2018

Related U.S. Application Data

(60) Provisional application No. 62/382,534, filed on Sep. 1, 2016.

(51) Int. Cl.
*G01N 33/543* (2006.01)
*G01N 27/22* (2006.01)

(52) U.S. Cl.
CPC ....... *G01N 33/5438* (2013.01); *G01N 27/226* (2013.01)

(58) Field of Classification Search
CPC .......................... G01N 33/5438; G01N 27/226
See application file for complete search history.

(56) References Cited

U.S. PATENT DOCUMENTS

| | | | |
|---|---|---|---|
| 6,683,446 B1 * | 1/2004 | Pope | B01J 19/0046 205/81 |
| 2004/0014106 A1 * | 1/2004 | Patno | C12Q 1/68 435/6.12 |

(Continued)

OTHER PUBLICATIONS

Abdelrasoul et al., "Nanocomposite Scaffold Fabrication by Incorporating Gold Nanoparticles Into Biodegradable Polymer Matrix: Synthesis, Characterization, and Photothermal Effect," Materials Science and Engineering: C, Nov. 2015, vol. 56, pp. 305-310.

(Continued)

*Primary Examiner* — Melanie Brown
(74) *Attorney, Agent, or Firm* — Evan Law Group LLC

(57) ABSTRACT

An impedance based biosensor and method for detecting a target biomolecule in a sample are provided. The biosensor has a substrate, and first and second spaced-apart electrodes disposed at the substrate. A molecular recognition element (MRE) for binding with the target is bound to the substrate between the first and second electrodes. The biosensor also has a nanoparticle having an MRE bound to its surface. In the presence of the target, the nanoparticle is immobilized between the first and second electrodes due to binding of the target biomolecule with the first MRE and binding of the target biomolecule with the second MRE. A measurable change in electrical impedance across the first and second electrodes occurs due to the immobilization of the nanoparticle between the first and second electrodes.

20 Claims, 45 Drawing Sheets

(56) References Cited

U.S. PATENT DOCUMENTS

| | | | | |
|---|---|---|---|---|
| 2005/0059105 A1* | 3/2005 | Alocilja | ............. | G01N 33/5438 435/7.32 |
| 2005/0227373 A1* | 10/2005 | Flandre | ................ | G01N 27/221 436/518 |
| 2006/0148104 A1* | 7/2006 | Marini | ..................... | B82Y 5/00 436/524 |
| 2007/0076214 A1* | 4/2007 | Rothberg | ................ | C40B 60/12 356/491 |
| 2011/0189705 A1* | 8/2011 | Gao | ................. | G01N 33/54306 435/7.92 |
| 2013/0264221 A1* | 10/2013 | Kim | .................. | G01N 27/3278 205/778 |
| 2014/0332407 A1* | 11/2014 | Mai | .................... | G01N 27/3276 205/777.5 |
| 2015/0082920 A1* | 3/2015 | Haick | .................... | B82Y 15/00 73/865.8 |

OTHER PUBLICATIONS

Arlett et al., "Comparative Advantages of Mechanical Biosensors," Nature Nanotechnology, Nature Publishing Group, Apr. 2011, vol. 6 (4), pp. 203-215.
Bain et al., "Formation of Monolayers by the Coadsorption of Thiols on Gold: Variation in the Head Group, Tail Group, and Solvent," Journal of the American Chemical Society, Aug. 1989, vol. 111 (18), pp. 7155-7164.
Baptista et al., "Gold Nanoparticles for the Development of Clinical Diagnosis Methods," Analytical and Bioanalytical Chemistry, Jun. 2008, vol. 391 (3), pp. 943-950.
Cary et al., "Biomarkers in Prostate Cancer Surveillance and Screening: Past, Present, and Future," Therapeutic Advances in Urology, Dec. 2013, vol. 5 (6), pp. 318-329.
Cecchet et al., "Redox Mediation at 11-Mercaptoundecanoic Acid Self-Assembled Monolayers on Gold," The Journal of Physical Chemistry B, Feb. 2006, vol. 110 (5), pp. 2241-2248.
Chen et al., "Electrical Nanogap Devices for Biosensing," Materials Today, Nov. 2010, vol. 13 (11), pp. 28-41.
Chen et al., "Quantized Capacitance Charging of Monolayer-Protected Au Clusters," Journal of Physical Chemistry B, Oct. 1998, vol. 102 (49), pp. 9898-9907.
Crumbliss et al., "Colloidal Gold as a Biocompatible Immobilization Matrix Suitable for the Fabrication of Enzyme Electrodes by Electrodeposition," Biotechnology and Bioengineering, Aug. 1992, vol. 40 (4), pp. 483-490.
Delong et al., "Functionalized Gold Nanoparticles for the Binding, Stabilization, and Delivery of Therapeutic DNA, RNA, and Other Biological Macromolecules," Nanotechnology, Science and Applications, Sep. 2010, vol. 3, pp. 53-63.
Dwyer et al., "Periplasmic Binding Proteins: A Versatile Superfamily for Protein Engineering," Current Opinion in Structural Biology, Aug. 2004, vol. 14 (4), pp. 495-504.
Elghanian et al., "Selective Colorimetric Detection of Polynucleotides Based on the Distance-Dependent Optical Properties of Gold Nanoparticles," Science, Aug. 1997, vol. 277 (5329), pp. 1078-1081.
Etzioni et al., "The Case for Early Detection," Nature Reviews Cancer, Apr. 2003, vol. 3 (4), pp. 243-252.
Ghosh et al., "Interparticle Coupling Effect on the Surface Plasmon Resonance of Gold Nanoparticles: From Theory to Applications," Chemical Reviews, Nov. 2007, vol. 107 (11), pp. 4797-4854.
Golub et al., "γ-APTES Modified Silica Gels: The Structure of the Surface Layer," Journal of Colloid and Interface Science, May 1996, vol. 179 (2), pp. 482-487.
Grieshaber et al., "Electrochemical Biosensors—Sensor Principles and Architectures," Sensors, Mar. 2008, vol. 8 (3), pp. 1400-1458.
Hermansen et al., "Simulations and Design of Microfabricated Interdigitated Electrodes for Use in a Gold Nanoparticle Enhanced Biosensor," 38th Annual International Conference of the IEEE Engineering in Medicine and Biology Society (EMBC), Aug. 2016, pp. 299-302.
Huang et al., "Aptamer-Modified Gold Nanoparticles for Colorimetric Determination of Platelet-Derived Growth Factors and Their Receptors," Analytical Chemistry, Sep. 2005, vol. 77 (17), pp. 5735-5741.
Jordan et al., "Surface Plasmon Resonance Imaging Measurements of DNA Hybridization Adsorption and Streptavidin/DNA Multilayer Formation at Chemically Modified Gold Surfaces," Analytical Chemistry, Dec. 1997, vol. 69 (24), pp. 4939-4947.
Kim et al., "Kinetics of Gold Nanoparticle Aggregation: Experiments and Modeling," Journal of Colloid and Interface Science, Feb. 2008, vol. 318 (2), pp. 238-243.
Kim et al., "Polymeric Self-Assembled Monolayers. 5. Synthesis and Characterization of ω-Functionalized, Self-Assembled Diacetylenic and Polydiacetylenic Monolayers," Langmuir, Dec. 1996, vol. 12 (25), pp. 6065-6073.
Kimling et al., "Turkevich Method for Gold Nanoparticle Synthesis Revisited," Journal of Physical Chemistry B, Jul. 2006, vol. 110 (32), pp. 15700-15707.
Lauks., "Microfabricated Biosensors and Microanalytical Systems for Blood Analysis," Accounts of Chemical Research, Apr. 1998, vol. 31 (5), pp. 317-324.
Lee et al., "A DNA-Gold Nanoparticle-based Colorimetric Competition Assay for the Detection of Cysteine," Nano Letters, Feb. 2008, vol. 8 (2), pp. 529-533.
Lee et al., "Chip-Based Scanometric Detection of Mercuric Ion Using DNA-Functionalized Gold Nanoparticles," Analytical Chemistry, Sep. 2008, vol. 80 (17), pp. 6805-6808.
Li et al., "Colorimetric Detection of Dna Sequences Based on Electrostatic Interactions With Unmodified Gold Nanoparticles," Proceedings of the National Academy of Sciences of the United States of America, Sep. 2004, vol. 101 (39), pp. 14036-14039.
Lin et al., "A Regenerating Ultrasensitive Electrochemical Impedance Immunosensor for the Detection of Adenovirus," Biosensors & Bioelectronics, Jun. 2015, vol. 68, pp. 129-134.
Love et al., "Self-Assembled Monolayers of Thiolates on Metals as a Form of Nanotechnology," Chemical Reviews, Apr. 2005, vol. 105 (4), pp. 1103-1169.
Mackay et al., "Using Impedance Measurements to Characterize Surface Modified with Gold Nanoparticles," Sensors, Sep. 2017, vol. 17 (9), 11 pages.
Mackay et al., "Developing Trends in Aptamer-Based Biosensor Devices and Their Applications," IEEE Transactions on Biomedical Circuits and Systems, Feb. 2014, vol. 8 (1), pp. 4-14.
Mackay et al., "Simulations of Interdigitated Electrode Interactions with Gold Nanoparticles for Impedance-Based Biosensing Applications," Sensors, Sep. 2015, vol. 15 (9), pp. 22192-22208.
Mackay et al., "Live Demonstration: Portable Impedance-Based Biosensor System for Metabolomic Sensing," IEEE Biomedical Circuits and Systems Conference (BioCAS), 2016, 1 page.
Mascini et al., "Biosensors for Biomarkers in Medical Diagnostics," Biomarkers, Nov. 2008, vol. 13 (7), pp. 637-657.
Mehta et al., "Optical Bio Sensor Using Graphene Nano Ribbons," Semiconductor Device Research Symposium (ISDRS), Dec. 2011.
Motesharei et al., "A Porous Silicon-Based Optical Interferometric Biosensor," Science, Oct. 1997, vol. 278 (5339), pp. 840-843.
Moulin et al., "Microcantilever-Based Biosensors," Ultramicroscopy, Feb. 2000, vol. 82 (1-4), pp. 23-31.
Porter et al., "Spontaneously Organized Molecular Assemblies. 4. Structural Characterization of n-alkyl Thiol Monolayers on Gold by Optical Ellipsometry, Infrared Spetcroscopy, and Electrochemistry," Journal of the American Chemical Society, Jun. 1987, vol. 109 (12), pp. 3559-3568.
Radke et al., "A Microfabricated Biosensor for Detecting Foodborne Bioterrorism Agents," IEEE Sensors Journal, Aug. 2005, vol. 5 (4), pp. 744-750.
Raiteri et al., "Micromechanical Cantilever-Based Biosensors," Sensors and Actuators B: Chemical, Oct. 2001, vol. 79 (2-3), pp. 115-126.

(56) References Cited

OTHER PUBLICATIONS

Rodriguez et al., "Aptamer Biosensor for Label-Free Impedance Spectroscopy Detection of Proteins Based on Recognition-Induced Switching of the Surface Charge," Chemical Communications, Sep. 2005, pp. 4267-4269.
Salata., "Applications of Nanoparticles in Biology and Medicine," Journal of Nanobiotechnology, Apr. 2004, vol. 6, pp. 1-6.
Schmidt et al., "Photoinitiated Polymerization of Styrene from Self-Assembled Monolayers on Gold," Langmuir, Jan. 2002, vol. 18 (4), pp. 1281-1287.
Shukla et al., "Biocompatibility of Gold Nanoparticles and Their Endocytotic Fate Inside the Cellular Compartment: A Microscopic Overview," Langmuir, Nov. 2005, vol. 21 (23), pp. 10644-10654.
Song et al., "Immobilization of DNA on 11-mercaptoundecanoic Acid-modified Gold (111) Surface for Atomic Force Microscopy Imaging," Microscopy Research and Technique, Oct. 2005, vol. 68 (2), pp. 59-64.
Su et al., "Microcantilever Resonance-Based DNA Detection With Nanoparticle Probes," Applied Physics Letters, May 2003, vol. 82 (20), pp. 3562-3564.
Thewes et al., "Sensor Arrays for Fully-Electronic DNA Detection on CMOS," IEEE International Solid-State Circuits Conference, Feb. 2002, 3 pages.
Turkevich et al., "A Study of the Nucleation and Growth Processes in the Synthesis of Colloidal Gold," Discussions of the Faraday Society, 1949, vol. 11, pp. 55-75.
Van Gerwen et al., "Nanoscaled Interdigitated Electrode Arrays for Biochemical Sensors," Sensors and Actuators B: Chemical, Jun. 1998, vol. 49 (1-2), pp. 73-80.
Yu et al., "An Impedance Detection Circuit for Applications in a Portable Biosensor System," IEEE International Symposium on Circuits and Systems (ISCAS), 2016, 4 pages.
Zamborini et al., "Corrosion Passivation of Gold by n-Alkanethiol Self-Assembled Monolayers: Effect of Chain Length and End Group," Langmuir, May 1998, vol. 14 (12), pp. 3279-3286.
Zhao et al., "Simple and Rapid Colorimetric Biosensors Based on DNA Aptamer and Noncrosslinking Gold Nanoparticle Aggregation," ChemBioChem, May 2007, vol. 8 (7), pp. 727-731.

* cited by examiner

FIG. 19
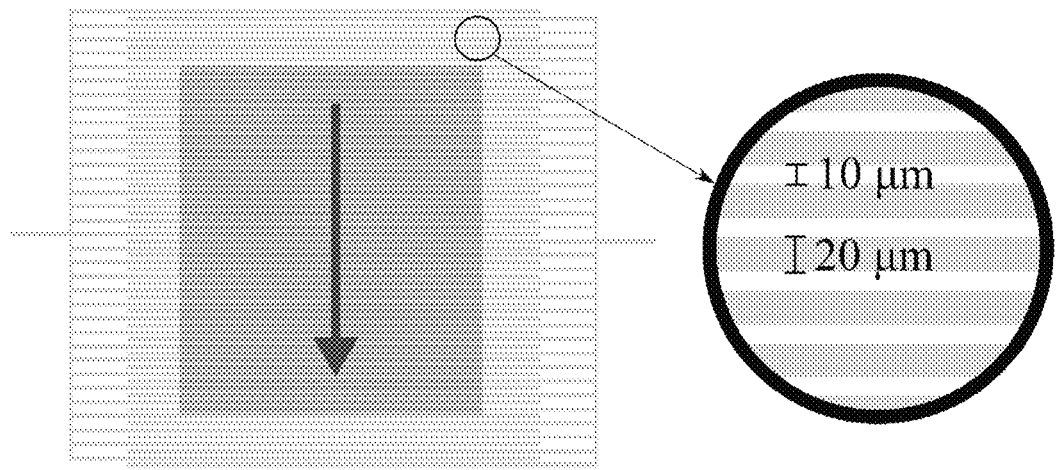
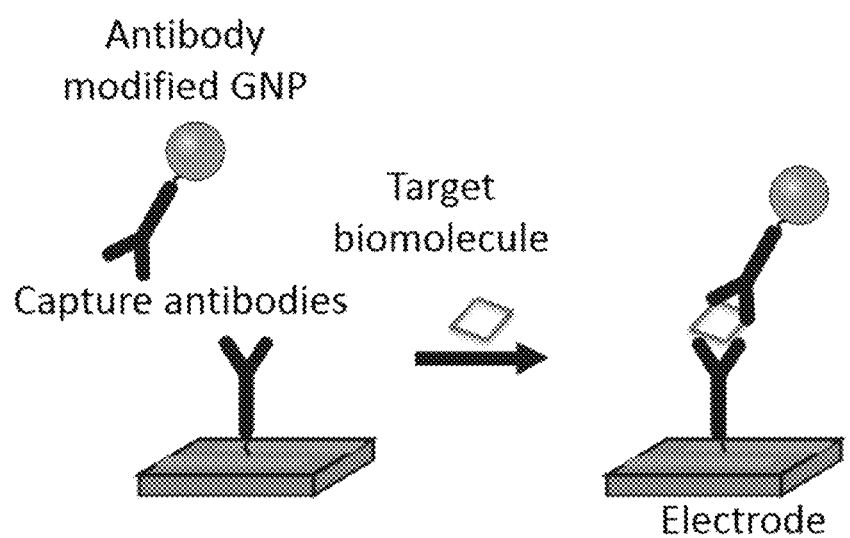
FIG. 20

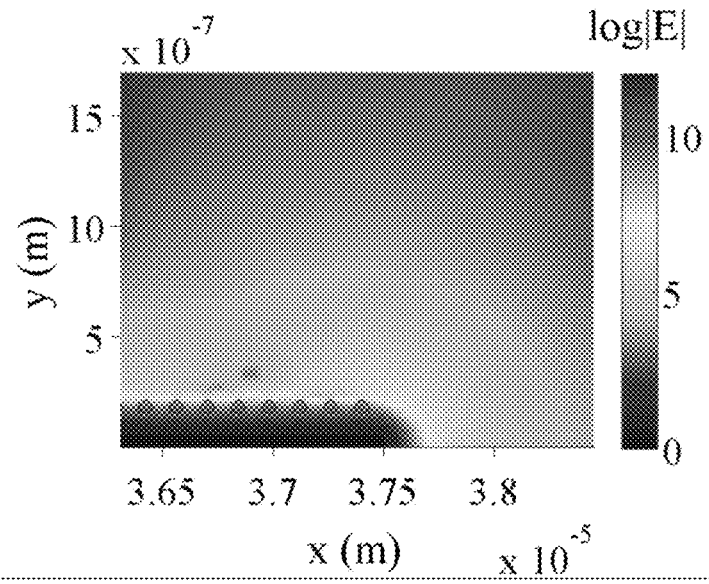
FIG. 29-A
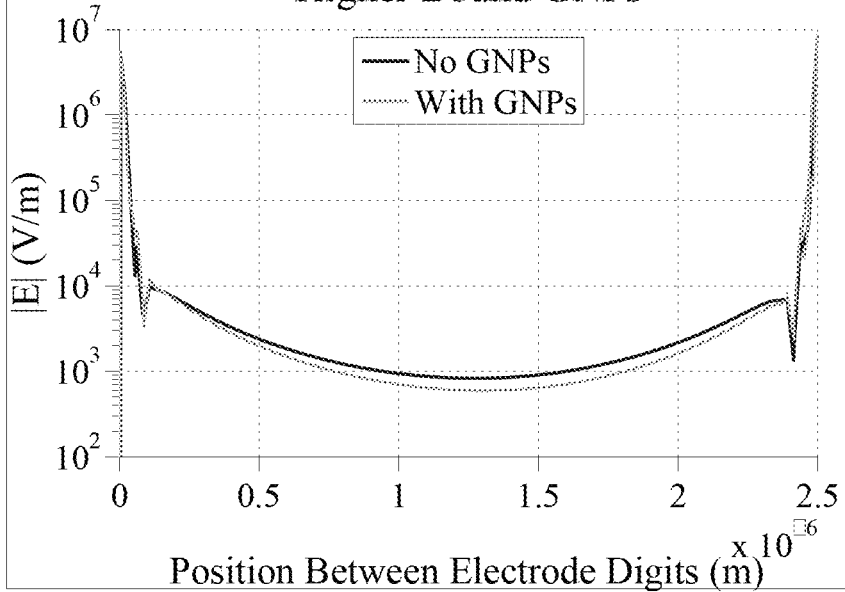
FIG. 29-B

FIG. 32
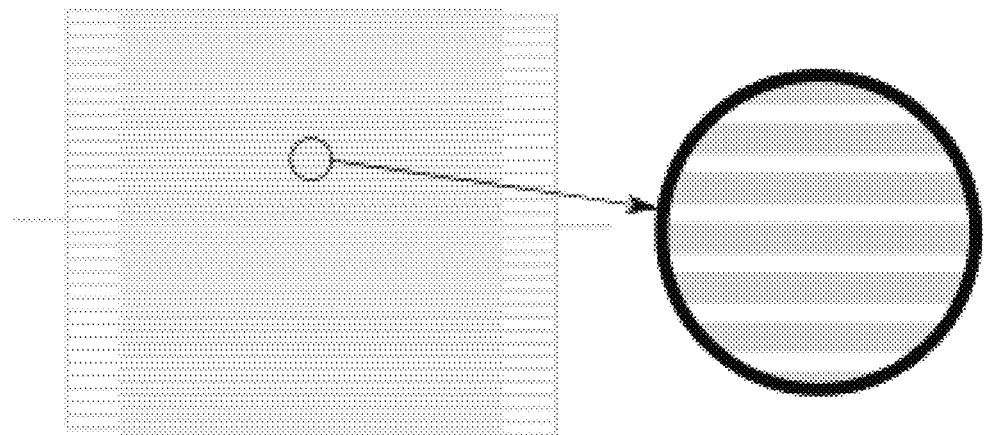
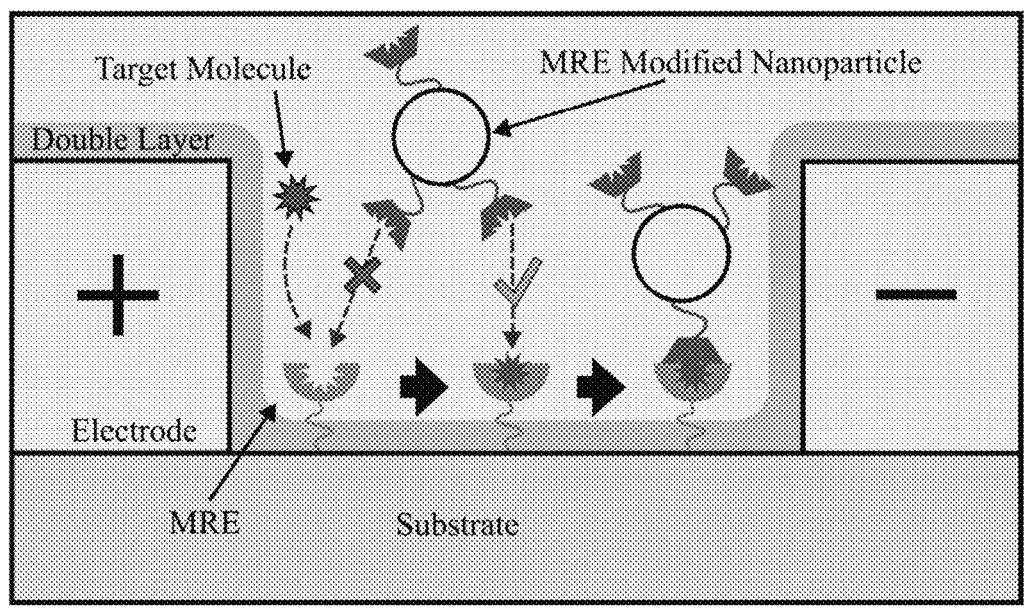
FIG. 33

FIG. 34
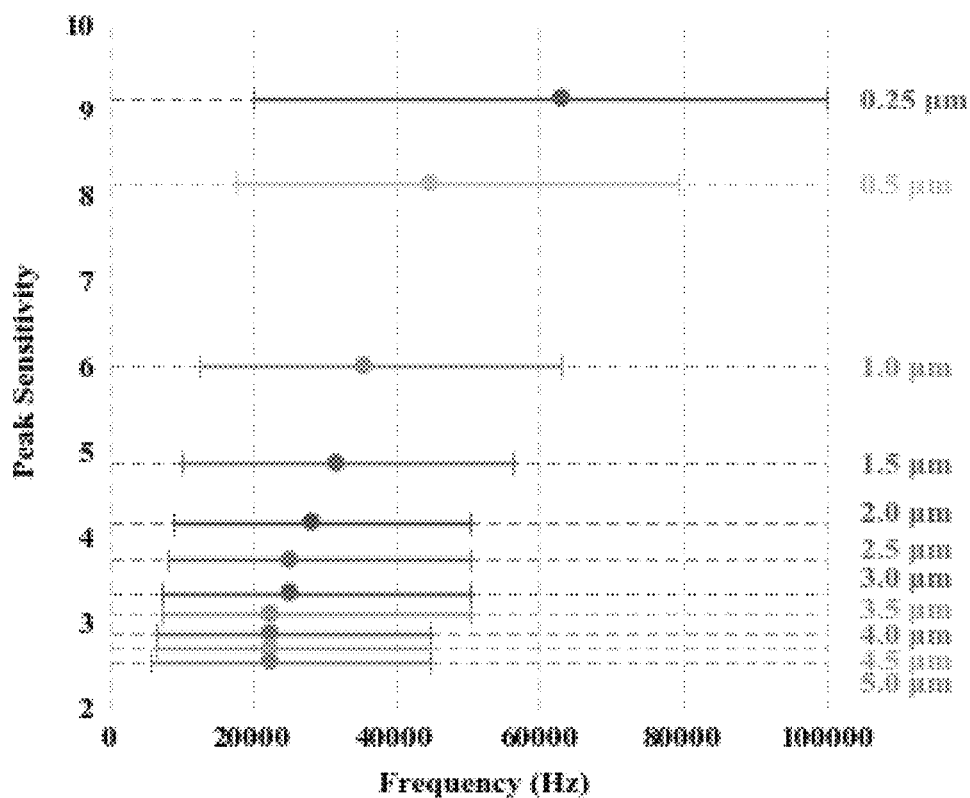
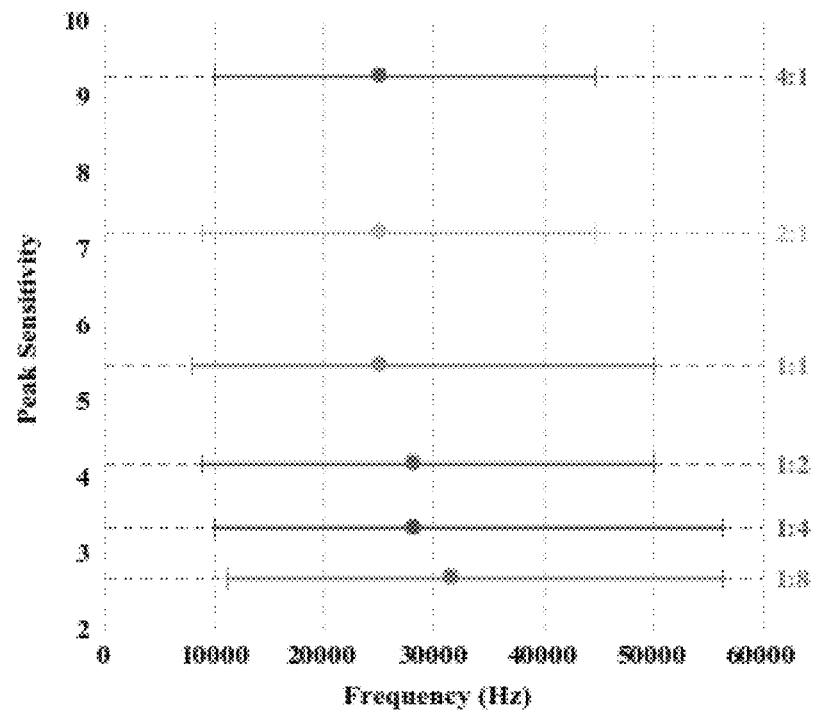
FIG. 35

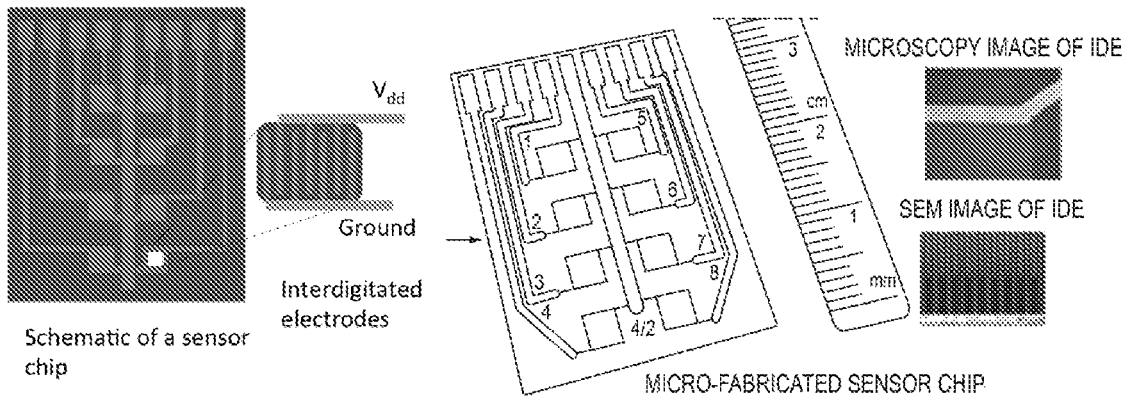
FIG. 50C  FIG. 50D
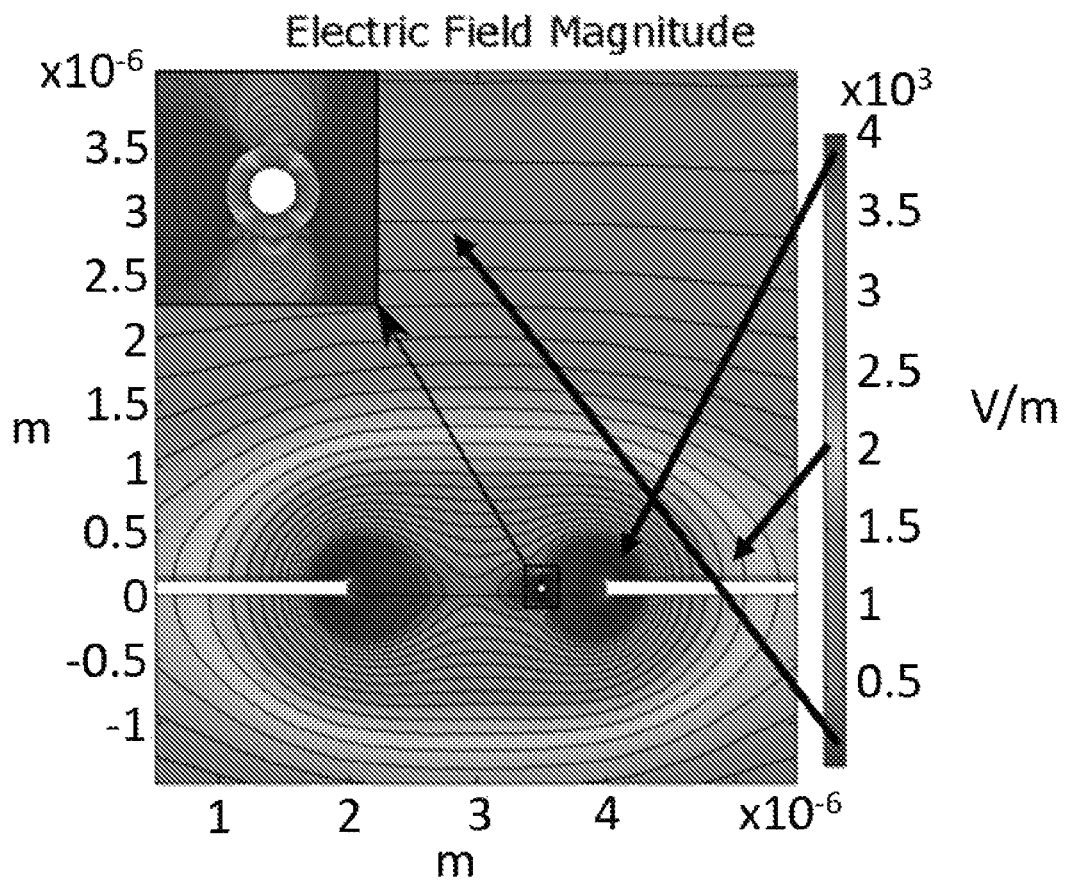
FIG. 50E

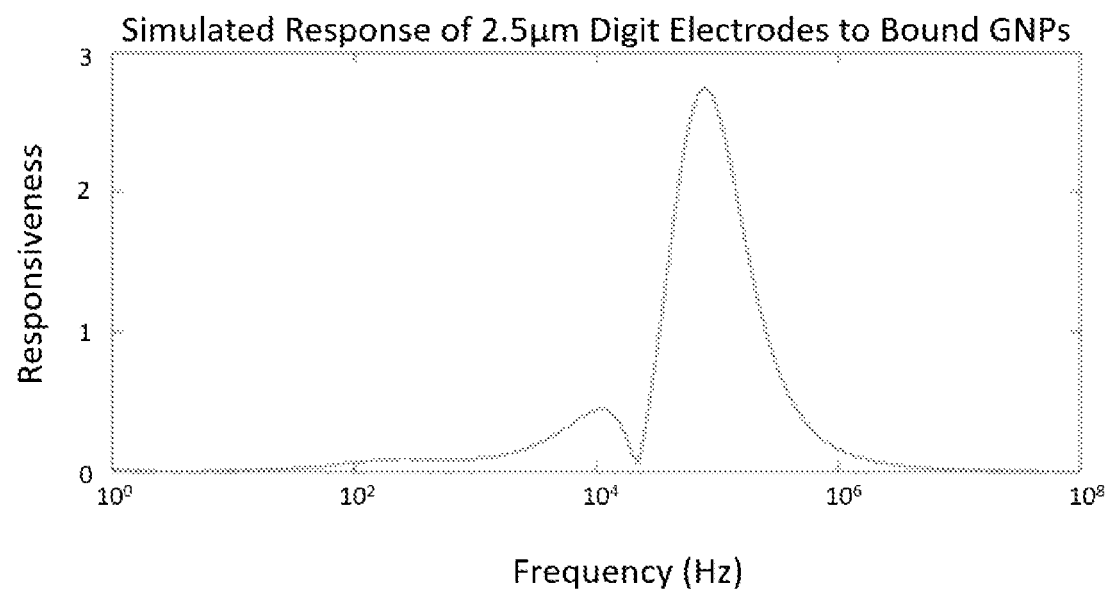
FIG.50F
FIG. 51A
(a)
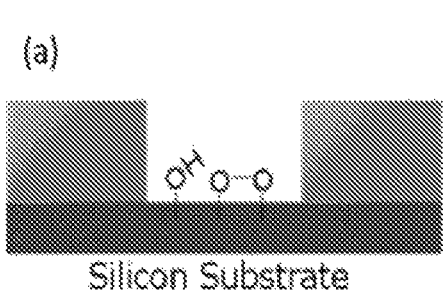
(b)
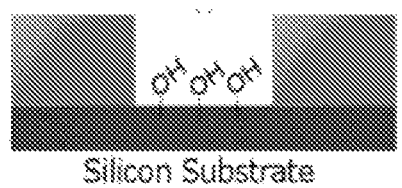
FIG. 51B
FIG. 51C
(c)
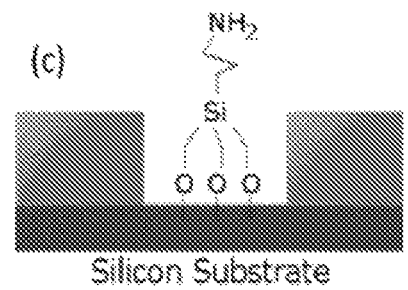
(d)
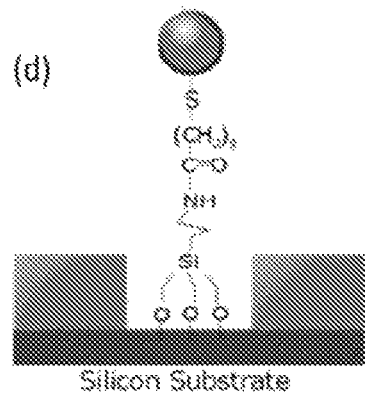
FIG. 51D

(e)

(f)

(d)

DEVICES AND METHODS FOR NANOPARTICLE ENHANCED IMPEDANCE-BASED MOLECULAR SENSING

CROSS REFERENCE TO RELATED APPLICATIONS

This application claims the benefit of priority of U.S. Provisional Patent Application No. 62/382,534 filed on Sep. 1, 2016, which is incorporated herein by reference.

FIELD

The present disclosure relates to molecular sensing, and more particularly to nanoparticle enhanced impedance-based molecular sensing.

BACKGROUND

With the increased practice of preventative healthcare to help reduce costs worldwide, sensor technology improvement is vital to patient care. Point-of-care diagnostics can reduce time and lower labor in testing, and also can effectively avoid transporting costs because of portable designs.

Microfabrication and nanotechnology allows for interfacing fabricated components directly with biological and chemical elements in new ways, creating opportunities for new devices. One example of this is biosensor devices. In the most general sense, a biosensor is a device that can detect, measure and/or report the presence of specific components in biological samples. An example of a biosensor is a glucose sensor used by people to monitor and control diabetes. By detecting different biological components, biosensors can be used for numerous applications in healthcare and diagnostics. The ability to test for a specific biomarker can help stop diseases such as cancer while they are still localized. This makes them easier and cheaper to cure. While there are technologies in existence that can perform such tasks, they often require samples to be tested at a laboratory dedicated to this purpose. Both transporting and testing the sample can be expensive and time-consuming, making a point-of-care design ideal in terms of time and money.

Many of these devices can take advantage of microfabricated components to allow for accurate and sensitive detection of components in biological samples. One example of these includes microfabricated electrodes, which can be used for electrical detection of biomolecules. Though designs of biosensor electrodes can vary, a common design uses interdigitated electrodes (IDEs)

Various bio-sensing techniques have been proposed using optical, electrical, and mechanical detection methods. Although individual methods can vary, electrical and electrochemical biosensors work by measuring changes in electrical properties caused by the presence of specific biological targets. These changes may be caused by interference in electric fields, chemical reactions, or from conductive labels. Electrodes are used as interfaces both in applying electric fields to the tested samples and as a method of transmitting and measuring electrical detection signals. The types of measured electrical signal vary as well depending on the application, and may be simple impedance or resistance measurements, capacitance measurements, or electrical spectroscopy, taking measurements over a range of frequencies.

Compared to optical methods of detection, impedance tests are easier to use and more versatile. The equipment often required for optical detection is too large, complex, and expensive for portable point-of-care testing. However, optical methods tend to achieve high sensitivity, which is why they are commonly used. Mechanical methods, on the other hand, can yield specific and sensitive results, but they are much more prone to inaccuracies due to temperature and pH changes.

Impedance based detection methods have been shown to have a lower maximum sensitivity than other techniques. In addition, some techniques that use interdigitated electrodes to detect a target employ a broad frequency range impedance spectroscopy to detect the target. The results of the impedance spectroscopy are often fitted to a model of the interdigitated electrode/nanoparticle system. The broad frequency range impedance spectroscopy and/or model fitting typically require appropriate electronics or other computer related components, which add to the size and expense of the systems.

Accordingly, improvements in impedance based detection methods and devices are desired.

The above information is presented as background information only to assist with an understanding of the present disclosure. No assertion or admission is made as to whether any of the above might be applicable as prior art with regard to the present disclosure.

SUMMARY

According to an aspect, the present disclosure is directed to a biosensor configured to detect a target biomolecule in a sample, the biosensor comprising a detection device comprising a substrate, and first and second spaced-apart electrodes disposed at the substrate; a first molecular recognition element (MRE) bound to the substrate between the first and second electrodes, the MRE being adapted to bind with the target biomolecule; and a nanoparticle having a second MRE bound to its surface, wherein an electrical impedance across the first and second electrodes changes in response to an immobilization of the nanoparticle between the first and second electrodes due to binding of the target biomolecule with the first MRE and binding of the target biomolecule with the second MRE.

In an embodiment, the first and second electrodes form part of an interdigitated microelectrode array such that the first electrode is formed into an array of first digits and the second electrode is formed into an array of second digits interdigitated with the array of first digits, and wherein the first MRE is bound to the substrate between adjacent digits of the first and second electrodes.

In an embodiment, the change in impedance is caused at least in part by a double layer capacitance formed in a solution surrounding the nanoparticle.

In an embodiment, the nanoparticle is a gold nanoparticle.

In an embodiment, the nanoparticle is coated with mercaptoundecanoic acid (MUA).

In an embodiment, the first and second MREs are one of an aptamer, an antibody, a binding protein, an RNA fragment, or a DNA fragment.

In an embodiment, the detection device is configured for measuring the impedance across the first and second electrodes at one or more frequencies in the range of 50 kHz to 500 kHz.

In an embodiment, the biosensor further comprises an electronic display device communicatively coupled to the detection device, the display device configured to display information that is responsive to changes in the electrical impedance across the first and second electrodes.

In an embodiment, the biosensor is configured to detect a change in the electrical impedance across the first and second electrodes using impedance spectroscopy.

In an embodiment, the detection device is configured for measuring the impedance across the first and second electrodes at one or more frequencies, and wherein the biosensor is configured to determine the presence or absence of the target biomolecule in the sample based on the one or more impedance measurements.

In an embodiment, the first and second electrodes comprise at least one of gold or aluminum.

In an embodiment, the first and second electrodes are modified with a pacifying self-assembled monolayer.

In an embodiment, the surface of the substrate has been modified using 3-Aminopropyltriethoxy silane (APTES) to activate the substrate towards selective chemical binding with the MRE.

In an embodiment, the biosensor comprises a plurality of first MREs bound to the substrate between the first and second electrodes, and a plurality of nanoparticles each having at least one second MRE bound to its surface, wherein the electrical impedance across the first and second electrodes changes in response to the immobilization of at least two of the nanoparticles between the first and second electrodes.

According to an aspect, the present disclosure is directed to a method of detecting a target biomolecule in a sample, comprising providing a detection device comprising a substrate, and first and second spaced-apart electrodes disposed at the substrate; exposing the sample to a first molecular recognition element (MRE) and to a nanoparticle having a second MRE bound to its surface, where the first MRE is bound to the substrate between the first and second electrodes, the first and second MREs being adapted to bind with the target biomolecule; measuring the electrical impedance across the first and second electrodes; and determining the presence or absence of the target biomolecule in the sample based on the measured electrical impedance, where the electrical impedance across the first and second electrodes changes in response to an immobilization of the nanoparticle between the first and second electrodes due to binding of the target biomolecule with the first MRE and binding of the target biomolecule with the second MRE.

In an embodiment, the change in impedance is caused at least in part by a double layer capacitance formed in a solution surrounding the nanoparticle.

In an embodiment, the nanoparticle is a gold nanoparticle.

In an embodiment, the method further comprises measuring the impedance across the first and second electrodes at one or more frequencies in the range of 50 kHz to 500 kHz.

In an embodiment, the method further comprises displaying on an electronic display device information that is responsive to changes in the electrical impedance across the first and second electrodes.

According to an aspect, the present disclosure is directed to a method of manufacturing a biosensor for detecting a target biomolecule in a sample, comprising selecting a molecular recognition element (MRE) based on its binding affinity for the target biomolecule; providing a detection device comprising a substrate, and first and second spaced-apart electrodes disposed at the substrate; and providing a first molecular recognition element (MRE) bound to the substrate between the first and second electrodes, the MRE being adapted to bind with the target biomolecule; providing a nanoparticle having a second MRE bound to its surface, wherein the electrical impedance across the first and second electrodes is configured to change in response to an immobilization of the nanoparticle between the first and second electrodes due to binding of the target biomolecule with the first MRE and binding of the target biomolecule with the second MRE.

The foregoing summary provides some aspects and features according to the present disclosure but is not intended to be limiting. Other aspects and features of the present disclosure will become apparent to those ordinarily skilled in the art upon review of the following description of specific embodiments in conjunction with the accompanying figures. Accordingly, the drawings and detailed description are to be regarded as illustrative in nature and not restrictive.

BRIEF DESCRIPTION OF THE DRAWINGS

Embodiments of the present disclosure will now be described, by way of example only, with reference to the attached Figures.

FIG. 19 is an example of a gold IDE structure.

FIG. 20 is an example of the mechanism used for biomolecule detection.

FIG. 21-B is a plot of the electric potential of IDEs (5 μm digit width and 2.5 μm spacing) with 0.1 V DC applied with a background KCl concentration of 150 μM take at t=15 micro-seconds.

FIG. 21-C is a plot of the electric potential of IDEs (5 μm digit width and 2.5 μm spacing) with 0.1 V DC applied with a background KCl concentration of 150 μM take at t=30 micro-seconds.

FIG. 21-D is a plot of the electric potential of IDEs (5 μm digit width and 2.5 μm spacing) with 0.1 V DC applied with a background KCl concentration of 150 μM take at t=45 micro-seconds.

FIG. 22-B is a plot of the electric field magnitude between two of the 20 μm digits with 10 μm spacing.

FIG. 22-C is a logarithmic plot of the electric field magnitude for 10 μm digits with 5 μm spacing.

FIG. 22-D is a plot of the electric field magnitude between two of the 10 μm digits with 5 μm spacing.

FIG. 22-E is a logarithmic plot of the electric field magnitude for 5 μm digits with 2.5 μm spacing.

FIG. 22-F is a plot of the electric field magnitude between two of the 5 μm digits with 2.5 μm spacing.

FIG. 26-B is a graph comparing the simulated electric field magnitude directly between two digits of electrodes with and without bound gold nanoparticles with a KCl concentration of 0.15 mM in the solution in the electrodes.

FIG. 26-C is a graph comparing the simulated electric field magnitude directly between two digits of electrodes with and without bound gold nanoparticles with a KCl concentration of 1 mM in the solution in the electrodes.

FIG. 26-D is a graph comparing the simulated electric field magnitude directly between two digits of electrodes with and without bound gold nanoparticles with a KCl concentration of 10 mM in the solution in the electrodes.

FIG. 27-B is a graph comparing the simulated electric field magnitude directly between two of the 20 μm digits with 10 μm gaps; with and without bound gold nanoparticles and a KCl concentration of 10 mM in the solution in the electrodes.

FIG. 29-A is a logarithmic electric field magnitude of 5 μm digit and 2.5 μm gap electrodes with 0.1 V applied, 10 mM KCl concentration and 60 nm GNPs bound 150 nm above the electrodes.

FIG. 29-B is a graph of the electric field magnitude directly between the 2.5 μm gap, with and without gold nanoparticles.

FIG. 32 is an example of the basic structure of an interdigitated electrode.

FIG. 33 demonstrates the detection mechanism of the biosensor system.

FIG. 34 is a plot of peak sensitivity values and cutoff frequencies for different gap sizes with electrodes kept at a 1:2 gap-to-digit ratio.

FIG. 35 is a plot of peak sensitivity values and cutoff frequencies for different gap sizes with electrodes kept at a 2 μm gap size.

FIG. 50-B is an illustration of how the MUA creates a layer over the gold IDEs.

FIG. 50-C is a schematic of the impedance-based sensor chip design.

FIG. 50-D is an image of the impedance-based sensor chip design.

FIG. 50-E is a plot of electric field magnitude from a COMSOL simulations of IDEs with bound gold nanoparticles.

FIG. 50-F is a graph showing the impedance magnitude sensitivity of IDEs to GNPs bound to different positions between electrode digits as a function of frequency FIG. 51-A is a diagram of Silicon IDE chip after microfabrication. Silicon dioxide substrate has reacted with oxygen in the air.

FIG. 51-C is a diagram of Silicon IDE chip after microfabrication. Hydroxy groups are used as binding sites for the APTES, which have a free amine group.

FIG. 51-D is a diagram of Silicon IDE chip after microfabrication. GNPs are bound to the APTES using EDC/NHS chemistry.

FIG. 51-E is a histogram of the GNPs size distribution.

FIG. 51-F is a plot of UV-Vis absorption spectra of the GNPs before and after MUA surface coating.

FIG. 52-B is a graph of the percent difference between the impedance magnitudes of the GNP modification with respect to APTES modifications.

FIG. 52-C is a plot of the results from varying the APTES concentration.

FIG. 52-D is a graph of impedance measurements after APTES modification and GNP modification.

FIG. 52-E is a plot of the results from varying the APTES concentration.

FIG. 52-F is a 3D image of the chip surface after GNP modification.

FIG. 53-B is an AFM measurement.

FIG. 53-C is a graph of impedance measurements of a different typical surface modification of APTES (2% concentration).

FIG. 53-D is a graph of impedance measurements on IDES that had a higher than normal aggregation of GNPs.

FIG. 53-E is an image taken of an electrode with an AFM (10 μm×10 μm area shown).

FIG. 54-B is a plot comparing the APTES and MUA modification measurements.

FIG. 54-C is an impedance measurement graph showing the change in impedance due to GNPs.

FIG. 54-D is an image taken using an AFM to show the presence of GNPs, with less aggregation near or over the electrodes.

DETAILED DESCRIPTION

Figure 1:
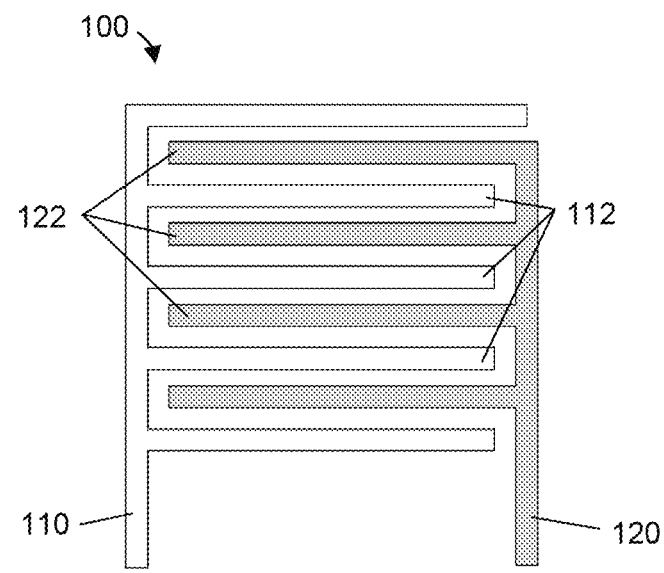
FIG. 1 is a simplified representation of an interdigitated electrode.

This disclosure generally relates to impedance-based molecular sensing systems and methods. In particular, the use of nanoparticles in an impedance-based biosensor may enhance the sensitivity of the impedance measurements and thus may provide more precise results.

According an aspect of the present disclosure, detection is based on immobilizing nanoparticles in between electrodes in response to the presence of a target molecule in a sample to induce a change in the measured electrical impedance of the electrodes. The nanoparticles may be immobilized between the electrodes, for example at or proximate a substrate, without binding to the electrodes themselves. The presence of nanoparticles between the electrodes affects the electric field measured directly between the electrodes. The presence of the nanoparticles generally decreases the electric field magnitude directly between electrodes, which results in a higher measured impedance for the overall electrode than a measurement taken without the nanoparticles present. In this way, the use of nanoparticles may enhance the sensitive and thus accuracy of the biosensor.

According another aspect of the present disclosure, the immobilization of a nanoparticle to the substrate between the interdigitated electrodes, which enhances the change in impedance caused by the presence of the nanoparticle, allows for measuring impedance at one, two, or some other small number of frequencies in order to detect the presence and/or concentration of the target. By measuring impedance at only one, two, or some other small number of frequencies, simpler and/or more compact electronics may be used. This allows for producing inexpensive, portable, and handheld device for target molecule detection. The target molecule may be a biological or chemical agent. The target may be selected from one of ions, metals, toxins, DNA, RNA, small organic molecules, pharmaceutical ingredients, proteins, peptides, antibodies and metabolites. Also, by measuring impedance at one, two, or some other small number of frequencies, together with standard concentration samples of the target, simple calibration curves can be used to determine target concentrations.

According to the present disclosure, the nanoparticles are immobilized between the electrodes using molecular recognition elements (MREs). MREs bind specifically to a particular biomolecule to be detected by the biosensor. An MRE is bound to a substrate or coating of a substrate that extends between the two electrodes. For ease of explanation, the MRE will be referred to herein as being bound to the substrate even though it may be bound to a coating or layer on the substrate. Another MRE is bound to a nanoparticle. When the target is present in the sample being investigated, the MRE bound to the substrate binds with the target. The second MRE bound to the nanoparticle also binds with the target. As a result, the nanoparticle is immobilized relative to the substrate and between the electrodes, which induce a change in the measured electrical impedance across the electrodes. The change in impedance may be detected and measured to determine the presence or absence of the target in the sample.

The sample being investigated may be from a patient, an environmental sample, or a research sample. When the sample is from a patient, the sample may be blood, serum, urine, sputum, tears, prepared from a tissue sample, or any other type of sample.

The nanoparticles may be made of any suitable element or material. In an embodiment, the nanoparticles are gold nanoparticles. In other embodiments, the nanoparticles may comprise metallic nanoparticles, quantum dots (for example silicon dioxide nanoparticles), hybrid nanoparticles such as iron oxide nanoparticles, or coreshell nanoparticles. Coreshell nanoparticles have one material coating another nanoparticle, such as gold coated silicon dioxide nanoparticles. Although embodiments described and illustrated herein use gold nanoparticles, other types of nanoparticles may be used. Thus the use of gold nanoparticles is not meant to be limiting.

The gold nanoparticles provide a change in impedance through the phenomenon of double layer capacitance. Charges in the solution surrounding the nanoparticles build up around the oppositely charged surface of the gold nanoparticles. This forms two layers of charge (i.e. a double layer). The build-up of charge closely resembles the effects of a capacitor. Consequently, the gold nanoparticles provide a capacitive change when bound to the surface between electrodes.

Nanoparticles have been used in a variety of biological applications, such as drug and gene delivery, cancer therapy, and protein detection. Gold nanoparticles have been shown to be highly adjustable in their modification, and assorted methods for binding gold nanoparticles to aptamers and other MREs exist. An aptamer is a biological molecule that can bind to a specific substance with extremely high specificity. Aptamers are typically constructed from oligonucleotides or peptides, but may be constructed using any other suitable materials.

A biosensor according to the present disclosure may be used to detect and/or measure the presence and/or concentration of biological molecules, such as but not limited to DNA, proteins, or metabolites. A sandwich assay may be used to attach gold nanoparticles to a surface such as a substrate. This approach may easily be modified to any available aptamers to detect any number of biological molecules. A limitation on the types of biological molecules that may be detected is the availability and existence of aptamers or other MRE for the specific type of biological molecule. In another embodiment, a competitive binding process may be used rather than a sandwich assay.

The biosensor electrodes may have a microfabricated design and thus may be very small in size. This makes the biosensor very portable. Biological samples are sometimes difficult to obtain and often are only available in small volumes. In some embodiments, the present biosensor may only require the addition of a small volume of solution to the one or more wells of the electrodes, for example around 50 μL, allowing for opportunities to test very small bio-samples accurately. Further, due to the overall simplicity in design and miniaturization, costs of producing the biosensor may be relatively inexpensive compared to some other methods. Moreover, impedance tests may easily be automated and programmed, allowing for users inexperienced with electrical circuitry, such as nurses and doctors, to use the biosensor. This feature may desirable for a point-of-care design. Accordingly, features of one or more embodiments of the present biosensor provide a precise, versatile, inexpensive, and portable point-of-care biosensor device.

According to an aspect of the present disclosure, in order to detect the presence of a molecule, the target molecule must facilitate or prevent binding of nanoparticles which will result in a change in impedance. Beyond this there are generally no limitations on the binding chemistry, and any sort of MRE may be used. As a result, so long as a MRE exists, the target molecule may be measured allowing for a large range of possible molecules that can be detected. Due to the simplicity of impedance detection, this mechanism can be used in an inexpensive handheld device. The mechanism may be used to detect many different targets. Measuring these targets may allow many common diseases to be diagnosed, assessed, and monitored. Additional targets may also be detected including ions, metals, and toxins for environmental testing, and DNA, RNA, and other small molecules such as pharmaceutical ingredients, proteins, peptides, and antibodies for research purposes. Unlike existing detection methods, utilization of this method allows for cheaper, faster quantitative testing. Due to the technical simplicity of the detection, it can be incorporated in a handheld point-of-care device.

Aspects and features according to the present disclosure are now described more fully with reference to the accompanying drawings, in which one or more example embodiments are described and shown. It is to be noted, however, that the present disclosure may be embodied in different forms and should not be construed as limited to the embodiments set forth herein.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

Reference is made to FIG. 1, which is a simplified representation of an existing interdigitated electrode 100. Interdigitated electrode 100 comprises an array having two interlocking or otherwise corresponding electrodes 110, 120 each having a number of individual digits 112, 122, which overlap with those of the other section, essentially creating the same structure as microfabricated capacitors. In reality, interdigitated electrodes often have many more digits than the electrode of FIG. 1. Applying a voltage to an interdigitated electrode, either AC or DC, creates an electric field between the digits. This electric field may be disrupted and altered by the presence of specific target biomolecules, cells, or electrically active labels and the resulting change may then be measured. It has therefore been possible to use interdigitated electrodes in a number of highly sensitive biosensing applications. Many biosensor applications of interdigitated electrodes use gold as the electrode material, due to its biocompatibility.

Beyond being a simple interface, the properties of the electrodes used in electrical and electrochemical biosensors can have a significant impact on the function and effectiveness of the resulting biosensor system. The effectiveness of the biosensor generally refers to the sensitivity and impedance change response of the sensor.

Figure 2:
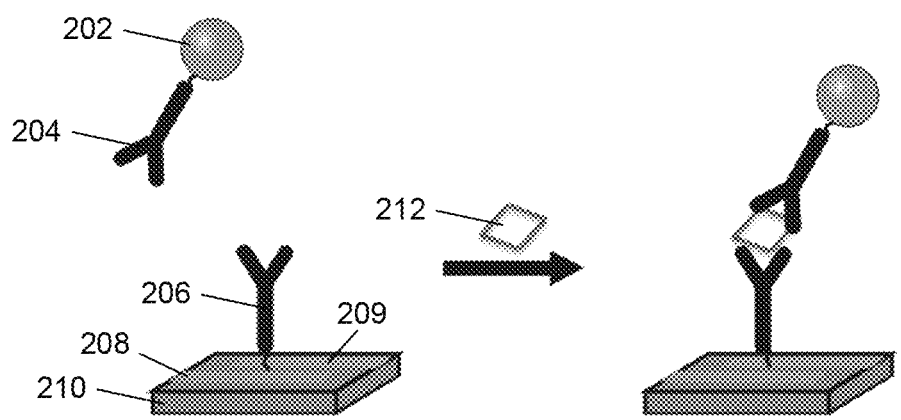
FIG. 2 is a representation of a process of immobilizing a nanoparticle at a substrate between electrodes according to the present disclosure.

As previously described, the present disclosure utilizes one or more nanoparticles to enhance an impedance-based biosensor. Molecular recognition elements (MREs) are used to immobilize the nanoparticles between the electrodes. Reference is made to FIG. 2, which shows a representation of the process of immobilizing a nanoparticle 202 at a substrate 210 between electrodes 208, 209. In the example, the MREs are antibodies 204, 206. Nanoparticle 202 comprises an antibody 204 bound to its surface. Nanoparticle 202 may be suspended in a fluid. A capture antibody 206 is bound to substrate 210 at a location disposed between electrodes 208, 209. In the presence the target biomolecule 212, target 212 binds with both the capture antibody 206 and the antibody 204 bound to the nanoparticle 202. Again, the antibody MREs bind specifically to the particular biomolecule to be detected by the biosensor. Through the binding of the target to the capture antibody 206 and the antibody 204 bound to the nanoparticle 202, the nanoparticle 202 is immobilized relative to the substrate and between the electrodes. The presence of bound nanoparticles between the electrodes 208, 209 disrupts the electric field around the electrodes leading to increased measured impedance. The increased impedance occurs in at least one or more frequency bands. In some cases, the measured impedance may be lower at other frequencies, but the change is typically less significant compared to the increase in the other frequency band. It is noted that in a situation where nanoparticles are bound on top of electrodes, there is generally a decrease in the measured impedance compared to when no nanoparticles are present. However, when gold nanoparticles are immobilized between electrodes, as opposed to on the electrodes themselves, there is a greater change in the measured impedance and overall the change is an increase within the frequency range of interest. It has been determined that this approach is effective for detecting a variety of target biomolecules. It should be noted the relative sizes of the components in FIG. 2 are drawn out of proportion.

The MREs may be any suitable type of recognition elements including aptamers or binding proteins, depending on the target biomolecule. Aptamers are single strands of DNA or polymers with structures that can be designed to bind specifically to target biomolecules. Other types of MREs include antibodies, RNA, RNA fragments, DNA, and DNA fragments.

A number of different factors contribute to the conditions required for precise detection. In the case of impedance-based detection, an important factor is often the electric field generated at the electrode and how the electric field may be best influenced for effective detection. These factors may include the digit width, spacing and height in the interdigitated electrode, applied voltage to the electrode and the particular background solution used for testing. Since, as in many biosensor applications, measurement takes place in an aqueous environment, controlling the background solution may be an important consideration. This is so that the solution does not interfere with measurements, does not interfere with the target biomolecule or recognition elements, and does not interfere negatively with the electrode. In an embodiment, some interference with the electric field in the system is beneficial in making a more sensitive biosensor as the ionic concentration of a background solution establishes an electrical screening layer that, with the right design, isolates the electric field to only the region around the electrode where binding and detection occurs, increasing sensitivity. In an embodiment, the region around the electrode includes the area between the electrode and an adjacent electrode.

Figure 3:
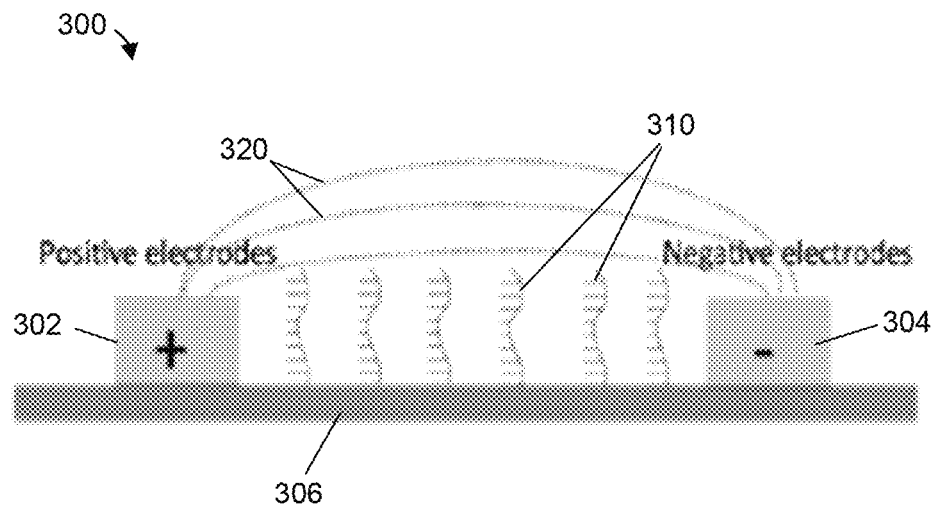
FIG. 3 is a representation of a detection device of an example biosensor in the absence of both target biomolecules and nanoparticles.

FIG. 3 is a representation of a detection component or device 300 of an example biosensor in the absence of both target biomolecules and nanoparticles. Detection component 300 comprises a first electrode 302, a second electrode 304 spaced apart from first electrode 302, and a substrate 306 extending between the two electrodes 302, 304. A number of MREs 310 are bound to substrate 306 between electrodes 302, 304. Lines 320 represent the electric field between electrodes 302, 304.

Figure 4:
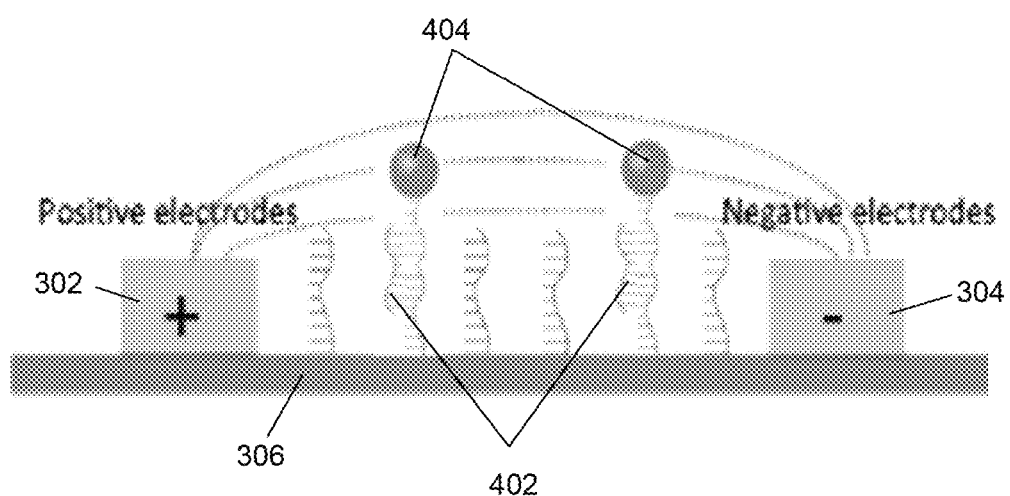
FIG. 4 is a representation of detection component of FIG. 3 in the presence of both target biomolecules and nanoparticles.

FIG. 4 is a representation of detection component 300 of FIG. 3 in the presence of both target biomolecules 402 and nanoparticles 404. The MREs, which only bind with the target biomolecule of interest, result in the gold nanoparticles 404 being immobilized between electrodes 302, 304 in the manner previously described. The presence of gold nanoparticles 404 between electrodes 302, 304 changes the electric field between electrodes 302, 304 and results in a change in impedance across the electrodes.

Figure 5:
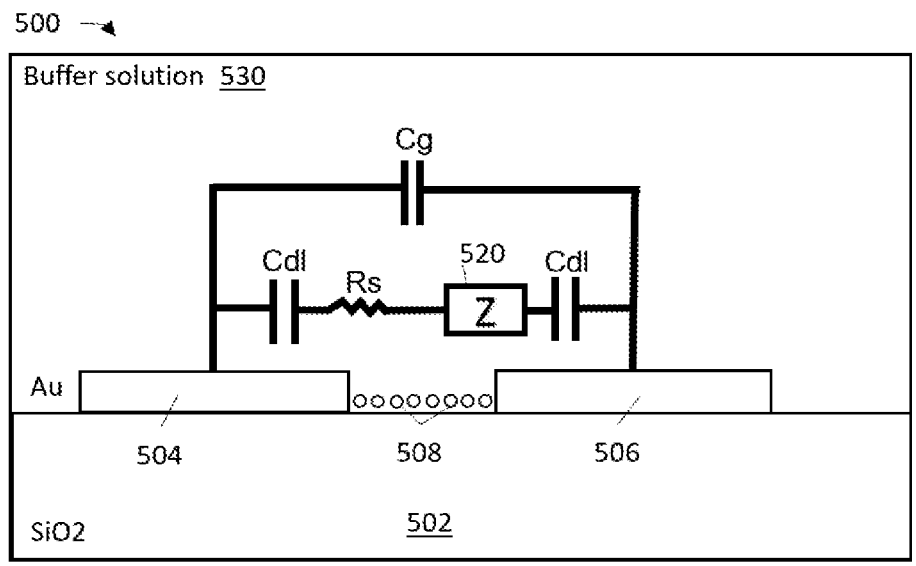
FIG. 5 is a circuit diagram of an equivalent circuit of the embodiment of detection component of the example biosensor of FIGS. 3 and 4.

FIG. 5 is a circuit diagram 500 of an equivalent circuit of the embodiment of detection component 300 of the example biosensor of FIGS. 3 and 4.

Again, according to the present disclosure, the sensitivity of the impedance measurements may be improved by using nanoparticles such as gold nanoparticles. An improvement in the sensitivity of the impedance measurements generally yields more precise results. The mechanism by which gold nanoparticles affect the impedance of the system may be represented using the equivalent circuit 500 shown in FIG. 5. Circuit 500 comprises a silicon dioxide substrate 502, and gold electrodes 504, 506. Nanoparticles 508 are immobilized between electrodes 504, 506 at or proximate to substrate 502. This circuit is a combination of the double layer capacitance of the electrode digits ($C_{dl}$), the physical capacitance of the electrode ($C_g$), the resistance of the surrounding buffer solution ($R_s$), and the impedance introduced by the bound nanoparticles (Z), represented by box 520.

Since detection component 300 is a non-faradic system that does not depend on electron transfer from electrochemical reactions, complex elements, such as electron transfer resistance and mass transfer resistance are generally not needed. The gold nanoparticles provide a change in impedance through the phenomenon of double layer capacitance. Charges in the solution surrounding the nanoparticles build up around the oppositely charged surface of the gold nanoparticle. This forms two layers of charge (double layer). The build-up of charge closely resembles the effects of a capacitor. Consequently, the gold nanoparticles provide a capacitive change when bound to the surface between electrodes.

Figure 6:
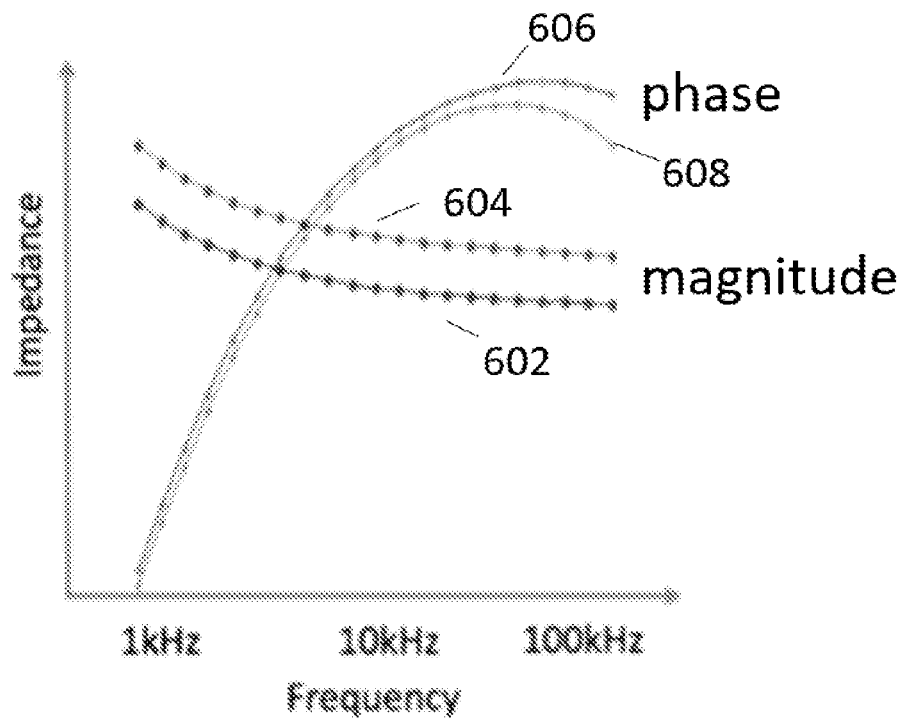
FIG. 6 is a graph showing example magnitude and phase values of the electrical impedance measured across electrodes of a biosensor according to the present disclosure.

FIG. 6 is a graph showing example magnitude and phase values of the electrical impedance measured across electrodes of a biosensor according to the present disclosure. The graph shows magnitude values 602 and phase values 606 values in the absence of gold nanoparticles, which may be compared to magnitude values 604 and phase values 608 values in the presence of gold nanoparticles. Again, the nanoparticles get immobilized between the electrodes in the presence of the target. The values span an approximately frequency range of 1 kHz to 100 kHz. The graph shows the magnitude component of the impedance increases and the phase component decreases in the present of the nanoparticles. The addition and immobilization of nanoparticles leads to a higher impedance and a decrease in the total capacitance of the sensor. This decrease in capacitance is indicated by the decrease in phase. There is a greater influence of capacitance, but since impedance is inversely proportional to capacitance, there is an overall decrease in the total capacitance of the electrode even though more capacitors are added.

Figure 7:
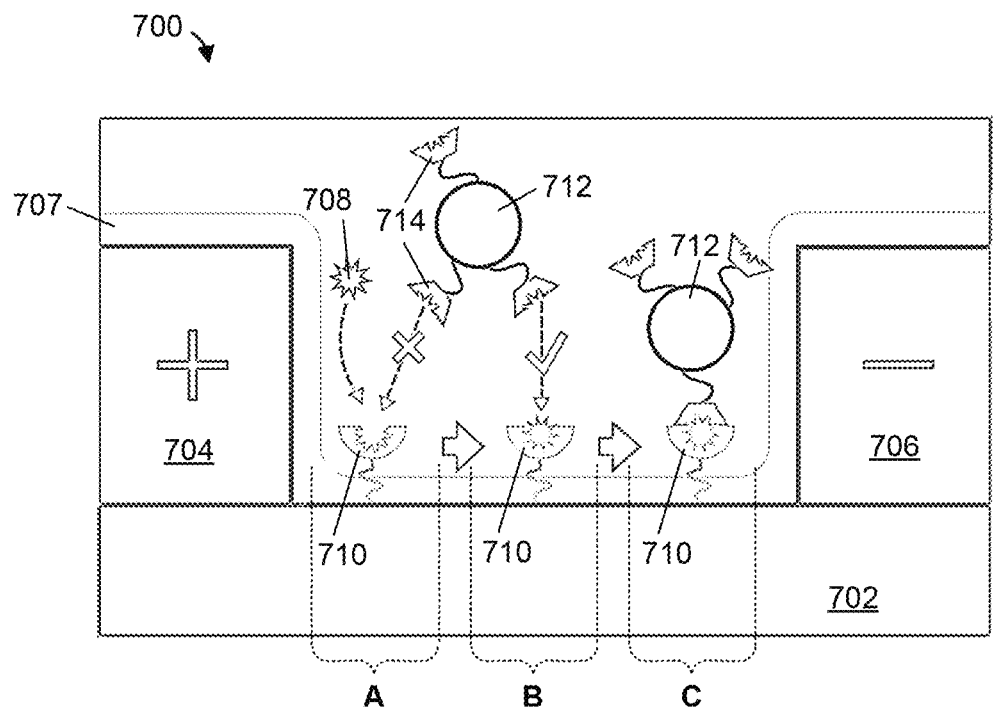
FIG. 7 is a representation of a detection component of an example biosensor according to the present disclosure showing the immobilization of a gold nanoparticle between two electrodes in a sandwich assay.

FIG. 7 is a representation of a detection component 700 of an example biosensor according to the present disclosure showing the immobilization of a gold nanoparticle between two electrodes in a sandwich assay. The immobilization process is shown in three stages A, B, and C for the purposes of explanation. Detection component 700 comprises a substrate 702, first and second electrodes 704, 706, which may be adjacent digits of an interdigitated electrode, and an electric double layer 707. An electric double layer 707 forms around the electrodes, which comprises two layers of ions that form the double layer capacitance and defines the screening distance. In stage A, an MRE 710 that is bound to substrate 702 is available to bond with target biomolecule 708. An MRE 714 bound to nanoparticle 712 will not bond to MRE 710 as indicated by the "X" in FIG. 7. In stage B, target biomolecule 708 binds with MRE 710. MRE 714 bound to nanoparticle 712 is available to bond with target biomolecule 708. In stage C, one of MREs 714 binds to nanoparticle 712, which is already bound to MRE 710. It is to be appreciated that although FIG. 7 shows target 708 binding with MRE 710 before target 708 binds with MRE 714, in fact target 708 may bind with MRE 714 before or at the same time as target 708 binds with MRE 710. Accordingly, the binding of target biomolecule 708 with MRE 710 and MRE 714 immobilizes nanoparticle 712 between electrodes 704, 706 and therefore changes the impedance between electrodes 704, 706. The detection of the impedance change indicates the presence of the target biomolecule in the sample under investigation.

Figure 8:
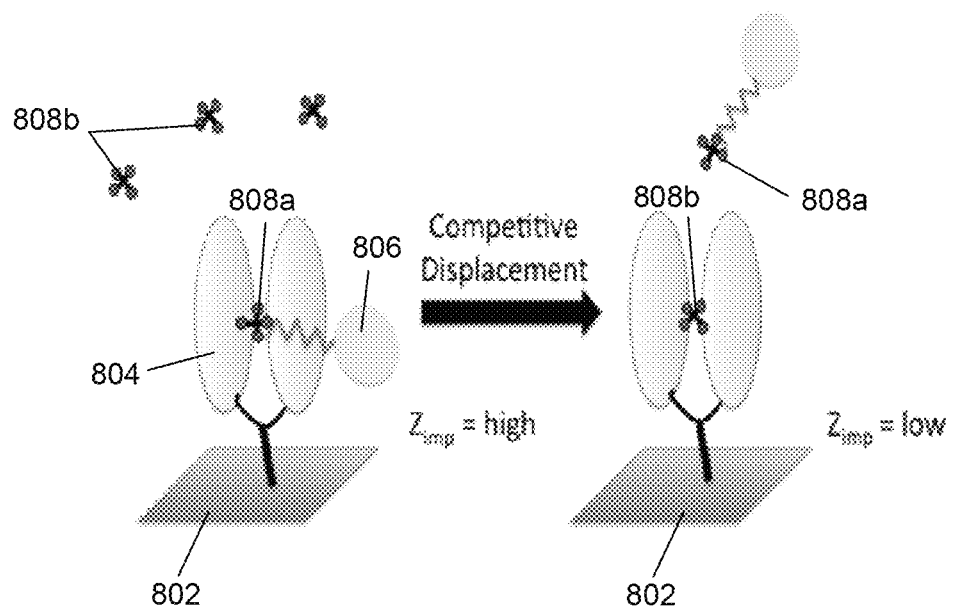
FIG. 8 is a representation of an example competitive binding process.

Although embodiments have been described that use a sandwich assay process, this is not meant to be limiting. Other processes may be used. FIG. 8 is a representation of an example competitive binding process. A competitive binding may be used, for example, to release nanoparticles that are already present between the electrode digits, or a set of two interdigitated electrodes on which binds nanoparticles when the biomolecule is present and other releasing nanoparticles when the biomolecule is present, to improve sensitivity and/or reduce or eliminate false positive detection.

On the left hand side of FIG. 8, a protein MRE 804 is bound to a gold electrode 802. A gold nanoparticle 806 is bound to a metabolite 808a. Other metabolites 808B are free, in this case in urine. The impedance at electrode 802 caused by the presence of the nanoparticle 806 is high. The right hand side of FIG. 8 shows the situation after metabolite 808a has been competitively displaced by one of the free metabolites 808b. The nanoparticle 806 is no longer immobilized at electrode 802 and therefore the impedance at electrode 802 is lower than it was when the nanoparticle 806 was present.

Process/Method of Use

Figure 9:
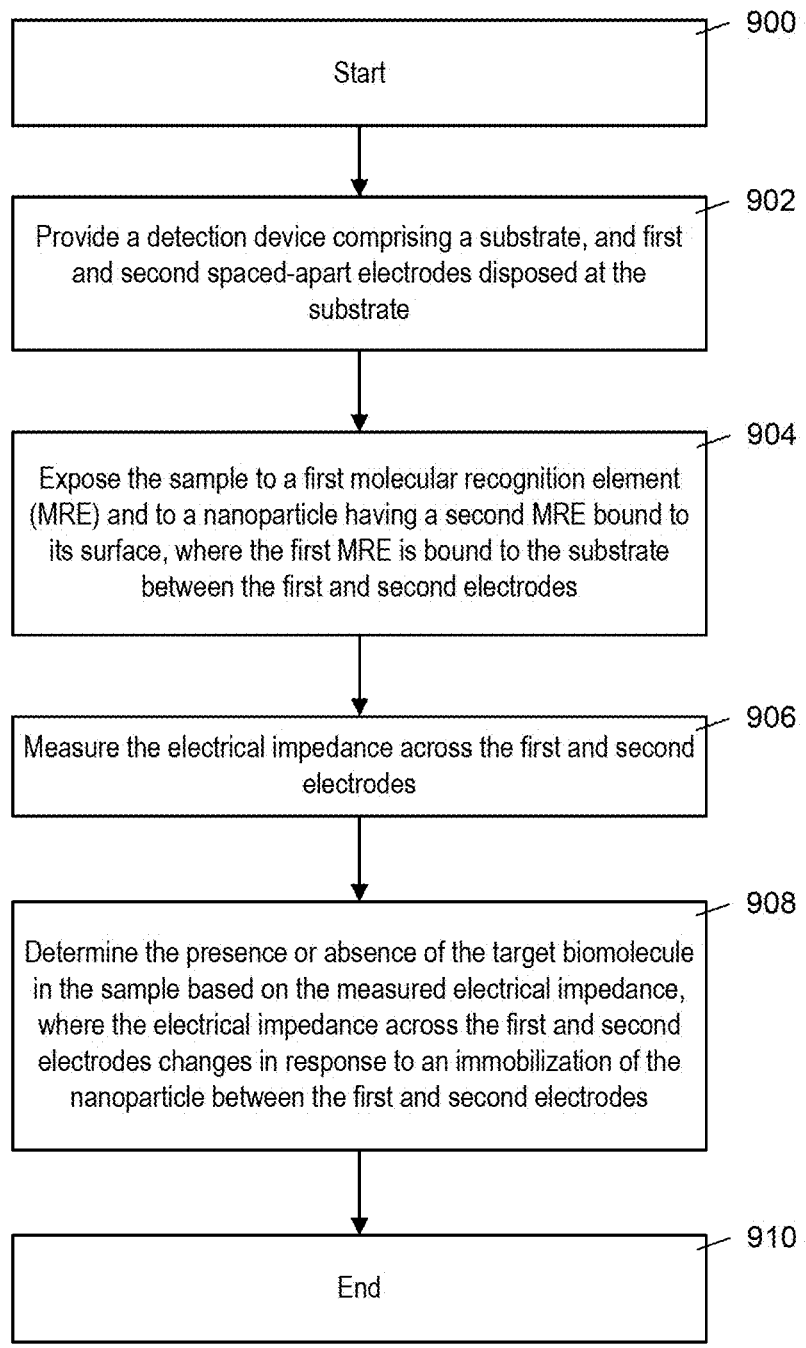
FIG. 9 is a process flow diagram of operations in an example method of detecting a target biomolecule in a sample according to the present disclosure.

FIG. 9 is a process flow diagram of operations in an example method of detecting a target biomolecule in a sample according to the present disclosure.

The process starts at block 900 and proceeds to block 902 where a detection device is provided comprising a substrate, and first and second spaced-apart electrodes disposed at the substrate. A first molecular recognition element (MRE) is bound or otherwise immobilized at or proximate the substrate and between the first and second electrodes. The impedance across the first and second electrodes may then be measured to provide a baseline.

The process proceeds to block 904 where the sample is exposed to the first molecular recognition element (MRE) and to a nanoparticle having a second MRE bound to its surface. The nanoparticles may be introduced at this stage, meaning after the baseline impedance measurement. The first and second MREs are adapted to bind with the target biomolecule.

The process proceeds to block 906 where the electrical impedance across the first and second electrodes is measured.

The process proceeds to block 908 where the presence or absence of the target biomolecule in the sample is determined based on the measured electrical impedance. The electrical impedance across the first and second electrodes changes in response to an immobilization of the nanoparticle between the first and second electrodes due to binding of the target biomolecule with the first MRE and binding of the target biomolecule with the second MRE. The change in impedance may be measured by comparing the measured impedance in the presence of the nanoparticles to the baseline impedance measurement when no nanoparticles were present.

The process proceeds to block 910 where the process ends.

In an embodiment, an electrolyte, such as 150 micromolar KCl solution, may be used with the fluid for detection. Other additions may include buffers and/or preservatives, as well as other reagents commonly used in binding assays, such as ELISA assays.

In an embodiment, the biosensor may comprise a microfluidic device for accepting a fluid sample and delivering the fluid sample to the interdigitated electrodes. The microfluidic device may perform one or more of removing cells from the fluid sample, adding buffers and/or electrolytes to the fluid sample, and/or adding the nanoparticles to the fluid sample.

For example, in an embodiment comprising a microfluidic system, the electrode may be contained in a cartridge with chambers preloaded with washing and/or measurement buffer, and modified nanoparticles in solution. After a biological sample is loaded in, a small fluidic pump may automatically move the sample onto the electrodes, followed by the nanoparticles, and then the buffers. Using this technique makes the process more consistent and easy to use overall. Accordingly, in this embodiment, the system is automated and the electrode cartridges contain all of the required materials for a single test. The cartridges may be disposed of after a single use.

Figure 18:
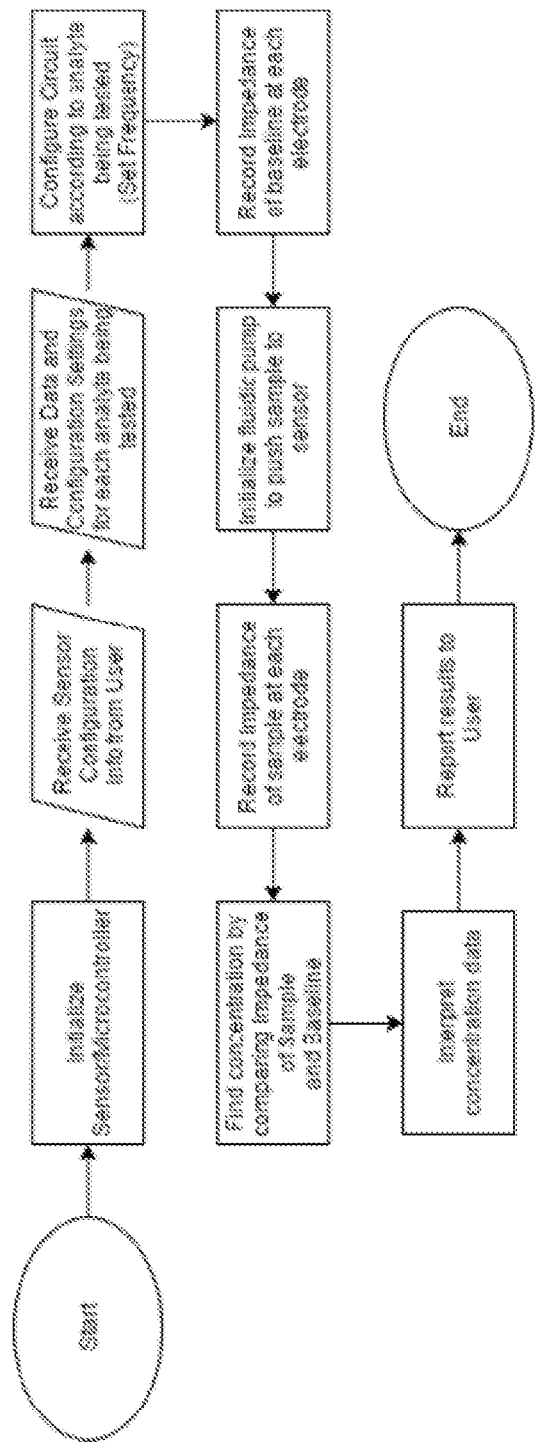
FIG. 18 is a process flow diagram of operations in an example method of using a biosensor according to the present disclosure.
Figure 21A:
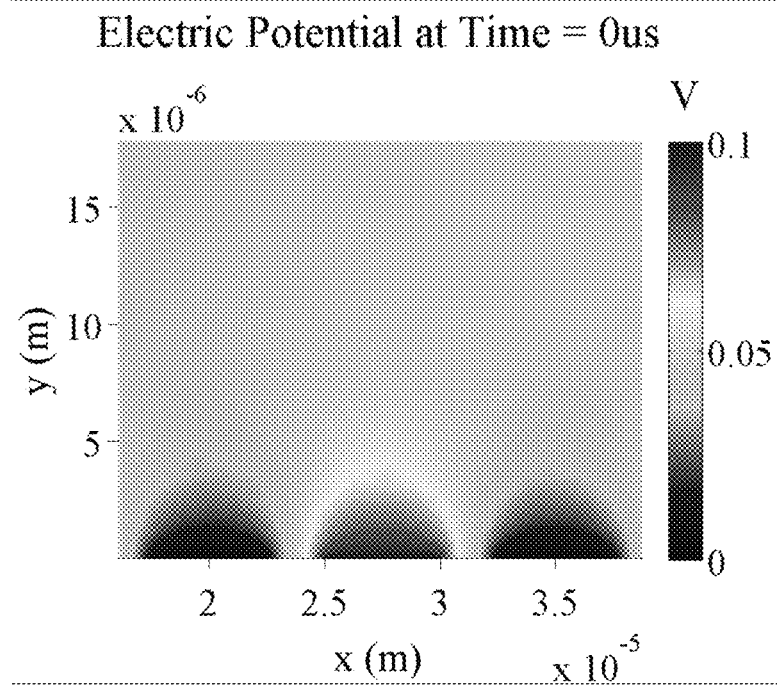
FIG. 21-A is a plot of the electric potential of IDEs (5 μm digit width and 2.5 μm spacing) with 0.1 V DC applied with a background KCl concentration of 150 μM take at t=0 seconds.
Figure 21B:
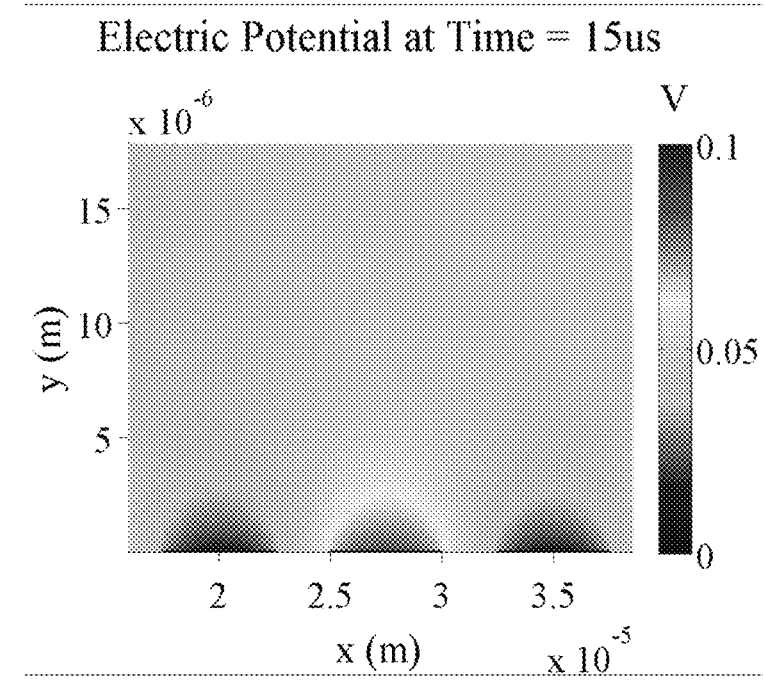
Figure 21C:
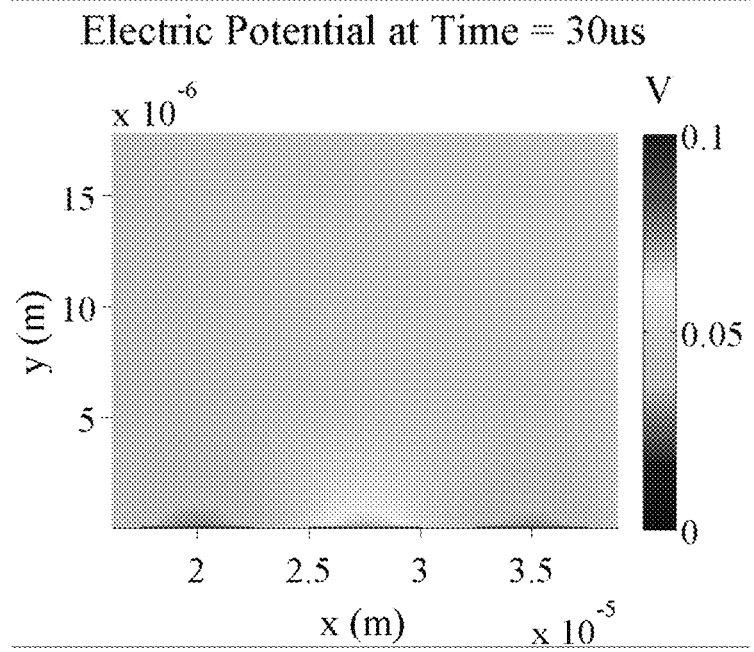
Figure 21D:
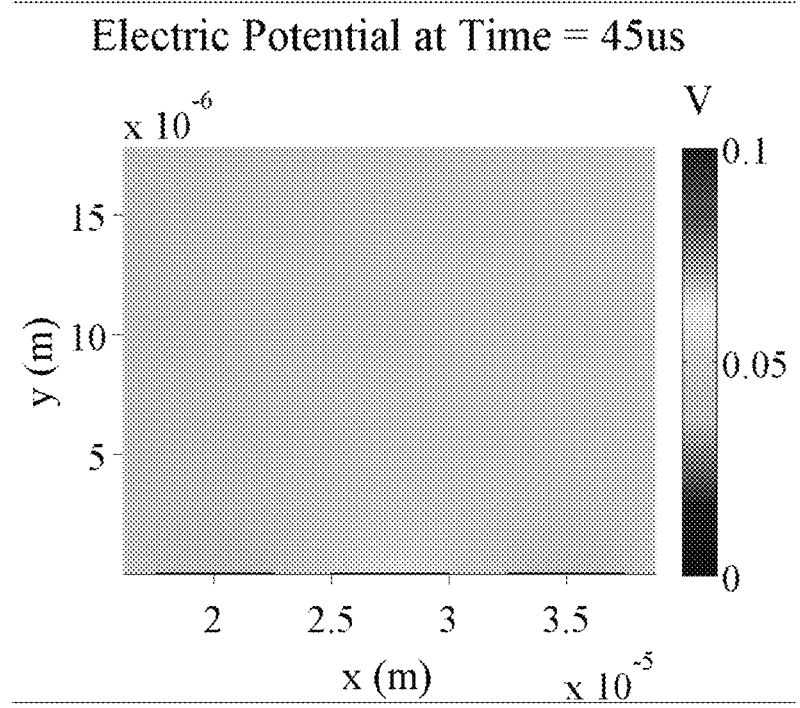

FIG. 18 is a process flow diagram of operations in an example method of using a biosensor according to the present disclosure.

Process/Method of Manufacture

Figure 10:
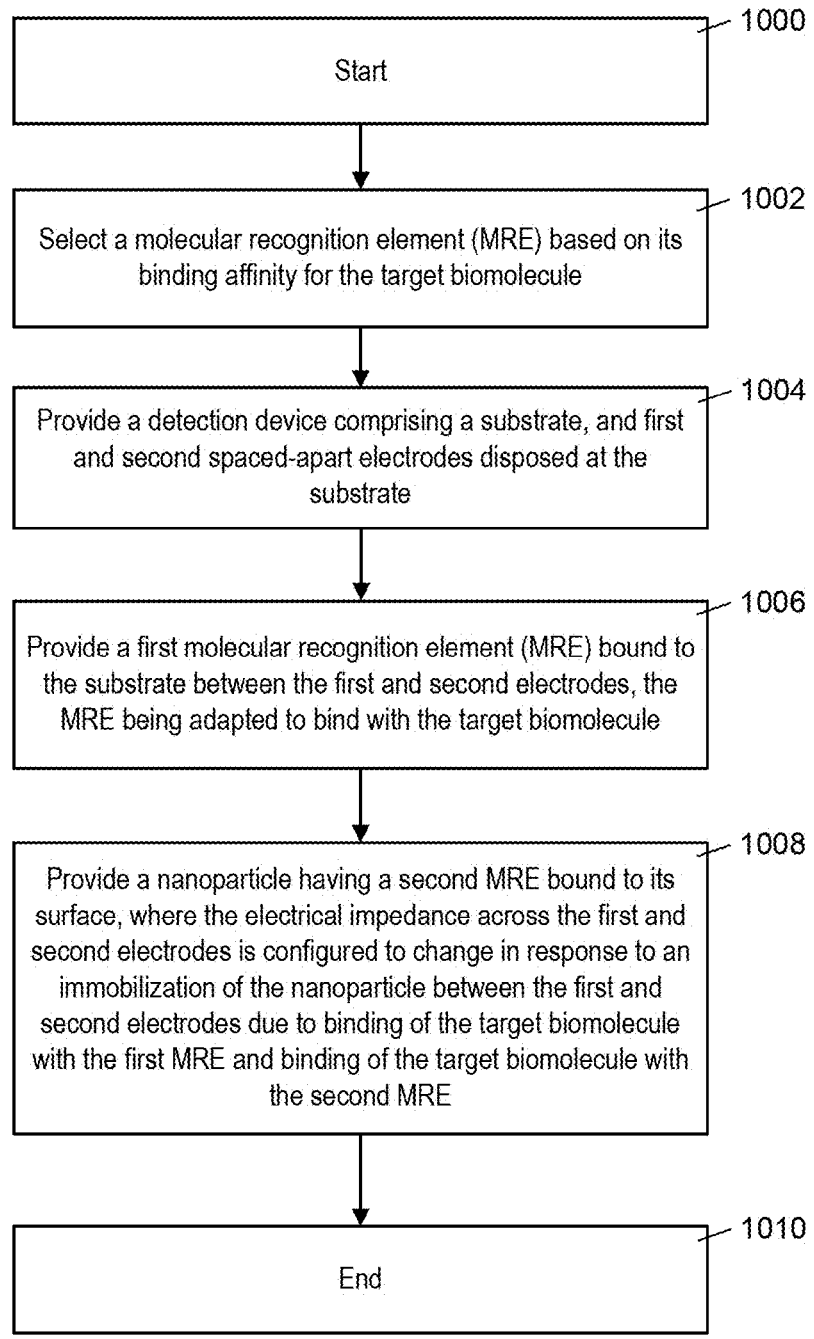
FIG. 10 is a process flow diagram of operations in an example method of manufacturing a biosensor for detecting a target biomolecule in a sample according to the present disclosure.

FIG. 10 is a process flow diagram of operations in an example method of manufacturing a biosensor for detecting a target biomolecule in a sample according to the present disclosure.

The process starts at block 1000 and proceeds to block 1002 where a molecular recognition element (MRE) is selected based on its binding affinity for the target biomolecule.

The process proceeds to block 1004 where a detection device is provided comprising a substrate, and first and second spaced-apart electrodes disposed at the substrate.

The process proceeds to block 1006 where a first molecular recognition element (MRE) is provided bound to the substrate between the first and second electrodes, the MRE being adapted to bind with the target biomolecule.

The process proceeds to block 1008 where a nanoparticle having a second MRE bound to its surface is provided, where the electrical impedance across the first and second electrodes is configured to change in response to an immobilization of the nanoparticle between the first and second electrodes due to binding of the target biomolecule with the first MRE and binding of the target biomolecule with the second MRE.

The process proceeds to block 1010 where the process ends.

Other aspects and features according to the present disclosure are now described.

Nanoparticles

Nanoparticles are generally considered to be particles having a size between 1 and 100 nanometres (nm). In nanotechnology, a particle is defined as a small object that behaves as a whole unit.

As previously mentioned, the nanoparticles may be made of any suitable element or material, including but not limited to gold or aluminum. In general, the material or materials used are stable, meaning they can exist in solution for periods of time without aggregating, dissolving, crashing out, and modifiable, meaning that MREs may be attached to the nanoparticles. Depending on the process used to create the nanoparticles, for example gold nanoparticles, the nanoparticles can be stable for months.

In an embodiment, the nanoparticles are gold nanoparticles having a diameter of within the approximate range of 15 nm to 60 nm. In an embodiment, the nanoparticles have a diameter of approximately 15 nm, 30 nm, or 60 nm. In other embodiments, however, the diameters of the nanoparticles may be of any other suitable size, including 1-100 nm, 5-60 nm, 10, 15, 20, 30, 40, or 50 nm. The size of the nanoparticles does not seem to have a significant effect on the effectiveness of the biosensor. In at least some embodiments, the stability of the nanoparticle is more of a concern that its shape or size. In an embodiment, core-shell nanoparticles, such as nanoparticles comprising a dielectric coated with gold, may be used. In another embodiment, nanoparticles such as polymeric nanoparticles and/or latex particles may be used.

Electrodes

The electrodes may be made of or comprise gold, a gold alloy, aluminum, an aluminum alloy, or any suitable material or materials. The electrodes may be patterned on a suitable substrate, for example a silicon dioxide substrate, such as silicon dioxide on silicon wafers, on an alumina substrate, or on a glass substrate. In general, the substrate is non-conductive. In an embodiment, the substrate is modifiable, meaning that its surface can be modified with a layer or layers of chemically bound entities such as short chain polymers, organic molecules, or biomolecules.

Microfabrication can yield chips with slightly different dimensions. Gold is generally more difficult to work with in regards to microfabrication compared to aluminum because of the natural chemical stability of gold. The chemicals required to wet etch gold tend to be corrosive enough to destroy other structures on the chip that should be kept fixed. Inevitably, gold electrode chips are often slightly over-etched when wet etching is used, leading to more spacing between the electrodes. In some embodiments, dry etching techniques may be used instead of wet etching. Dry etching does not discriminate between materials. Thus there is generally no over etching when dry etching is used.

It has been determined that aluminum interdigitated electrodes acted similar to gold interdigitated electrodes in impedance tests. They produced similar trends under the same surface modifications, meaning having nanoparticles immobilized at their substrates, in comparison with themselves and simulation tests. While aluminum is generally both easier and cheaper to microfabricate electrode chips, gold has been shown to be more chemically stable, and will not interfere with many biological molecules. Furthermore, the electrode material may be changed based on the target biomolecule being detected. This may allow for greater adaptability and more opportunities in types of molecules that can be detected.

The dimensions of the electrode may be as small as is practical. Examples include from a 1:1 to 2:1 digit width to gap ratio. The digit width is the width of each digit of the pair of electrodes. The gap refers to the distance between adjacent digits of each of the electrodes. In an embodiment, the digit width and gaps of the interdigitated electrodes are as small as practical, limited by standard photolithographic and etching techniques; wet etching may be used, but other techniques such as reactive ion etching, lift-off lithography, and electron-beam lithography are possible. Example digit widths are 2-4 microns, and gap spacing of 2-5 microns; 1-2 microns for the digit widths and/or gap spacing is also possible. Other digit widths and gap spacing may also be used. In at least some embodiments, the sensitivity and impedance change response of the biosensor is significantly better with smaller gaps. In an embodiment, the digit width is approximately 5 microns and the gap spacing is approximately 2.5 microns.

It has been determined by the inventors that the smaller the electrode dimensions, the more sensitive the sensor is to bound nanoparticles. Digit width and digit spacing are generally of particular importance, with smaller inter-digit spacing generally resulting in more sensitive detection. Dimensions in the range of several micrometers, for both the digit width and spacing, have been shown to be effective for the detection of cells and bacteria, whereas electrodes with sub-micron dimensions have been made which are sensitive enough to detect DNA hybridization. The increased sensitivity achievable with smaller electrode dimensions makes physical sense as well. The closer together the digits of the electrode are, the more confined the electric field becomes, like a parallel plate capacitor. Therefore, effects of disruptions in these electric fields are more pronounced. Conversely, the electric fields between larger gaps will be less sensitive, making them better suited for detecting larger species, such as attached cells or bacteria. Therefore for this application electrodes may be designed to have the smallest dimensions possible, but the benefit of smaller dimensions may become less significant as the dimensions decrease. Electrodes with slightly larger dimensions may still be nearly as effective without having to resort to more expensive and specialized microfabrication techniques to yield the smallest dimensions possible.

The size of the nanoparticles and their locations in the biosensor when immobilized can have an effect on the sensitivity of the biosensor. Commonly used biological recognition elements, such as proteins and aptamers, can vary in size greatly, and extra molecules and modifications are sometimes necessary to facilitate bonding to the electrodes or nanoparticles. For example, if the binding molecules attaching the nanoparticles to the substrate are too long, the nanoparticles will be outside of the electrical screening distance of the biosensor system. This may result in a negligible difference in electric field magnitude with and without nanoparticles. This screening distance is directly related to the double layer capacitance of the system and limits the influence of the electric field above and between electrode digits. The electric screening distance of the system may be adjusted by changing the background ion concentration, which is the source of the screening, and which may potentially change the effect of the bound nanoparticles.

The size of gold nanoparticle used may also be influenced by the individual applications, as different modifications to nanoparticles are necessary for different biosensor applications (e.g., different attachment molecules required to bind to nanoparticles).

It has been determined that the size of the nanoparticles used has a low impact on the sensitivity of the biosensor. Comparable results were obtained with gold nanoparticles of 30 nm, 60 nm, and 120 nm. This indifference to the size of the nanoparticles is most likely due to the electrical screening layer established over the electrode. In each case, regardless of the size of the nanoparticles, the amount of gold in the areas over the electrodes that actually influence the electric field in the gaps stays approximately constant. In any event, smaller gold nanoparticles may be advantageous for better stability in solution and better packing efficiency when bound to electrode surfaces, whereas larger nanoparticles may be modified with more binding molecules for better binding efficiency.

Figure 11:
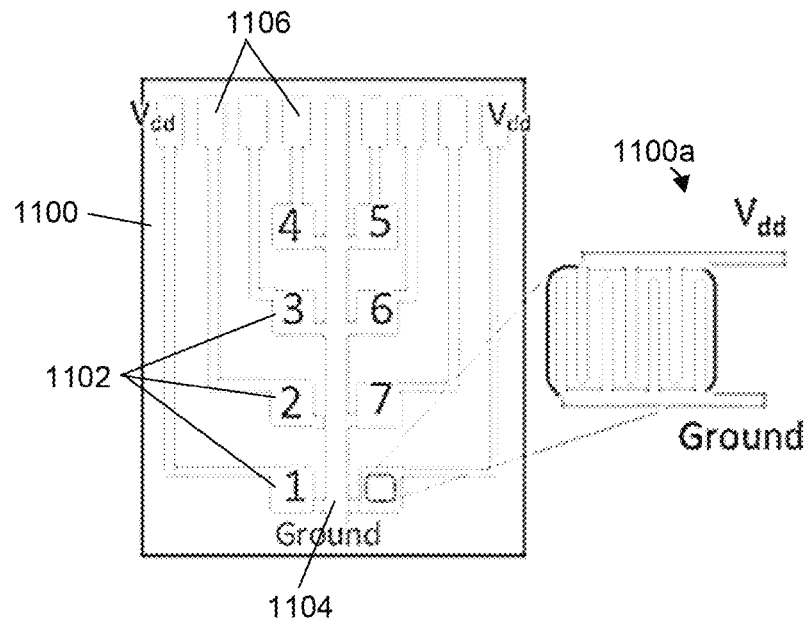
FIG. 11 is a schematic of an example embodiment of a chip comprising multiple 3 mm×3 mm interdigitated electrodes on a silicon dioxide substrate.

In an embodiment, a microfabricated chip with an interdigitated electrode may be used to characterize gold nanoparticles bound to its surface. A single chip may comprise multiple biosensors each having an interdigitated electrode located in a well. FIG. 11 shows an example embodiment of a chip 1100 comprising eight interdigitated electrodes 1102 (numbered 1 through 8) on a substrate. In this embodiment, the interdigitated electrodes are 3 mm×3 mm electrodes and the substrate is a silicon dioxide substrate. Each interdigitated electrode 1102 is connected with a Vdd line 1106 and a ground line 1104. One of the interdigitated electrodes 1102 is shown in greater detail in inset 1100a.

Figure 12:
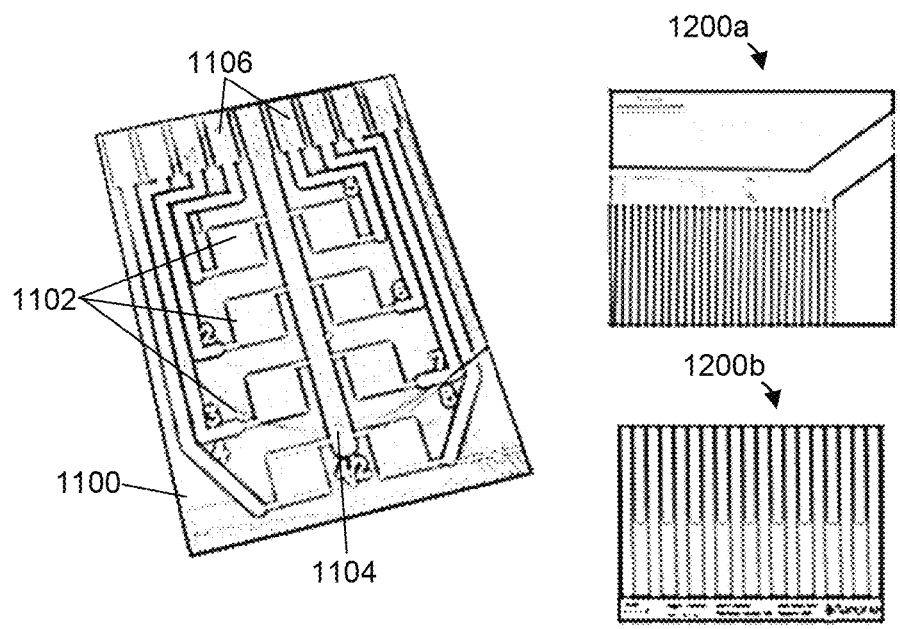
FIG. 12 is photograph of an embodiment of a microfabricated chip comprising multiple interdigitated electrodes.

FIG. 12 is photograph of an embodiment of a microfabricated chip comprising multiple interdigitated electrodes similar to the chip depicted in FIG. 11. Inset 1200a shows a microscopy image of one of the interdigitated electrodes, while inset 1200b shows a scanning electron microscope image of one of the interdigitated electrodes. In this embodiment, the electrodes were created using standard photolithographic microfabrication techniques to create 2 μm of spacing between electrode digits that are 4 μm wide. Evidence has shown that the smaller the spacing, the more sensitive the impedance is to the presence of chemical species in between interdigitated electrodes.

In an embodiment, a single chip comprising multiple biosensors, such as those of FIGS. 11 and 12, may be configured so that different biosensors detect different target biomolecules. This may allow for the simultaneous detection of multiple biomolecules with a single sample.

Figure 13:
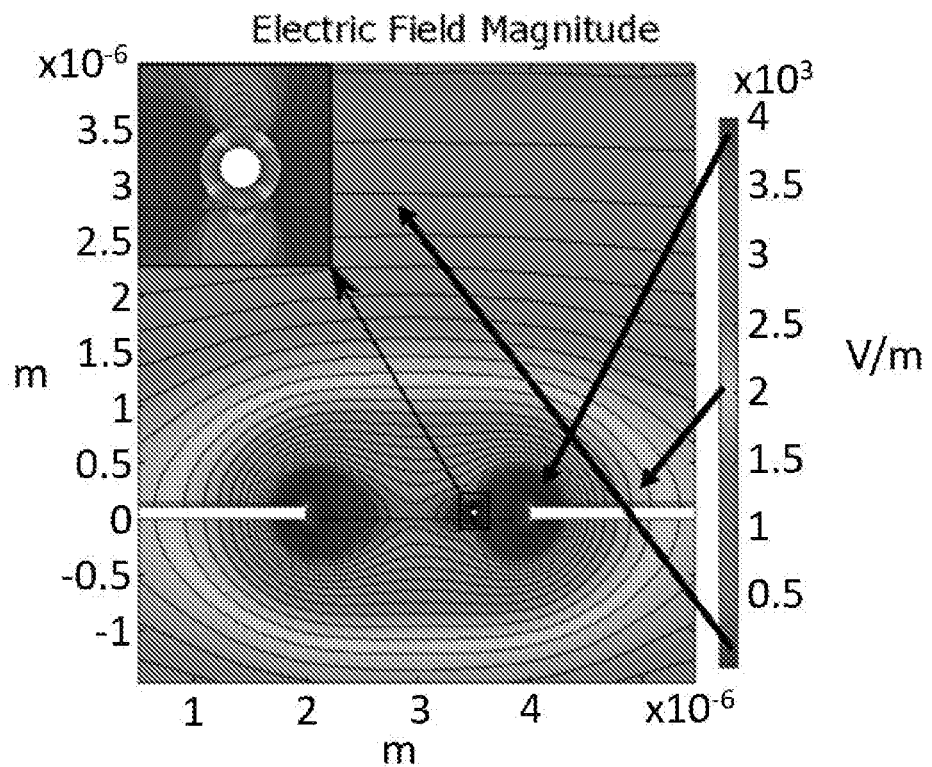
FIG. 13 is a graph of electric field magnitude of example results from simulations of a biosensor having interdigitated electrodes with bound gold nanoparticles.
Figure 14:
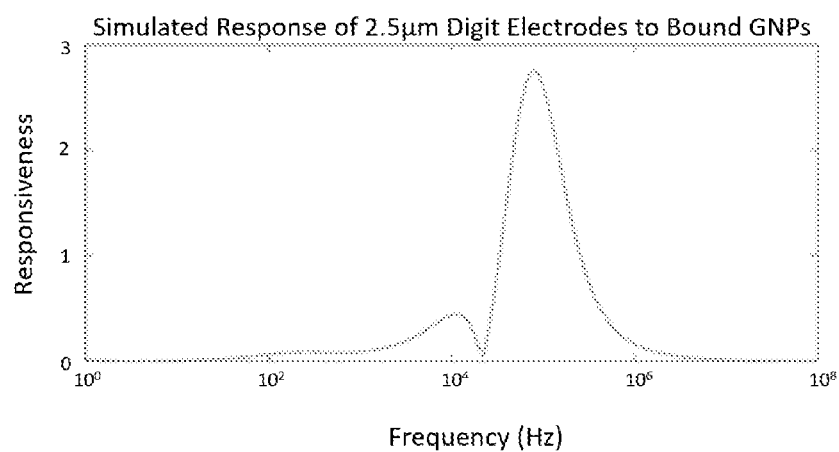
FIG. 14 is a graph showing the impedance magnitude sensitivity of interdigitated electrodes to gold nanoparticles bound to different positions between electrode digits as a function of frequency

FIGS. 13 and 14 show example results from simulations of the electrical properties of an interdigitated electrodes with bound gold nanoparticles made using COMSOL Multiphysics. FIG. 13 represents electric field magnitude. FIG. 14 is a graph showing the impedance magnitude sensitivity of interdigitated electrodes to gold nanoparticles bound to different positions between electrode digits as a function of frequency, where "responsiveness" is the percent difference in the impedance phase between the electrode with and without bound nanoparticles.

The results in FIGS. 13 and 14 show the layout of the simulation along with the associated electric field distribution, and the simulated sensitivity of interdigitated electrodes to bound nanoparticles. Results show a specific distribution of sensitivities for nanoparticles bound to interdigitated electrodes as well as the predicted behavior and frequency range of interest for impedance measurements. The purpose of experiments presented here are as proof-of-concept experiments of the detection principle shown by the simulations. In theory, the change in impedance relies only on the binding of nanoparticles, so directly binding gold nanoparticles chemically to interdigitated electrodes should result in the same effect as the simulations. The simulation also proves the efficacy of this method to be used with molecular recognition elements for future biosensing applications.

Figure 15:
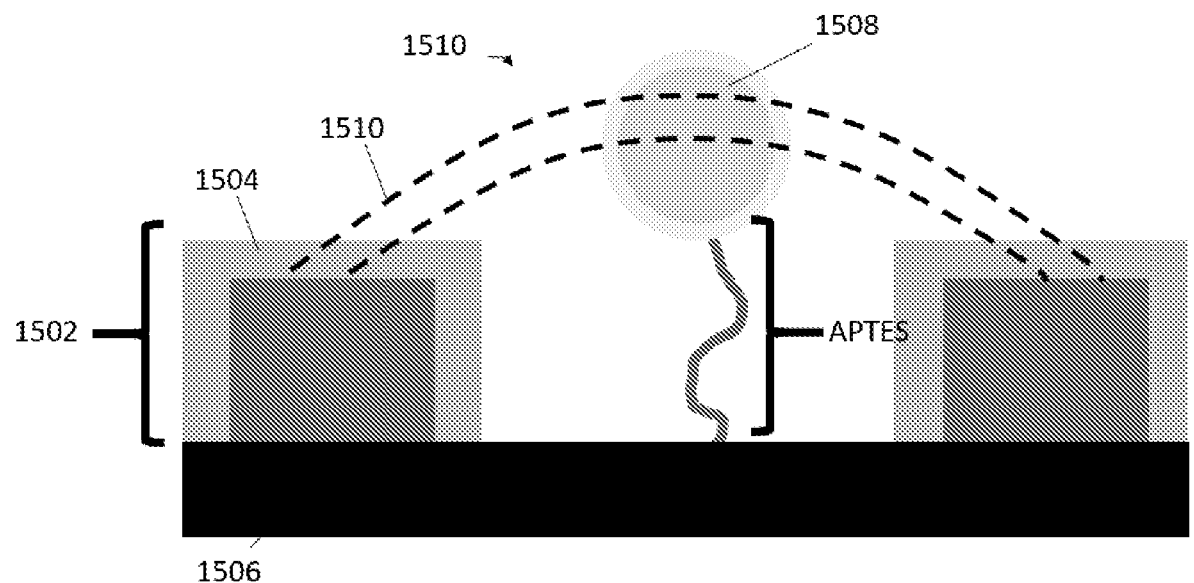
FIG. 15 is a cross sectional representation of a detection device 1500 of a biosensor having electrodes made of aluminum.

Tests were performed on chips made of either aluminum or gold electrodes. FIG. 15 is a cross sectional representation of a detection device 1500 of a biosensor having electrodes made of aluminum. Detection device 1500 comprises a substrate 1506 and aluminum electrodes 1502, which have an oxide coating 1504, which acts as a capacitor. An immobilized nanoparticle 1508, a free nanoparticle 1612, and electric field lines 1510 are also shown.

Figure 16:
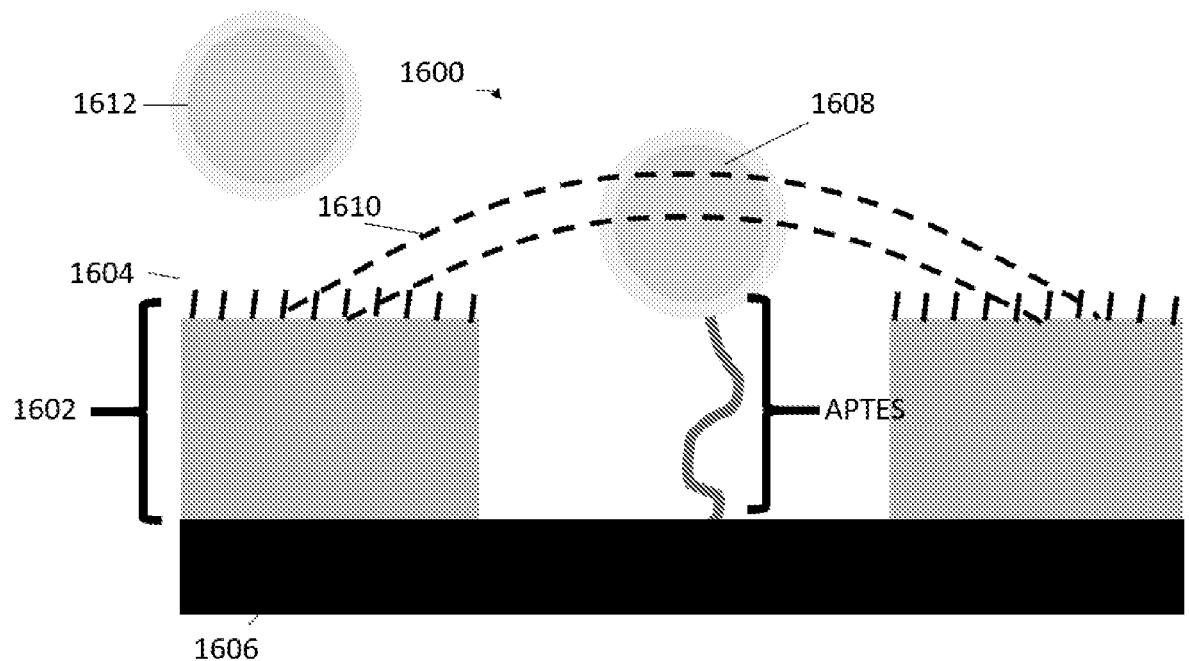
FIG. 16 is a cross sectional representation of a detection device of a biosensor having electrodes made of gold.

FIG. 16 is a cross sectional representation of a detection device of a biosensor having electrodes made of gold. Detection device 1600 comprises a substrate 1606 and gold electrodes 1602, which are coated with MUA 1604, which can prevent gold nanoparticles from settling on the surface of the electrodes via metallic bonding. An immobilized nanoparticle 1608 and electric field lines 1610 are also shown.

Aluminum electrodes have the benefit of having a naturally occurring aluminum oxide layer. Aluminum oxide is an excellent dielectric increasing the capacitive character of our design. This is preferable in some embodiments because the primary cause of impedance change detected is a change in capacitance from the addition of gold nanoparticles. Gold electrodes are generally far more chemically stable. Its noble metal features allow for less corrosion and unwanted chemical reactions in buffer and salt solutions. Gold does not react with most biological molecules making it useful for sensing these types of molecules. While aluminum electrodes are easier and more reliable to fabricate, gold electrodes are much more resistant to corrosion and have greater biocompatibility. Another benefit for gold electrodes is their affinity for molecules with thiol groups. This allows for surface modifications of the electrodes themselves after microfabrication.

In an embodiment, one or more surfaces of the electrodes may be modified using a pacifying self-assembled monolayer. A purpose of this monolayer is to have a non-reactive, inert layer covering the electrodes to block unwanted binding and other interactions with the electrode surface. In an embodiment, the layer may be MUA. The monolayer may reduce corrosion of the electrodes as a result of the presence of an added solution and/or sample under investigation. Also, gold nanoparticles have a tendency to aggregate or clump together. Aggregation is a source of error, since it can cause non-uniform binding on the surface. Gold nanoparticle diameters naturally vary through random error and aggregation, which has a significant effect on its capacitance. To prevent clumping of gold nanoparticles on the electrodes, in an embodiment, a self-assembled monolayer on the electrodes may be used. The addition of an extra layer over the gold interdigitated electrodes leads to little to no change in the impedance magnitude. This is favorable, since a massive change in impedance magnitude from the self-assembled monolayer could overshadow changes in gold nanoparticle concentration. The capacitive effect of the layer, however, is noticeable, in a downward shift in the phase component of the impedance.

The formation of the layer may be accomplished by modifying the gold interdigitated electrodes with MUA via its thiol group. Thiol groups have a high affinity for gold. In an embodiment, the electrodes may be coated with mercaptoundecanoic acid (MUA). In an example, a solution of MUA (e.g. a 50 μL solution of 1 mM MUA) may be brought into contact with the interdigitated electrode for several hours to allow for adsorption of the MUA to the surface of the electrodes. This creates a layer of a long-chain alkane with a carboxy-functional group on the end. This functional group helps to prevent molecules from chemically binding to the surface of the electrodes. The electrodes may then be modified by APTES as a chemical anchor and modifier to provide an "anchor" to easily bind other components such as MREs. In an embodiment, the substrate may be modified or coated with APTES to provide or facilitate attachment of the MREs to the substrate. It is to be appreciated that APTES is only one anchor and/or modifier. Other anchors and/or modifiers may be used.

Impedance Measurements

The detection device of the biosensor may be configured for measuring the impedance across the first and second electrodes at one or more frequencies. The one or more frequencies may be in any suitable range of frequencies. The impedance may be measured at a set of specific frequencies or swept across a range of frequencies, for example using impedance spectroscopy. In an embodiment, the frequencies may be, without limitation, within one of the approximate ranges of 50 kHz to 500 kHz or 1 kHz to 100 kHz. Thus an alternating current (AC) voltage, for example at or below 100 mV, to avoid electrochemical reactions, may be utilized for measuring impedance values at various frequencies.

In an embodiment, a biosensor of the present disclosure provides a high degree of sensitivity by only measuring the impedance across its electrodes at one, two or some other small number of frequencies. The number of different frequencies may be 1-10, 2-5, 3, 4 or any other suitable number.

In general, for a specific biosensor in combination with a specific target biomolecule, there is a frequency for a single impedance measurement that provides the greatest sensitivity, meaning the greatest measured change in impedance as a function of frequency. This frequency or frequency range may be determined through routine experimentation.

More specifically, the ideal frequency or frequencies for impedance measurement can vary between testing conditions, such as electrode dimensions, and the particular target. Generally, the ideal testing frequency is determined by first measuring impedance over a range of frequencies and determining the frequency at which there is the largest measurable change in impedance. This is the set frequency for future tests of the same nature.

In general, biological samples to be tested may have high ion concentrations. This factor may be taken into consideration when designing a sensor for a particular application. In some circumstances, biological conditions have ionic concentrations that are too high for detection to work properly. After exposure to the biological sample, the sample may be removed and a "measurement buffer" with the appropriate, known, ionic concentration may be added for the impedance measurement to take place. Having a predictable and known background ion concentration for impedance measurement is, in at least some embodiments, vital for measuring the impedance changes caused by bound nanoparticles.

Example Target Biomolecules

The biosensor and method according to the present disclosure may be used to detect many different types of biomolecules. Table 1 below provides a non-exhaustive list of example targets:

TABLE 1

List of Example Targets

| Metabolite | Normal Concentration in Blood (μM) | Normal Concentration in Urine (μmol/mmol creatinine) |
|---|---|---|
| Asymmetric Dimethylarginine (ADMA) | 0.41-0.79 | 2.50-3.34 |
| Aldosterone | 0.000008-0.000044 | 0.006-0.014 |
| Aminoadipic acid | 0.0-5.0 | 3.4-11.2 |
| Beta-Hydroxybutyrate | 40-80 | 23.6-41.0 |
| Betaine | 20.0-144.0 | 6.4-92.7 |
| Billirubin | 5.0-21.0 | 0.0019-0.21 |
| Carnosine | 5.54-7.54 | 0.8-6.2 |
| Choline | 8.7-12.5 | 1.4-6.1 |
| Creatinine | 50.0-80.0 | 800-1100 |
| Estradiol | 0.0-0.00018 (male) | 0.00034-0.00084 (female) |
| Folate | 0.011-0.036 | 0.000013-0.0026 |
| Formate | 23.9-219.5 | 8.55-32.23 |
| Glucose | 4070-4810 | 11.98-39.62 |
| Glutamate | 44.0-76.0 | 3.3-18.4 |
| Glutamine | 581-709 | 9.0-33.0 |
| Glycerol | 34.0-52.0 | 0.12-0.73 |
| Homocysteine | 7.0-11.0 | 0.48-3.42 |
| HPHPA | (unknown) | 0.00-90.0 |
| Indoxylsulfate | 9.8-18.2 | 14.48-25.0 |
| Lactate | 600-2300 | 0.0-0.25 |
| Leucine | 127.0-187.0 | 1.5-4.5 |
| Neopterin | 0.0109-0.0191 | 0.13-0.29 |
| Phenylalanine | 56.0-74.0 | 2.63-6.37 |
| Pyruvate | 38.0-88.0 | 0.54-8.67 |
| Taurine | 102.0-222.0 | 21.1-105.0 |
| Testosterone | 0.009-0.03472 (male) 0.00052-0.00243 (female) | 0.88-1.26 (male) 0.0000-0.0002 (female) |
| TMAO | 17.4-58.2 | 0.00-151.0 |
| Tyrosine | 57.0-87.0 | 4.3-13.3 |
| Uric Acid | 242.0-362.0 | 119.0-294.0 |
| Vitamin D | 0.063-0.221 | 0 |

Table 2 below provides a non-exhaustive list of various biomarkers approved for identifying disease states:

TABLE 2

List of Example Biomarkers

| Metabolite Marker | Approved Uses | Disease Associations |
|---|---|---|
| Asymmetric Dimethylarginine (ADMA) | Likelihood of future coronary events, especially in patients with renal failure. | Chronic heart failure, chronic kidney disease, chronic renal failure, coronary artery ectasia, increased risk for future cardiac events, insulin resistance, metabolic syndrome, mortality prediction, pulmonary arterial hypertension, stroke, vascular endothelial impairment, waist size |
| Aldosterone | Measured with Renin and cortisol to diagnose primary hyperaldosteronism (Conn syndrome), Secondary hyperaldosteronism and Adrenal insufficiency (Addison's disease) which causes changes blood pressure. | Chronic kidney disease, cardiovascular disease, microalbuminuria, vascular disease, mortality prediction |

TABLE 2-continued

List of Example Biomarkers

| Metabolite Marker | Approved Uses | Disease Associations |
|---|---|---|
| Aminoadipic acid | Tested in amino acid test aid in evaluation of endocrine disorders, liver diseases, muscle diseases, neoplastic diseases, neurological disorders, nutritional disturbances, renal failure, and burns. | Diabetes, oxidative stress |
| Beta-Hydroxybutyrate | Monitoring therapy for diabetic ketoacidosis investigating the differential diagnosis of any patient presenting to the emergency room with hypoglycemia, acidosis, suspected alcohol ingestion, or an unexplained increase in the anion gap In pediatric patients, the presence or absence of ketonemia/uria is an essential component in the differential diagnosis of inborn errors of metabolism Serum beta-hydroxybutyrate is a key parameter monitored during controlled 24-hour fasts | Downs syndrome, diabetes mellitus, diabetic ketoacidosis, ketosis, vitamin B12 deficiency, Reye syndrome, pulmonary infections, viral gastroenteritis, von Gierke disease, hyperthyroidism, pregnancy, heat stroke, ethanol consumption/alcoholism, malnutrition, high fat diet, pyruvate dehydrogenase deficiency, respiratory chain defects, propionic acidemia, methylmalonic acidemia, multiple carboxylase deficiency, 3-methylcrotonyl-CoA carboxylase deficiency, glyceroluria, MSUD, glutaric aciduria type I, isovaleric acidemia, MAD deficiency, beta-ketothiolase deficiency, 2-ketoadipic academia, mitochondria) SCHAD, fatty acid oxidation deficiency |
| Betaine | | Cardiovascular disease, colorectal adenoma, CVD/atherosclerosis, pre-eclampsia |
| Billirubin | bilirubin is measured to diagnose and/or monitor liver diseases, such as cirrhosis, hepatitis, or gallstones. It is also used to evaluate people with sickle cell disease or other causes of hemolytic anemia. In newborns with jaundice, bilirubin is mea | Billiary stricture, Crohn's disease, hemolytic anemia, liver disease, pancreatic cancer, preeclampsia, increased risk for coronary artery disease, atherosclerosis, heart attack, cardiac syndrome X, appendicitis |
| Carnosine | tested in amino acid test aid in evaluation of endocrine disorders, liver diseases, muscle diseases, neoplastic diseases, neurological disorders, nutritional disturbances, renal failure, and burns | Alzheimer's disease, diabetic nephropathy, diabetic progression, diabetic retinopathy |
| Choline | prognosis in patients with chest discomfort | Breast cancer, breast cancer recurrence, breast cancer risk, cardiovascular disease, celiac disease, colorectal cancer, prostate cancer, CVD/atherosclerosis, neural tube defects, fatty liver disease, hypertension, celiac disease, renal carcinoma |
| Creatinine | calculate the estimated glomerular filtration rate (eGFR) used with a variety of other urine tests as a correction factor part of a group of tests used to evaluate the function of the body's major organs | Atherosclerosis, autism, celiac disease, chronic obstructive pulmonary disease, glycerol kinase deficiency, multiple sclerosis, pancreatic cancer, stroke |
| Estradiol | measured with estrogen and estrone to investigate abnormal menstrual cycles, fetal-placental status during early stages of pregnancy and to evaluate feminization. | increased risk for breast cancer, hip fracture, dementia, fatty liver disease, peripheral arterial disease |
| Folate | Evaluate nutritional status Diagnose one cause of anemia or neuropathy | Acute coronary events, late life depression, ischaemic stroke, stroke, neural tube defects, peripheral vascular disease, Alzheimer's, risk of cataract development |

TABLE 2-continued

List of Example Biomarkers

| Metabolite Marker | Approved Uses | Disease Associations |
| --- | --- | --- |
| Formate | | Asthma, breast cancer, chronic obstructive pulmonary disease, stroke, breast cancer recurrence, stroke, lupus, lung cancer |
| Glucose | Screen for, diagnose, and monitor high blood glucose (hyperglycemia) or low blood glucose (hypoglycemia), diabetes, and pre-diabetes | Asthma, breast cancer, celiac disease, colorectal cancer, diabetes, lung cancer, hyper/hypoglycemia pancreatic cancer, Huntington's disease, chronic liver failure, various cancers, fatty liver disease |
| Glutamate | Evaluating patients with possible inborn errors of metabolism. | Breast cancer, celiac disease, depression, breast cancer recurrence, outcome from stroke/ischemia, autism severity, risk for type I diabetes, diabetes, schizophrenia, psychoses, ulcerative colitis, pancreatic cancer, survival from trauma, ALS |
| Glutamine | Evaluating patients with possible inborn errors of metabolism. | Celiac disease, depression, stroke, ulcerative colitis, diabetes, lupus, lung cancer, fatty liver disease, ALS, stroke, pancreatic cancer |
| Glycerol | | Glycerol kinase deficiency, preeclampsia, lupus, trauma, liver cancer, Uremia, Glycerol kinase deficiency, fructose-1,6, phosphatase deficiency |
| Homocysteine | Determine if folate-deficient or B12-deficient Diagnose homocystinurina Identify increased risk of heart attack or stroke | Chronic kidney disease, coronary artery ectasia, late life depression, microalbuminuria, stroke, vitiligo, CVD/atherosclerosis and ischemia,, chronic kidney disease, hip fracture, late-life depression, Alzheimer's disease, coronary artery disease mortality |
| HPHPA | | Autism |
| Indoxylsulfate | Presence in urine can indicate Hartnup disease, intestinal obstruction, gastric cancer, hypochlorhydria, biliary obstruction, and malabsorptive conditions such as sprue and blind-loop syndrome. | Atherosclerosis, celiac disease, chronic cyclosporine nephrotoxicity, schizophrenia, autism, psychoses, depression, seizures, and in chronic fatigue syndrome |
| Lactate | Lack of oxygen (hypoxia) or other conditions that cause excess production or insufficient clearing of lactate from the blood Diagnosing and monitoring patients with lactic acidosis | Asthma, celiac disease, colorectal cancer, esophageal cancer, lung cancer, pancreatic cancer, rheumatoid arthritis, react cancer recurrence, critical illness mortality, burn mortality, neonatal morbidity, cancer metastatic risk, schizophrenia, colon cancer, trauma survival, stroke, renal carcinoma, infection, vitamin B deficiency, poor perfusion, or intestinal bacterial overgrowth, pyruvate dehydrogenase deficiency, glycogen storage diseases, disorders of fructose metabolism, severe trauma, short bowel syndrome, apnea, septicemia, seizures, cardiac insufficiency, diabetic ketoacidosis, Reye syndrome, lactic acidosis, pyruvate dehydrogenase deficiency, respiratory chain defects, Krebs acid cycle defects, gluconeogenesis defects, MAD deficiency, VLCAD deficiency, glutaric aciduria type I, multiple carboxylse deficiency, methylmalonic acidemia, isovlaeric acidemia, propionyl acidemia, oitrullinemia, glycerol kinase deficiency, HMG-CoA lyase deficiency, EMA aciduria |
| Leucine | evaluating patients with possible inborn errors of metabolism | Celiac disease, colorectal cancer, type II diabetes, esophageal cancer, pancreatic |

TABLE 2-continued

List of Example Biomarkers

| Metabolite Marker | Approved Uses | Disease Associations |
|---|---|---|
| | | cancer, diabetes, schizophrenia, colon cancer, celiac disease, pancreatic cancer |
| Neopterin | Infections<br>Autoimmune diseases: Rheumatoid Arthritis, Systemic Lupus, and Atopic Asthma<br>Malignant diseases<br>Psychiatric disorders Sleep-disordered breathing<br>Children with Autism Spectrum Disorders | Alzheimer's disease, atherosclerosis, breast cancer, colon carcinoma, Crohn's disease, dermatomyositis, hematological neoplasias, hepatocellular cancer, HIV infection, inflammatory bowel diseases, lung cancer, organ rejection after transplant, ovarian carcinoma, post-therapeutic tumor relapse, prostate cancer, rheumatoid arthritis, squamous cell carcinoma, ulcerative colitis, uterine cervix carcinoma, viral infection, Wegener's granulomatosis |
| Phenylalanine | Evaluating patients with possible inborn errors of metabolism. | Asthma, colorectal cancer, type II diabetes, maple syrup urine disease, phenylketonuria, diabetes, tardive dyskinesia, schizophrenia, colon cancer, celiac disease, lupus, kidney cancer, HIV infection, renal cell carcinoma, liver cancer |
| Pyruvate | Evaluating patients with possible inborn errors of metabolism. | ALS, celiac disease, stroke, lupus, stomach cancer, lung cancer, liver failure, stroke, ALS, celiac disease, liver disease, infection, 13 vitamin deficiency, poor perfusion, or intestinal bacterial overgrowth, pyruvate dehydrogenase deficiency, glycogen storage diseases, disorders of fructose metabolism, severe trauma, Short bowel syndrome, apnea, septicemia, seizures, cardiac insufficiency, diabetic ketoacidosis Reye syndrome, lactic acidosis, pyruvate dehydrogenase deficiency, respiratory chain defects, Krebs acid cycle defects, gluconeogenesis defects, MAD deficiency, VLCAD deficiency, glutaric aciduria type I, multiple carboxylse deficiency, methylmalonic acidemia, isovlaeric academia, propionyl academia, citrullinemia, glycerol kinase deficiency, HMG-CoA lyase deficiency, EMA aciduria |
| Taurine | Evaluating patients with possible inborn errors of metabolism. | Breast cancer, colorectal cancer, depression, preeclampsia, breast cancer, outcome from stroke/ischemia, risk of cataract development, reduced risk of obesity, breast cancer outcome, colon cancer, colitis, fatty liver disease |
| Testosterone | In males: erectile dysfunction, infertility, premature or delayed puberty<br>In females: virilization, inability to get pregnant, marker for polycystic ovary syndrome (PCOS) | peripheral arterial disease, breast cancer, cardiovascular disease, liver cancer, Alzheimer's disease, hip fracture, anemia, atherosclerosis |
| TMAO | | Pancreatic cancer, CVD/atherosclerosis |
| Tyrosine | Evaluating patients with possible inborn errors of metabolism. | Asthma, type II diabetes, esophageal cancer, maple syrup urine disease, diabetes, breast cancer recurrence, schizophrenia, celiac disease, lupus, leukemia, liver cancer |
| Uric Acid | Diagnose/monitor gout<br>Monitor uric acid levels when undergoing chemotherapy or radiation treatment<br>Diagnose the cause of kidney stones | Type II diabetes, microalbuminuria, multiple sclerosis, Parkinson's disease, reduced risk of Parkinson's disease, cancer mortality, brain ischemia, cardiovascular disease, coronary heart disease, hypertension |
| Vitamin D | Vitamin D deficiency | All-cause mortality, asthma, cardiovas4ilar mortality, non- Alzheimer dementias, preeclampsia, diabetes risk, stroke, sudden cardiac death, knee |

TABLE 2-continued

List of Example Biomarkers

| Metabolite Marker | Approved Uses | Disease Associations |
|---|---|---|
| | | osteoarthritis, rheumatoid arthritis, Parkinson's, Alzheimer's |

Aspects of the present disclosure may be implemented on any suitable apparatus or apparatuses, which may include one or more computers and/or computer related components. Further, aspects of the present disclosure may be implemented in software, hardware, or a combination thereof. Hardware may include one or more of analog circuitry, digital circuitry, and electronics.

Figure 17:
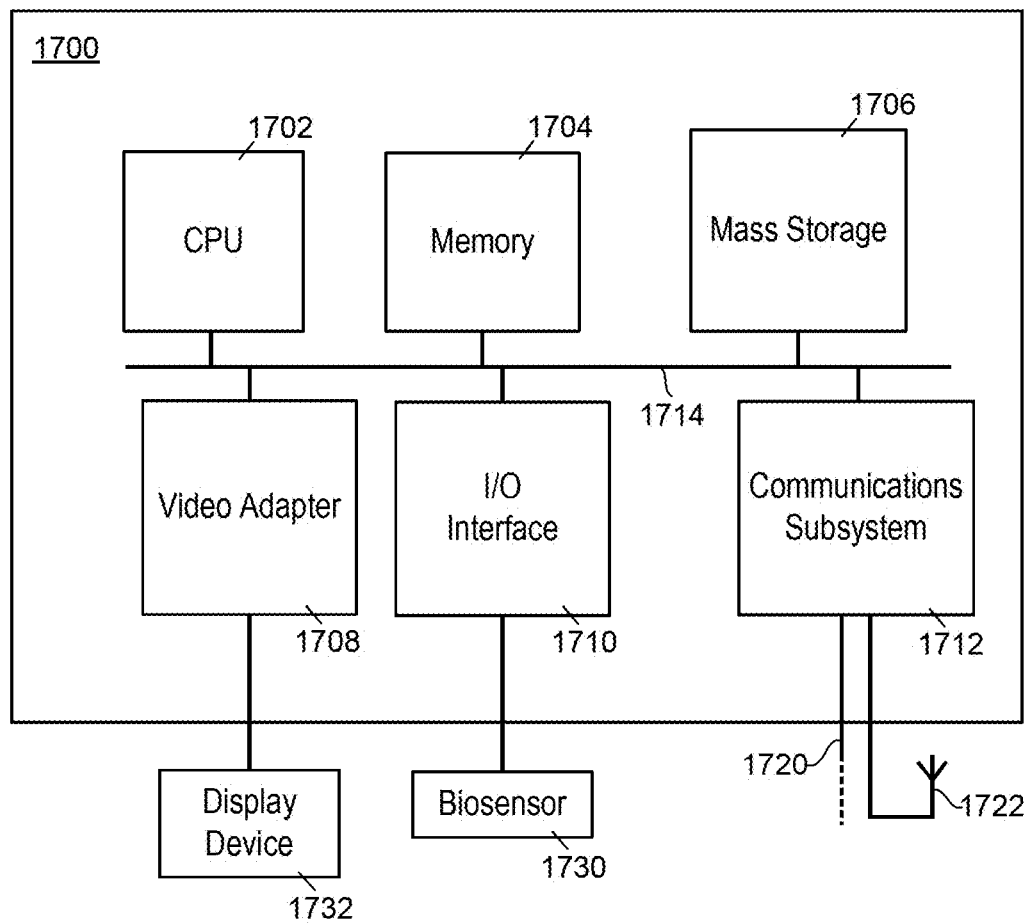
FIG. 17 is a block diagram of an example electronic device that may be used in implementing one or more aspects or components of an embodiment.

FIG. 17 is a block diagram of an example electronic device 1700 that may be used in implementing one or more aspects or components of an embodiment according to the present disclosure.

In an embodiment, electronic device 1700 may be used to provide control and/or processing capabilities in relation to a biosensor or sensing method according to the present disclosure. FIG. 17 shows electronic device 1700 communicatively coupled to a biosensor 1730.

The electronic device 1700 may include one or more of a central processing unit (CPU) 1702, memory 1704, a mass storage device 1706, a video adapter 1708, an input/output (I/O) interface 1710, and a communications subsystem 1712. One or more of the components or subsystems of electronic device 1700 may be interconnected by way of one or more buses 1714 or in any other suitable manner.

The bus 1714 may be one or more of any type of several bus architectures including a memory bus, storage bus, memory controller bus, peripheral bus, or the like. The CPU 1702 may comprise any type of electronic data processor. The memory 1704 may comprise any type of system memory such as dynamic random access memory (DRAM), static random access memory (SRAM), synchronous DRAM (SDRAM), read-only memory (ROM), a combination thereof, or the like. In an embodiment, the memory may include ROM for use at boot-up, and DRAM for program and data storage for use while executing programs.

The mass storage device 1706 may comprise any type of storage device configured to store data, programs, and other information and to make the data, programs, and other information accessible via the bus 1714. The mass storage device 1706 may comprise one or more of a solid state drive, hard disk drive, a magnetic disk drive, an optical disk drive, or the like. In some embodiments, data, programs, or other information may be stored remotely, for example in the cloud. Electronic device 1700 may send or receive information to the remote storage in any suitable way, including via communications subsystem 1712 over a network or other data communication medium.

The video adapter 1708 may provide an interface to couple a display device 1732 to the electronic device 1700 for displaying information, such as information relating to sensing or measurements performed using biosensor 1730. Electronic device 1700 may be configured to display information on display device 1732 that is responsive to changes in the electrical impedance across the first and second electrodes of the detection device of biosensor 1730. Further, electronic device 1700 may be configured to detect changes in the electrical impedance across the first and second electrodes using impedance spectroscopy.

The I/O interface 1710 may provide interfaces to couple one or more other devices, such as one or more biosensors 1730, to the electronic device 1700. The other devices may include but are not limited to one or more of a mobile device, a computing device, a sensor, and a server computer. Furthermore, additional or fewer interfaces may be utilized. For example, one or more serial interfaces such as Universal Serial Bus (USB) (not shown) may be provided. It is to be appreciated, however, that these peripherals and other devices are examples only. Other devices may be coupled or connected to the electronic device in addition to or in place of those shown and described. Furthermore, additional or fewer interfaces may be utilized. For example, one or more serial interfaces such as Universal Serial Bus (USB) (not shown) may be provided.

A communications subsystem 1712 may be provided for one or both of transmitting and receiving signals. Communications subsystems may include any component or collection of components for enabling communications over one or more wired and wireless interfaces. These interfaces may include but are not limited to USB, Ethernet, high-definition multimedia interface (HDMI), Firewire (e.g. IEEE 1394), Thunderbolt™, WiFi™ (e.g. IEEE 802.11), WMAX (e.g. IEEE 802.16), Bluetooth™, or Near-field communications (NFC), as well as GPRS, UMTS, LTE, LTE-A, dedicated short range communication (DSRC), and IEEE 802.11. Communication subsystem 1712 may include one or more ports or other components 1720 for one or more wired connections. Additionally or alternatively, communication subsystem 1712 may include one or more transmitters (not shown), receivers (not shown), and/or antenna elements 1722.

A biosensor according to the present disclosure may communicate wirelessly with a mobile device or other computing device allowing for control and data processing to be done on the mobile device or other device. Measured target concentrations or any other data based on measurements may be compared to data stored in existing databases, for example to identify, predict, and/or monitor diseases or other conditions.

The electronic device 1700 of FIG. 17 is merely an example and is not meant to be limiting. Various embodiments may utilize some or all of the components shown or described. Some embodiments may use other components not shown or described but known to persons skilled in the art. Also, the boundary of the electronic device 1700 in FIG. 17 is not meant to be limiting, meaning some components may be external to electronic device 1700 whereas other components may be internal.

In an embodiment, biosensor 1730 may be packaged together with electronic device 1700 as a single unit. The display device 1732 may also be included in the package. In an embodiment, the single unit may be adapted as a hand held unit. Biosensor 1730 may include a receptacle for engaging removable sensing cartridges or strips (not shown). For instance, an unused sensing cartridge may be inserted into the sensor, a sample deposited onto the cartridge, sensing performed, and the used cartridge may then be removed and discarded.

Furthermore, the teachings of the present disclosure may be implemented at or performed by any network element or combination of network elements. A network element may be a network side electronic device, such as a server, or a user side electronic device, such as mobile device or other personal electronic device. These network side and user side devices are only examples and are not intended to be limiting.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented in software, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a computer processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

To gain a better understanding of the teachings and disclosures described herein, the following examples are set forth. It should be understood that these examples are for illustrative purposes only. Therefore, they are not intended to limit the scope of the present disclosure in any way.

EXAMPLES

Example 1—Simulations of Interdiditated Electrode Interactions with Gold Nanoparticles for Impedance-Based Biosensing Applications Abstract In this paper, we describe a point-of-care biosensor design. The uniqueness of our design is in its capability for detecting a wide variety of target biomolecules and the simplicity of nanoparticle enhanced electrical detection. The electrical properties of interdigitated electrodes (IDEs) and the mechanism for gold nanoparticle-enhanced impedance-based biosensor systems based on these electrodes are simulated using COMSOL Multiphysics software. Understanding these properties and how they can be affected is vital in designing effective biosensor devices. Simulations were used to show electrical screening develop over time for IDEs in a salt solution, as well as the electric field between individual digits of electrodes. Using these simulations, it was observed that gold nanoparticles bound closely to IDEs can lower the electric field magnitude between the digits of the electrode. The simulations are also shown to be a useful design tool in optimizing sensor function. Various different conditions, such as electrode dimensions and background ion concentrations, are shown to have a significant impact on the simulations.

Introduction

Biosensor devices hold great potential for various applications in detecting the growth of cells and bacteria [1,2], detecting toxins [3], and detecting disease and monitoring disease progression [4,5]. Different detection designs based on optical, mechanical and electrochemical methods have been proposed [6-8]. These designs each have their own advantages and disadvantages. Electrical and electrochemical detection techniques are particularly well suited for quick and simple detection [8].

Although individual methods can vary, all electrical and electrochemical biosensors work by measuring changes in electrical properties caused by the presence of specific biological targets. These changes can be caused by interference in electric fields [9], chemical reactions [10], or from conductive labels [8]. Electrodes (usually gold) are used as interfaces both in applying electric fields to the tested samples and as a method of transmitting and measuring electrical detection signals. The types of measured electrical signal vary as well depending on the application, and can be simple impedance or resistance measurements [11], capacitance measurements [9], or electrical spectroscopy, taking measurements over a range of frequencies [10].

Beyond being a simple interface, the properties of the electrodes used in electrical and electrochemical biosensors can have a significant impact on the function and effectiveness of the resulting biosensor system. One prominent example of this is the use of interdigitated electrodes (IDEs) in biosensor systems. IDEs consist of two interlocking, but separated metal plates, with each having a number of individual digits which overlap with those of the other section (see FIG. 19), essentially creating the same structure as microfabricated capacitors. Applying a voltage to IDEs, either AC or DC, creates an electric field between the digits. This electric field can be disrupted and altered by the presence of specific target biomolecules, cells, or electrically active labels and the resulting change can then be measured. It has therefore been possible use IDEs in a number of highly sensitive biosensing applications [1, 2, 12-15]. Nearly all biosensor applications of IDEs use gold as the electrode material, due to its biocompatibility.

Several key dimensions of IDEs can have a great impact on what particular application they are best suited for and how well they perform. Digit width and digit spacing are of particular importance, with smaller interdigit spacing generally resulting in more sensitive detection. Dimensions in the range of several micrometers (for both the digit width and spacing) have been shown to be effective for the detection of cells and bacteria [1], whereas electrodes with sub-micron dimensions have been made which are sensitive enough to detect DNA hybridization [13]. With such large differences in the dimensions required for different applications, the proper design and optimization of IDEs is essential for their use in effective biosensors.

Because a variety of different parameters and dimensions play a part in the resulting function of an IDE, it becomes impractical to design, manufacture and test all possible designs for a particular application. It is by far more practical to simulate the electric field and potential of IDEs using models. Simulations for the optimization of IDE dimensions for specific applications have previously been carried out. However, these simulations are specific to one particular application, such as for the detection of bacteria [1].

The specific purpose of the simulations presented in this paper is to find the optimum IDE dimensions and testing conditions for a gold nanoparticle enhanced impedance-based biosensor. This method uses aptamers or binding proteins, depending on the target biomolecule, to bind to specific biomolecules and allow for a connection between an electrode surface and modified gold nanoparticles. An example of this with antibodies is shown in FIG. 20 Aptamers are single strands of DNA or polymers with structures that can be designed to bind specifically to target biomolecules [16-19]. In the case of the design presented here, detection is achieved by measuring changes in impedance caused by these attached gold nanoparticles. The presence of bound nanoparticles above the electrodes disrupts the electric field around the electrodes leading to decreased measured impedance. Initial experiments have shown that this method is effective for detecting a variety of target biomolecules, however, optimization of both the electrode dimensions and testing conditions is still required to create a fully realized biosensor device using this technique.

As mentioned previously, a number of different factors contribute to the exact conditions required for optimal detection. In the case of impedance-based detection, the most important factor is the electric field generated at the electrode and how this can be best influenced for effective detection. These factors include the digit width, spacing and height in the IDE, applied voltage to the electrode and the particular background solution used for testing. Since, as in many biosensor applications, measurement here takes place in an aqueous environment, it is very important that this background solution be controlled. This is so that the solution does not interfere with measurements, does not interfere with the target biomolecule or recognition elements, and does not interfere negatively with the electrode. Some interference with the electric field in the system is actually beneficial in making a more sensitive biosensor as the ionic concentration of a background solution can establish an electrical screening layer that, with the right design, can isolate the electric field to only the region above the electrode where binding and detection occurs, increasing sensitivity.

The goal of this article is to use COMSOL Multiphysics simulations to show the effect of using gold nanoparticles on IDE systems for impedance-based biosensing techniques. Furthermore, these simulations can be used to find optimal design conditions to achieve the highest sensitivity.

COSMOL Simulations

A simulation for the electrical properties of IDEs was carried out using COMSOL Multiphysics software. This finite element analysis software was used to model various geometries and conditions for IDEs and is able to display several electrical properties of such systems, including time dependent properties, such as effects of changing ion concentrations.

For simulations of electrical screening above IDEs, a Nernst-Poisson method was used. The overall charge distribution of the system is determined by the Poisson equation:

$$\nabla^2 \phi = -\frac{\rho}{\varepsilon} \qquad (1)$$

where $\phi$ is the electrical potential of the system, $\varepsilon$ is the electric permittivity of the solution and $\rho$ is the charge density caused by the ions in solution. The charge density is also related to the concentration of each type of ion in the solution:

$$\rho = eN_A \Sigma c_i z_i \qquad (2)$$

here the concentration of each ion ($c_i$) refers to the concentration as a function of location in the system, e is the elementary charge, $N_A$ is Avogadro's number and $z_i$ is the charge number (+1 or −1 for singly charged ions). Although the initial condition is for a uniform distribution of ions, they drift due to the applied voltage, causing variations in the overall concentration. These changes in the concentration ($c_i$) of the ions over time (t) is described by the Nernst-Planck equation:

$$\frac{\delta c_i}{\delta t} = \nabla \left[ D_i \nabla c_i - u c_i + \frac{D_i z_i e}{k_B T} c_i \left( \nabla \phi + \frac{\delta A}{\delta t} \right) \right] \qquad (3)$$

where D is the diffusivity of the ions, u is the fluid velocity, $k_B$ is the Boltzmann constant, T is the temperature and A is the magnetic vector potential. This equation is simplified in this case as the fluid itself does not move (u=0) and there are no magnetic fields (A=0):

$$\frac{\delta c_i}{\delta t} = \nabla \left[ D_i \nabla c_i + \frac{D_i z_i e}{k_B T} c_i \nabla \phi \right] \qquad (4)$$

which accounts for both ion migration due to the applied voltage at electrodes $$\left( \frac{D_i z_i e}{k_B T} c_i \nabla \phi \right),$$

and due to the concentration gradient created by this applied voltage ($D_i \nabla c_i$). Using these above equations, the COMSOL simulations are able to calculate the changes in concentrations of ions in IDE systems over time, as well as the resulting changes in electric field and electric potential distributions.

The actual model of the electrode system constructed in COMSOL consists of three basic parts: gold digits, a water background and ion concentrations. Taking advantage of the symmetry of the system along the axis of the digits, to add simplicity, these models are based on 2D planes, which are then extended into 3D. Therefore, all of the constructed digits and the water background were constructed as rectangles in one plane then extended to form the final model. To reduce complexity and to save time, only a small number of digits were modeled, and to avoid discrepancies, results for the simulations were taken only for the middle of these simulated sections. The same applies to the simulated gold nanoparticles. They consist of 2D circles placed above the electrodes, which become 3D when the simulation is extended. This results in "nano-cylinders" rather than perfect spheres. By limiting the depth of the extension however, these simulations can still study the effect of small amounts of gold (the nanoparticles) bound to the electrodes, while keeping the overall system simple, simulation mesh sizes fine enough for accurate results and still keep computation time reasonable. The material properties of the gold electrodes and surrounding water were added to the model for the various diffusion and electrical properties necessary. To model the ionic concentration, two entities (for positive and negative ions) were added with equal concentrations, for overall neutrality. The properties of the ions can be defined in the software, including diffusion constants, mobility and charge. The space charge density in the water is also defined using the varying concentrations of the ions. A free triangular mesh is used with this model. The maximum element size is specified to be 3.31 µm and the minimum is specified to be 18.8 nm. Along the surface of each digit and each gap the number of elements is fixed to 100. This in addition with a maximum element growth rate of 1.3 allows for a much greater mesh resolution around electrodes. Element size on other boundaries in the model is dictated by COMSOL's physics controlled mesh.

Electric Potential and Electric Screening Simulations

First, the electrical potential of IDEs was simulated using COMSOL software. This simulation also tracks the changing ion concentrations over time, making it possible to show the electric screening process over the electrode. Electric screening occurs when mobile ions in solution migrate due to the electric potential in the system and this mobile charge accumulation cancels out the electric field of the electrodes over a set distance as seen in FIGS. 21A-21D.

Since the final intent is for there to be an AC voltage applied to the electrodes, it is important to determine how quickly electrical screening is established. An AC signal is required to determine the impedance of the electrodes, as there are both capacitive and resistive contributions in an IDE system. FIGS. 21A-21D shows that with 0.1 V DC applied to electrodes and a KCl concentration of 150 µM in solution, full electrical screening is established within 50 µs. This establishment time will vary depending on the exact ion species used and the concentration. In these simulations, KCl is used because it has singly charged ions and well known migration constants for the simplest simulations for a salt solution. For this and other simulations presented here, an ion concentration of 150 µM is used. This value is based on early tests on fabricated electrodes with different buffer solutions. A solution with 150 µM KCl was found to give the optimal baseline impedance for these electrodes, with less concentrated making the resulting impedance too capacitive and much higher being too conductive as to just measure the resistance of the solution rather than the total impedance of the electrodes. In a later section, the effects of varying the ion concentration in simulations are investigated.

For screening when AC voltages are applies, it will be essential for full screening to be established in less time than the period of the AC voltage in order to have a consistent detection environment. Some simulations were done using a time dependent sinusoidal applied voltage at various frequencies. However, the evolution of these simulations over time provided no extra insight into the function of the sensor system. In this case, for example, an establishment time of 50 µs corresponds to a maximum AC frequency of 20 kHz. Since measurements in the final biosensor design are intended to be at lower frequencies (1-10 kHz), there is therefore enough time in each cycle for screening to be established.

For the simulations presented in this paper, only DC voltages are applied, and to ensure stable ion distributions, results are shown after an excessively long time period (100 ms). This ensures that any results are not influenced by transient properties of the environment. In actuality, it would take much less time for screening to be established.

Electric Field Simulations for Different Electrode Dimensions

These COMSOL simulations also make it possible to plot the electric field between individual electrode digits. This is particularly useful when trying to determine the ideal dimensions for digit width and spacing.

Figure 22A:
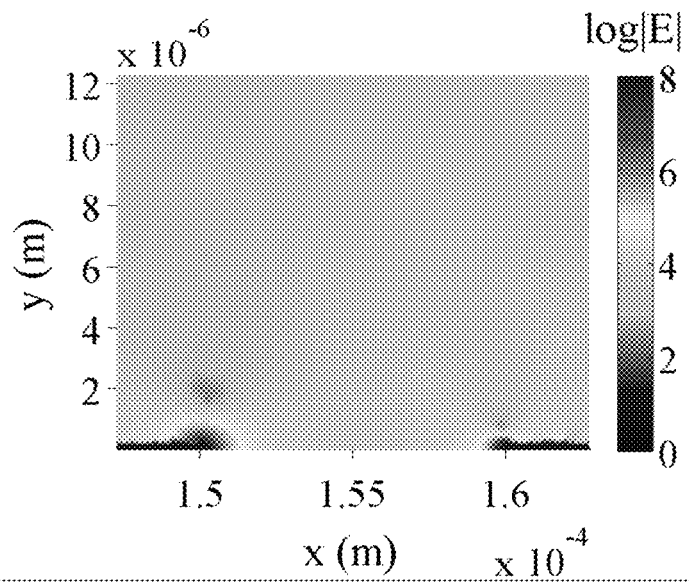
FIG. 22-A is a logarithmic plot of the electric field magnitude for 20 μm digits with 10 μm spacing.
Figure 22B:
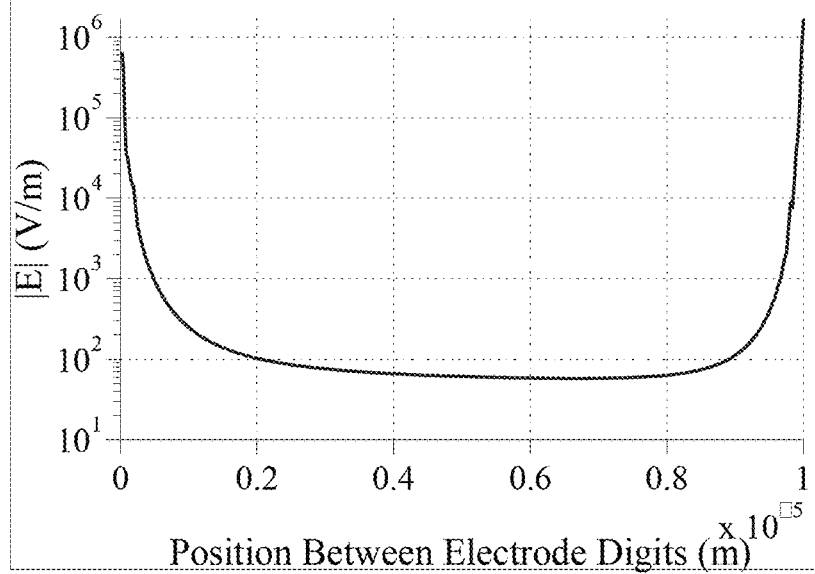
Figure 22C:
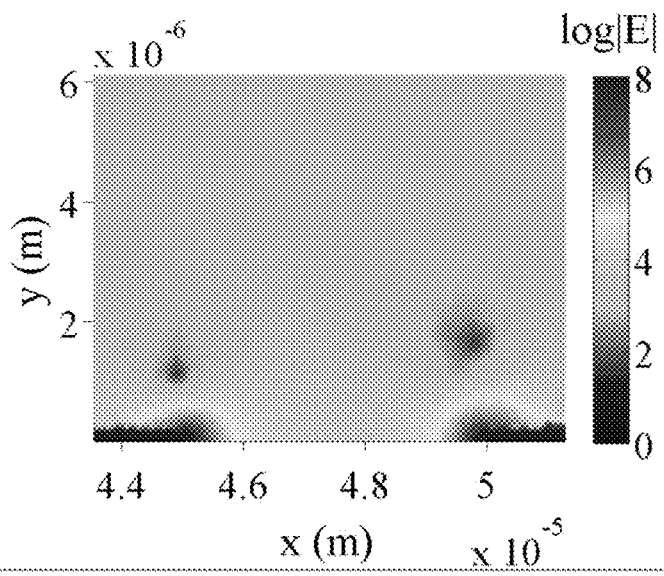
Figure 22D:
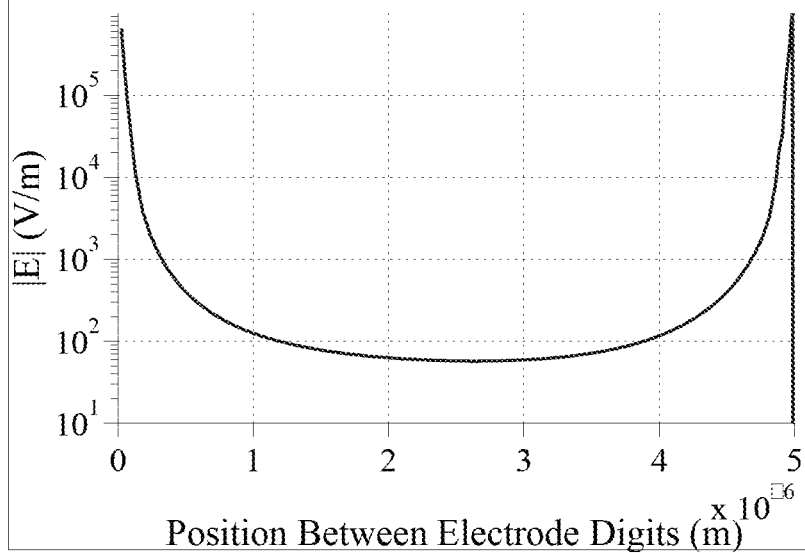
Figure 22E:
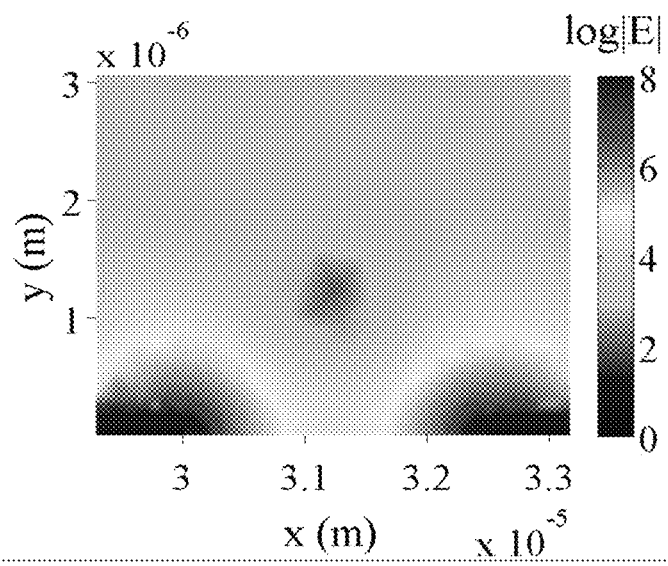
Figure 22F:
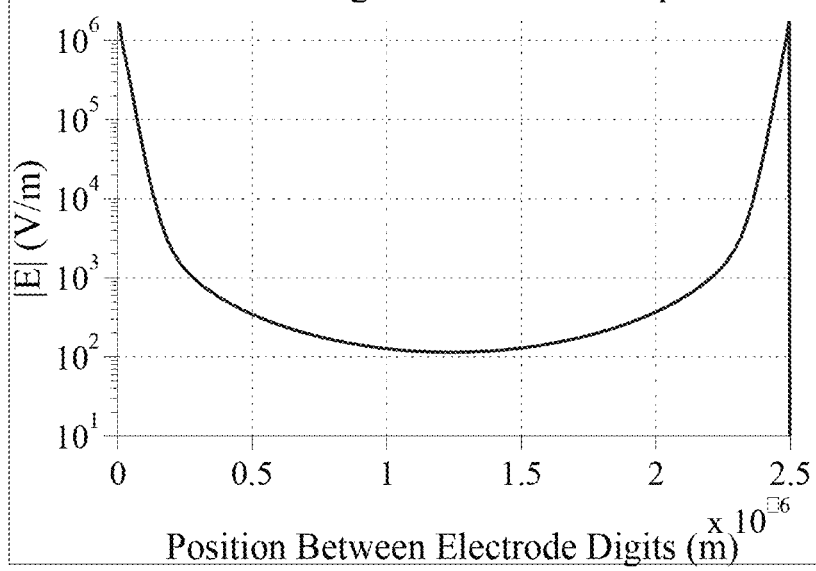

As seen in the simulations in FIGS. 22A-224F, as the spacing between digits is increased, the resulting electric field magnitude between them decreases. This electric field between digits is of particular importance when considering biosensor design, as disruptions in this electric field caused by specific binding of target biomolecules are the basis for many electrical biosensor designs. For example, bacteria on the surface of IDEs can disrupt this electric field, resulting in an increased impedance measured across the electrode [1]. In the same way, conducting tags can cause decreased impedance.

Impact of Gold Nanoparticles on Electric Field Magnitude

Figure 23:
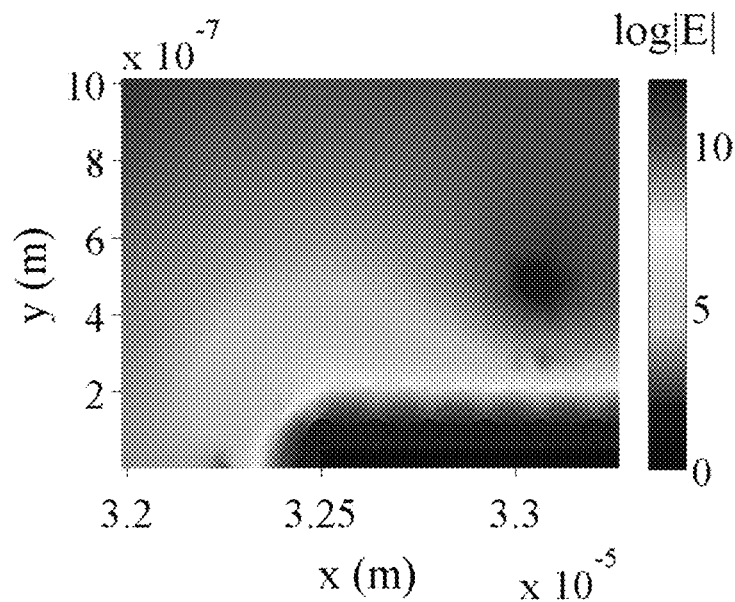
FIG. 23 is a logarithmic plot of the electric field magnitude of a of a 5 μm gold electrode with 60 nm GNPs placed 20 nm above the electrode surface after 0.1 s to completely establish electric screening.
Figure 24:
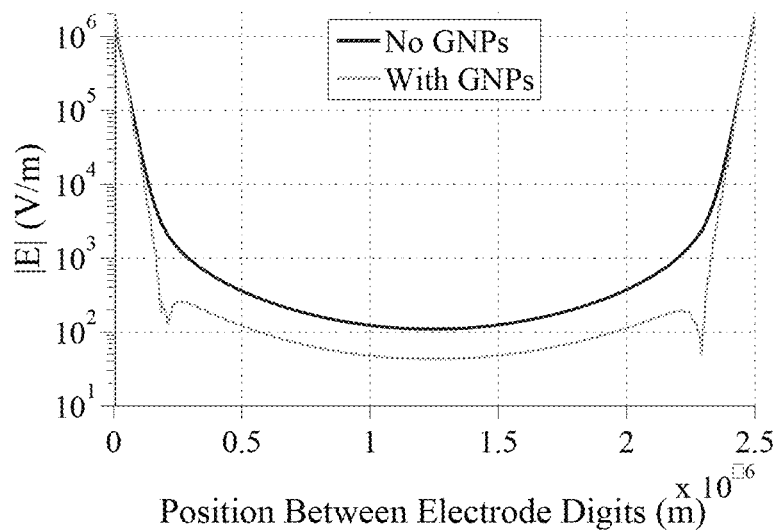
FIG. 24 is graph comparing the electric field magnitude between 5 μm digits with 2.5 μm spacing with and without 60 nm gold nanoparticles 20 nm above the electrodes.

The mechanism of detection in the proposed biosensor is for gold nanoparticles (GNPs) bound to the IDEs to affect the electric field of the system and result in a measurable impedance change. The effect of nanoparticles near the surface of the electrodes can be modeled in COMSOL as well by using gold circles and thinner "extensions" of the 2D plane. FIGS. 23-24 show that a distribution of GNPs placed above the surface of the gold digits can have an effect on the electric field measured directly between the electrode digits (measured from the middle of the of the sides of the digits). GNPs in general decrease the electric field magnitude directly between digits, which would result in a lower measured impedance for the overall electrode than a measurement taken without GNPs present.

FIGS. 23-24 show that GNPs on top of electrode digits do change the profile and decrease the electric field magnitude directly between digits. In the case shown here, at the middle of the interdigit space, there is a difference of about 66.5 V/m in the electric field magnitude. This demonstrates how gold nanoparticles can indeed be used to measure detection of targets bound to the surface of IDEs. Here, and in further simulations, 60 nm GNPs are used for bound nanoparticles. This diameter was chosen mainly to eventually compare simulation results with actual tests (for which 60 nm GNPs will be used) and to keep results in line with work that had been previously done with attaching biomolecules to 60 nm GNPs. In a later section, different sizes of GNPs will be simulated.

Many different factors contribute to the overall effectiveness of IDE systems for biosensor applications. By adjusting these various factors, the electric field-altering effect of GNPs can be improved to make the most effective sensor possible.

Impact of Ion Concentration on GNP Effect

In the previous simulation, the background of the electrode system was set as water containing 150 µM of KCl. However, changing this value can have a great impact on the entire system and the effect that GNPs have. Changing the ion concentration changes the amount of electrical screening around the electrodes and also the electrical properties (such as conductivity) between the electrodes.

Figure 25:
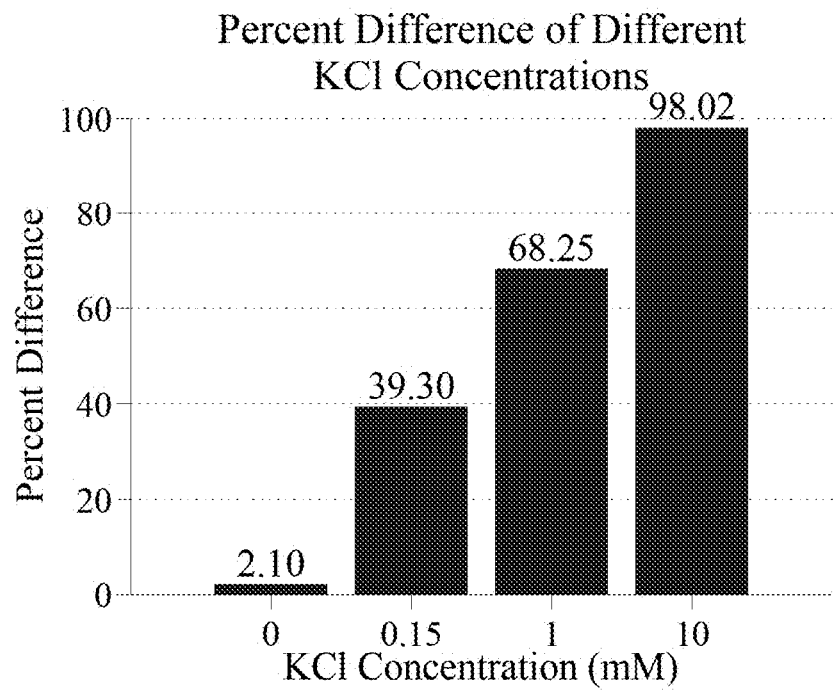
FIG. 25 is a plot showing the percent difference in the electric field magnitude at the center of the gap between electrodes digits different KCl ion concentrations.
Figure 26A:
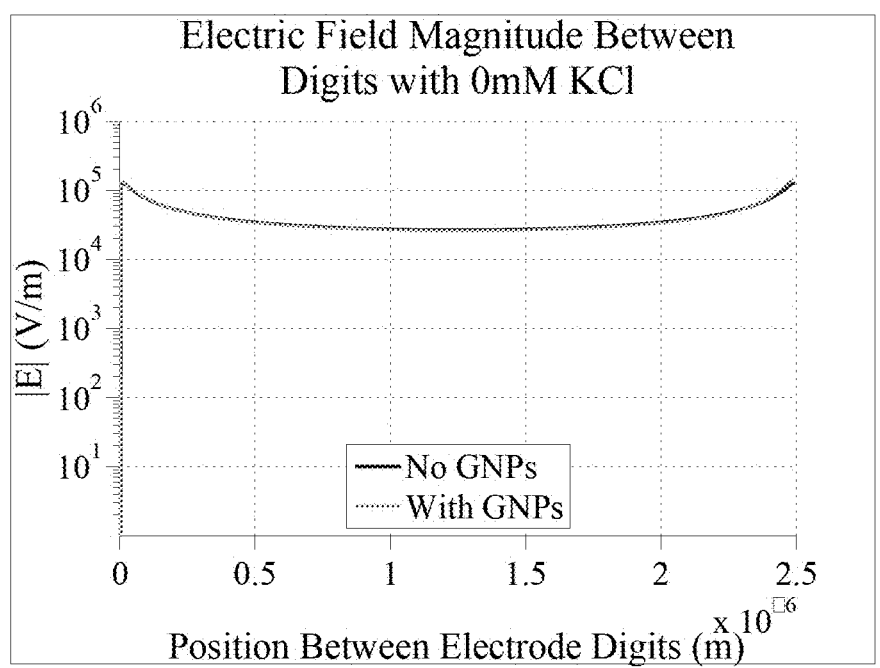
FIG. 26-A is a graph comparing the simulated electric field magnitude directly between two digits of electrodes with and without bound gold nanoparticles with a KCl concentration of 0 M in the solution in the electrodes.
Figure 26B:
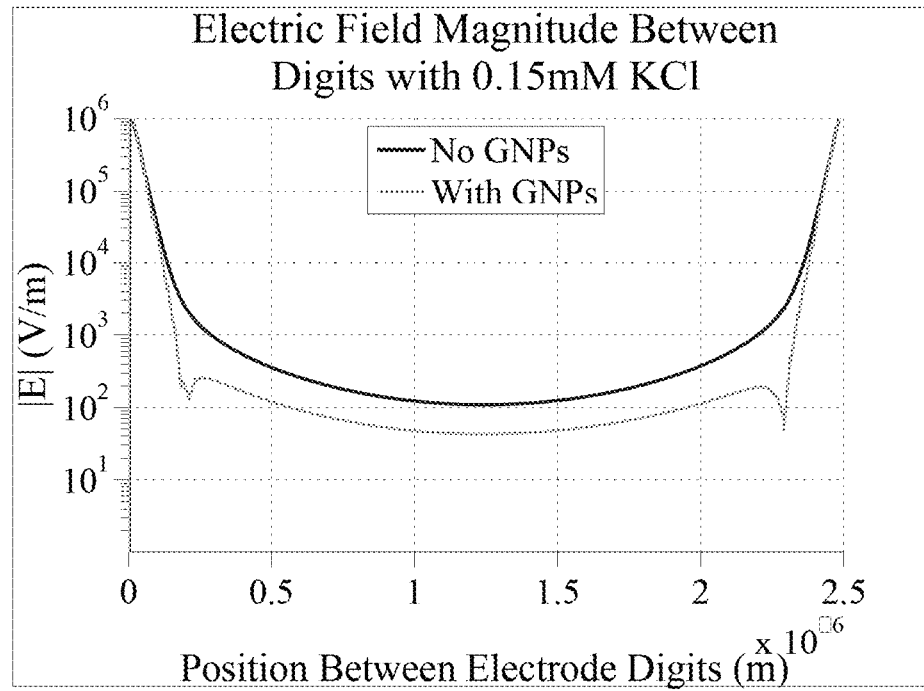
Figure 26C:
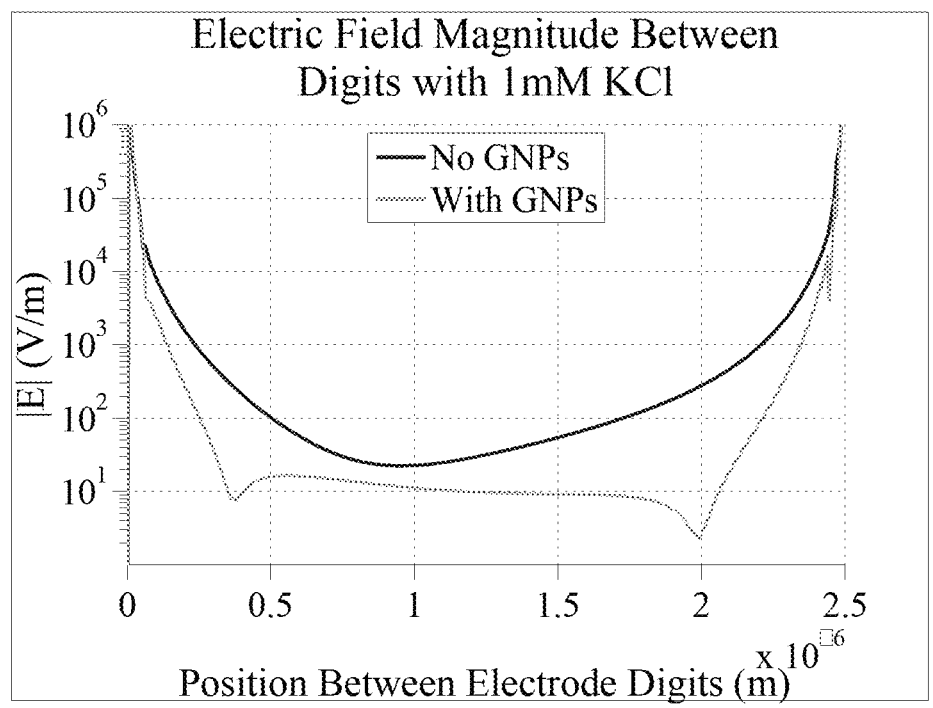
Figure 26D:
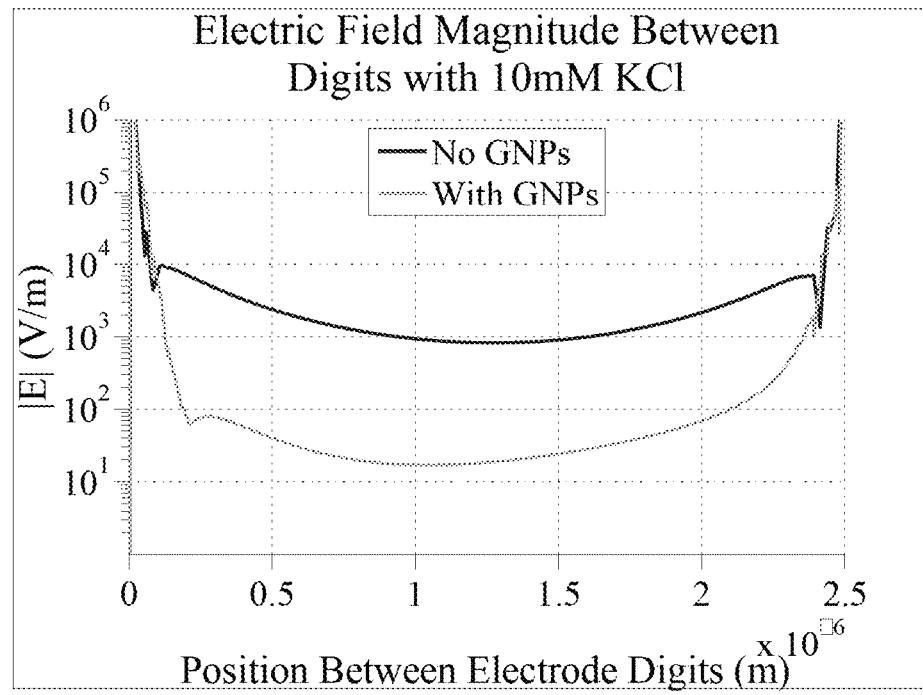

In order to investigate the effect of ion concentrations four different ion concentrations were simulated on electrodes with 5 µm digits with 2.5 µm electrode gaps. With no ions (just water) there is almost no difference in the electric field magnitude with and without GNPs. As the ion concentration is increased, both the electric field magnitude with and without bound GNPs decreases, but the electric field magnitude between electrodes with GNPs decreases by a greater amount. The percent difference between electric field magnitudes at the center of the gap (half way between electrode edges) for bare and GNP bound electrodes for different ion concentrations is shown in FIG. 25 and graphs of the electric field in these cases is shown in FIGS. 26A-26D.

The percent difference in the electric field magnitude increases from nearly 40% at 0.15 mM KCl to nearly 100% at 10 mM. Although the difference in electric field magnitude increases as ion concentration increases, there are practical limits to how high this can go. Ion concentrations that are too high could interfere with biological elements in the biosensor system and potentially disrupt GNP bonding. Additionally, increasing the ion concentration too high causes too much conduction between electrode digits, such that the conductivity of the ion solution overwhelms any effect of the nanoparticles on the impedance of the system. Therefore, it is necessary to find a balance between having an ion concentration, which is high enough to enhance detection, but still low enough as to not drown out the effects of bound nanoparticles.

Impact of Electrode Dimensions on GNP Effect

As shown previously, the dimensions of the electrode system, particularly the spacing between digits, can have a significant effect on the electric field between the digits. Therefore changes in electrode dimensions should also change the effect of GNPs on the electrodes. In FIG. 25, 5 μm digits with 2.5 μm spacing was used for the three ion concentrations tested. This particular set of dimensions had the most uniform electric field profile, but different dimensions can also be tested.

Figure 27A:
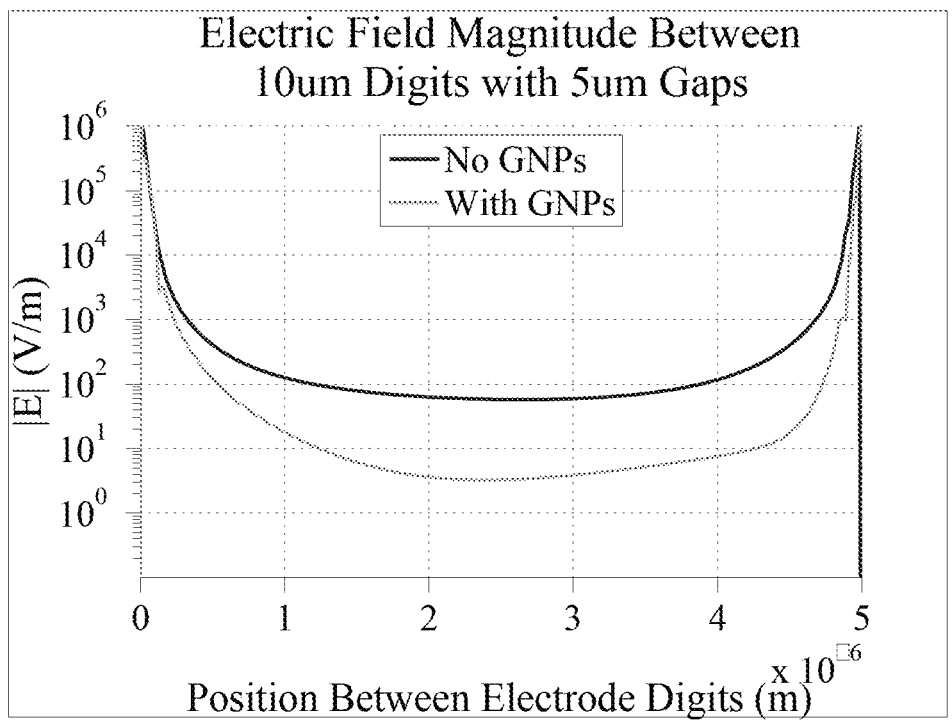
FIG. 27-A is a graph comparing the simulated electric field magnitude directly between two of the 10 μm digits with 5 μm gaps; with and without bound gold nanoparticles and a KCl concentration of 10 mM in the solution in the electrodes.
Figure 27B:
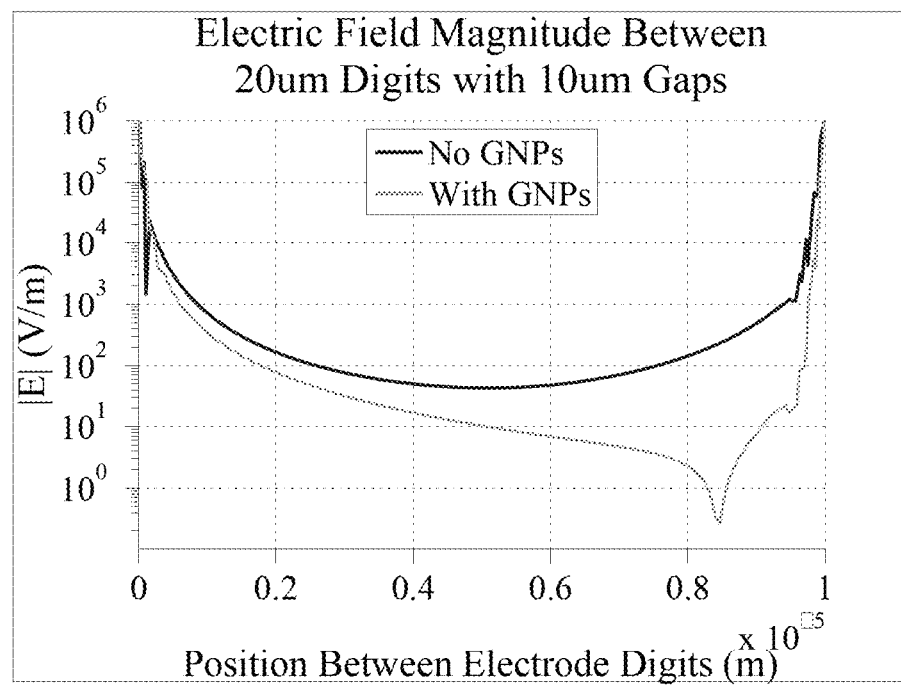

FIGS. 27A-27B shows the electric field magnitudes with and without bound GNPs (60 nm diameter, bound 20 nm above the electrodes) for two additional electrode configurations (with 0.1 V DC applied between electrodes and 10 mM KCl ion concentration in the background solution) with larger digits and gaps. The overall electric field magnitude decreases in all cases when the gap and digits increase. In FIG. 27A-27B, with 20 μm digits with 10 μm gaps, there is a non-symmetric dip in the electric field on the right side of the gap. This is likely due to the positioning of the nanoparticles on the electrode causing a lack of symmetry. The exact placement of nanoparticles obviously cannot be controlled in a practical system, so here for comparisons values of electric field magnitude are taken at the exact center of the gaps.

Figure 28:
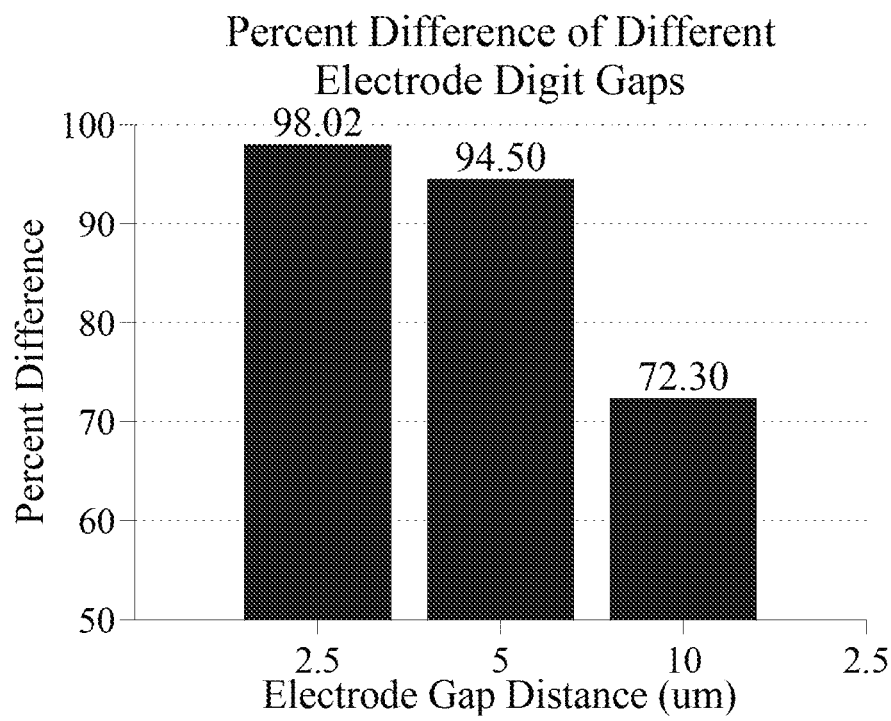
FIG. 28 is a plot showing the percent difference in the electric field magnitude at the center of the gap between electrodes digits with and without 60 nm GNPs for different electrode gap dimensions.

FIG. 28 shows a comparison of the percent differences in the electric field magnitudes at the center of the gap between digits for the different electrode geometries. In all cases, there is a 2:1 ratio in digit width to gap width. As seen here, doubling the gap distance from 2.5 μm to 5 μm results in a slight decrease in the percent difference in electric field magnitude caused by bound GNPs. Doubling the gap again to 10 μm causes a significant decrease in this difference, down to 72.3%. These results show that the smaller the electrode dimensions, the more sensitive the model is to bound GNPs. This yields overall better result. This makes physical sense as well. The closer together the digits of the electrode are, the more confined the electric field becomes, like a parallel plate capacitor. Therefore, effects of disruptions in these electric fields are more pronounced. Conversely, the electric fields between larger gaps will be less sensitive, making them better suited for detecting larger species, such as attached cells or bacteria. Therefore for this application electrodes should be designed to have the smallest dimensions possible, but the benefit of smaller dimensions becomes less significant as the dimensions decrease. Electrodes with slightly larger dimensions could still be nearly as effective without having to resort to more expensive and specialized microfabrication techniques to yield the absolute smallest dimensions possible.

Impact of GNP Size and Placement

For the above simulations, the properties and positions of GNPs themselves were kept constant, however, these exact conditions may not be possible. For example, the linkers between the electrodes and nanoparticles may be larger. Commonly used biological recognition elements, such as proteins and aptamers, can vary in size greatly, and extra molecules and modifications are sometimes necessary to facilitate bonding to the electrodes or nanoparticles.

FIG. 29A shows that, if the binding molecules attaching GNPs to the electrode are too long, the nanoparticles will be outside of the electrical screening distance of the biosensor system. This results in a negligible difference in electric field magnitude with and without nanoparticles (only 2.7% difference at the center of the gap). The screening depth of the system can be adjusted by changing the background ion concentration, and potentially change the effect of bound nanoparticles.

The size of gold nanoparticle used could also be influenced by the individual applications, as different modifications to nanoparticles are necessary for different biosensor applications (e.g., different attachment molecules required to bind to nanoparticles).

Figure 30:
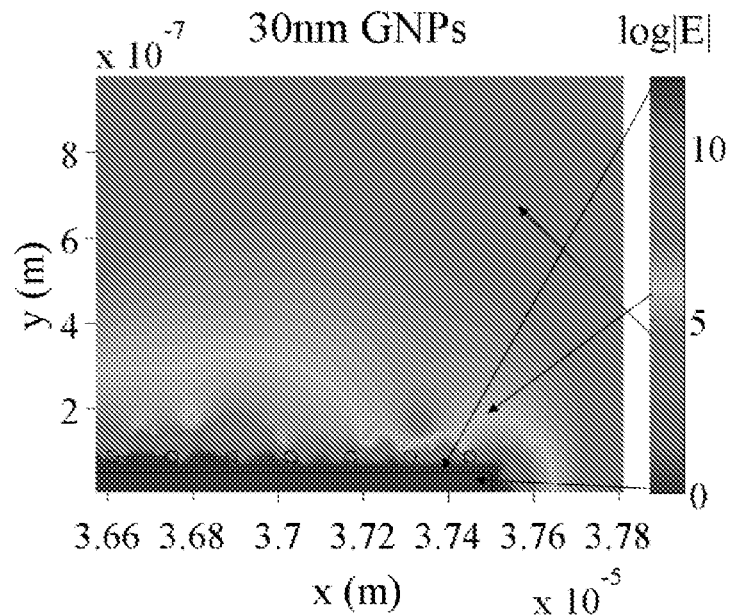
FIG. 30 is a plot of the electric field magnitude of 5 μm digit and 2.5 μm gap electrodes with 0.1 V applied, 10 mM KCl concentration and 30 nm GNPs bound to the electrodes.

With smaller nanoparticles (30 nm diameter), as shown in FIG. 30, there is actually very little change in the electric field magnitude difference between electrode digits. The percent difference in this simulation is 98.5% compared to 98.0% for the same conditions and 60 nm nanoparticles. In both cases, there were the same number of nanoparticles on the electrodes, only the size of the nanoparticles was different.

Figure 31:
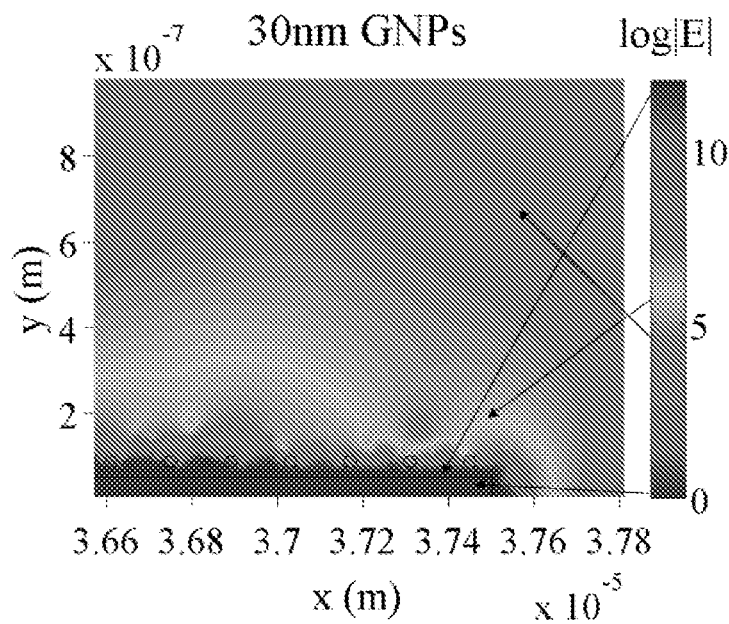
FIG. 31 is a plot of the electric field magnitude of 5 μm digit and 2.5 μm gap electrodes with 0.1 V applied, 10 mM KCl concentration and 120 nm GNPs bound to the electrodes.

With larger nanoparticles (120 nm diameter), shown in FIG. 31, there is still no significant difference in the electric field magnitude percent difference. Actually, in this particular case, the difference at the center of the gap is slightly lower than with smaller nanoparticles at 94.3%.

This indifference to the size of the nanoparticles is most likely due to the electrical screening layer established over the electrode. In each case, regardless of the size of the nanoparticles, the amount of gold in the areas over the electrodes that actually influence the electric field in the gaps stays approximately constant. As seen in FIGS. 30-31, almost all of the small nanoparticles are within the red region above the electrode whereas only a small portion of the large nanoparticles is in this region.

Since there is no major difference in these three cases at this fixed geometry and ion concentration, different criteria should be used when determining ideal nanoparticle size. Smaller GNPs could be advantageous for better stability in solution and better packing efficiency when bound to electrode surfaces, whereas larger nanoparticles can be modified with more binding molecules for better binding efficiency.

Discussion

Although these simulations have been shown to be powerful tools in showing the mechanism and some of the optimal conditions for using IDEs in biosensor applications, there are currently some limitations to these simulations. The simulations presented here only consider a DC applied voltage for the electrodes, however, for impedance measurements, AC voltages must be applied in the final design. This could affect ion transport and screening depths, but since these simulations are taken is very short time frames, DC voltages can be considered good approximations conditions for most of AC cycles. Additionally, the effects of actual biological molecules are not considered in these simulations. These molecules, either in solution around the electrodes or chemically bound to the surface of the electrodes and GNPs, could potentially also interact with the electric field as many biological molecules contain charges and can bind to certain surfaces. The goal of these simulations is to give general design rules to create the best overall system regardless of the final biomolecules involved. The versatility of this system means that many different kinds of biorecognition elements and biological samples can be involved in the detection process, with each having potential effects, positive or negative, on the function of the sensor. Because of these complexities, these potential effects were not considered in simulations. Similarly, additional fluid dynamic and electrophoretic effects were not considered in simulations. Given the dimensions and applied voltages and ion concentration ranges considered, these effects should be minimal compared to the factors considered. Other groups have done similar simulations on IDE biosensors for detecting cells and bacteria [1,20], and for simulations involving other electrode configurations [21,22]. The uniqueness in the simulations presented here comes from the specific application using nanoparticle to reduce the measured impedance across electrodes and in using these simulations as a design tool in optimizing sensor function.

Future work will focus on designing actual IDEs to validate the results of these simulations. Results of studies of actual biosensor and electrode systems can assist in choosing future parameter for further simulations and electrode optimization. Additionally, to make these simulations more comparable with actual device results, it will be necessary to simulate actual impedance values for these systems, rather than just trends in electric field differences between individual electrode digits to evaluate different models. Further optimization of electrode dimensions and conditions is also required. Although general trends have been established here for electrode digit spacing, ion concentration and GNP properties, optimizing all of these properties and more simultaneously will require more extensive simulations.

A method for simulating impedance-based IDE biosensor systems was developed using COMSOL Multiphysics software. These simulations can be used to show the effects of ions in solution over time in the establishment of electric screening layers above electrodes as well as the electric fields between the digits of the electrodes. The effect of bound gold nanoparticles under different conditions was also simulated. Under certain conditions, smaller digits and interdigit gap spacing, and higher background ion concentrations in general lead to higher percent differences in the electric field magnitude between digits, corresponding to lower measured impedance. Although smaller digits and interdigit gap spacing resulted in higher percent differences, the benefit of smaller dimensions diminishes as dimensions decrease. This indicates that electrodes with very small dimensions are not much more effective than slightly larger electrodes which do not require expensive fabrication techniques. Similarly, while higher background ion concentrations result in higher percent differences, too high would overwhelm the effect of GNPs on the system. Simulations showed that GNPs too far away from the electrodes and outside of the established electric screening distance had very little effect on the electric field between digits. The size of the nanoparticles in the simulations did not greatly affect the results. Future work with these simulations will be focused on further optimization of conditions to maximize results and make the simulations more in line with real-world devices and comparisons between simulated and actual device results. These simulations can be used as a tool for designing effective biosensor devices. The validity and effectiveness of these simulations will be evaluated by comparison to actual results from fabricated devices as well.

References

1. Radke, S.; Alocilja, E. Design and fabrication of a microimpedance biosensor for bacterial detection. *IEEE Sens. J.* 2004, 4, 434-440.
2. Alexander, F., Jr. Optimization of interdigitated electrode (IDE) arrays for impedance based evaluation of Hs 578T cancer cells. *J. Phys. Conf. Ser.* 2010, 244, doi:10.1088/1742-6596/224/1/012134.
3. Chen, J.; Fang, Z.; Liu, J.; Zeng, L. A simple and rapid biosensor for ochratoxin A based on a structure-switching signaling aptamer. *Food Control* 2012, 25, 555-560.
4. Haes, A.; Chang, L. Detection of a biomarker for Alzheimer's disease from synthetic and clinical samples using a nanoscale optical biosensor. *J. Am. Chem. Soc.* 2005, 127, 2264-2271.
5. Zeng, X.; Shen, Z.; Mernaugh, R. Recombinant antibodies and their use in biosensors. *Anal. Bioanal. Chem.* 2012, 402, 3027-3038.
6. Zheng, D.; Zou, R.; Lou, X. Label-Free Fluorescent Detection of Ions, Proteins, and Small Molecules Using Structure-Switching Aptamers, SYBR Gold, and Exonuclease I. *Anal. Chem.* 2012, 84, 3554-3560.
7. Savran, C.; Knudsen, S. Micromechanical detection of proteins using aptamer-based receptor molecules. *Anal. Chem.* 2004, 76, 3194-3198.
8. Ahn, J.; Lee, T. H.; Li, T.; Heo, K.; Hong, S.; Ko, J.; Kim, Y.; Shin, Y.-B.; Kim, M.-G. Electrical immunosensor based on a submicron-gap interdigitated electrode and gold enhancement. *Biosens. Bioelectron.* 2011, 26, 4690-4696.
9. Berggren, C.; Stålhandske, P. A feasibility study of a capacitive biosensor for direct detection of DNA hybridization. *Electroanalysis* 1999, 11, 156-160.
10. Manickam, A.; Chevalier, A.; McDermott, M.; Ellington, A. D.; Hassibi, A. A CMOS Electrochemical Impedance Spectroscopy (EIS) Biosensor Array. *IEEE Trans. Biomed. Circuits Syst.* 2010, 4, 379-390.
11. Ehret, R.; Baumann, W.; Brischwein, M.; Schwinde, A; Stegbauer, K.; Wolf, B. Monitoring of cellular behaviour by impedance measurements on interdigitated electrode structures. *Biosens. Bioelectron.* 1997, 12, 29-41.
12. Min, J.; Baeumner, A. J. Characterization and Optimization of Interdigitated Ultramicroelectrode Arrays as Electrochemical Biosensor Transducers. *Electroanalysis* 2004, 16, 724-729.
13. Bonanni, A.; Fernández-Cuesta, I.; Borrisé, X.; Pérez-Murano, F.; Alegret, S.; Valle, M. DNA hybridization detection by electrochemical impedance spectroscopy using interdigitated gold nanoelectrodes. *Microchim. Acta* 2010, 170, 275-281.
14. Cohen, A.; Kunz, R. Large-area interdigitated array microelectrodes for electrochemical sensing. *Sens. Actuators B Chem.* 2000, 62, 23-29.
15. Zhang, B.; Wang, R.; Wang, Y.; Li, Y. A Portable Impedance Biosensor for Detection of Multiple Avian Influenza Viruses. In Proceedings of the 2013 IEEE Sensor, Baltimore, Md., USA, 3-6 Nov. 2013; pp. 1-4.
16. Navani, N.; Li, Y. Nucleic acid aptamers and enzymes as sensors. *Curr. Opin. Chem. Biol.* 2006, 10, 272-281.
17. Weigand, J. E.; Suess, B. Aptamers and riboswitches: Perspectives in biotechnology. *Appl. Microbiol. Biotechnol.* 2009, 85, 229-236.

18. Song, S.; Wang, L.; Li, J.; Fan, C.; Zhao, J. Aptamer-based biosensors. *TrAC Trends Anal. Chem.* 2008, 27, 108-117.
19. Mackay, S.; Wishart, D.; Xing, J. Z.; Chen, J. Developing Trends in Aptamer-Based Biosensor Devices and Their Applications. *IEEE Trans. Biomed. Circuits Syst.* 2014, 8, 4-14.
20. Liu, F.; Arifuzzaman, S. M.; Nordin, A. N.; Spray, D.; Voiculescu, I.; Hall, S.; York, N. Characterization of Endothelial Cells Using Electrochemical Impedance Spectroscopy. In Proceedings of 2010 IEEE Asia Pacific Conference on Circuits and Systems, Kuala Lumpur, Malaysia, 6-9 Dec. 2010; pp. 252-255.
21. Li, J.; Chang, W.; Wang, M. Analysis of electrode shape effect on single HeLa cell impedance using COMSOL simulation. In Proceedings of 2013 IEEE International Conference on Bioinformatics and Biomedicine, Shanghai, China, 18-21 Dec. 2013; Volume 20, p. 7766.
22. Pradhan, R.; Mitra, A.; Das, S. Simulation of Three Electrode Device for Bioimpedance Study using COMSOL Multiphysics. In Proceedings of the 2010 International Conference on Systems in Medicine and Biology (ICSMB), Kharagpur, India, 16-18 Dec. 2010; pp. 37-40.

Example 2—Simulations and Design of Microfabricated Interdiditated Electrodes for Us in a Gold Nanoparticle Enhanced Biosensor Abstract Microfabricated interdigitated electrode chips have been designed for use in a unique gold-nanoparticle based biosensor system. The use of these electrodes will allow for simple, accurate, inexpensive, and portable biosensing, with potential applications in diagnostics, medical research, and environmental testing. To determine the optimal design for these electrodes, finite element analysis simulations were carried out using COMSOL Multiphysics software. The results of these simulations determined some of the optimal design parameters for microfabricating interdigitated electrodes as well as predicting the effects of different electrode materials. Finally, based on the results of these simulations two different kinds of interdigitated electrode chips were made using photolithography.

Introduction

Microfabrication allows for interfacing fabricated components directly with biological and chemical elements in new ways, creating opportunities for new devices. One example of this is biosensor devices. In the most general sense, a biosensor is a device which can detect, measure and report the presence of specific components in biological samples, with one of the most common examples of a biosensor being glucose sensors used by people to monitor and control diabetes [1], [2]. By detecting different biological components, biosensors can be used for numerous applications in healthcare and diagnostics. Many of these devices can take advantage of microfabricated components to allow for accurate and sensitive detection of components in biological samples [3]. Some examples of these include microfabricated cantilevers which bend under the weight of bound specific biomolecules [3], [4], and microfabricated electrodes which can be used for electrical detection of biomolecules [5], [6]. Though designs of biosensor electrodes can vary, one popular design is using interdigitated electrodes (IDEs) [7]-[9]. Essentially just microfabricated capacitors, IDEs consist of two conducting comb electrodes with interlocking digits, shown in FIG. 32. The dimensions and materials of microfabricated IDEs for biosensors can vary depending on the exact application. Electrodes with larger dimensions and space between electrode digits (in the range of 10's of microns) can be appropriate for detecting cells growing on the electrodes [8], [10], [11], whereas much smaller dimensions (several microns or below) are required for detecting small molecules such as DNA [7], [9].

This paper outlines the design of IDEs for use in a handheld impedance-based biosensor system. Detection in this system is based on binding gold nanoparticles in between IDE digits to induce a change in the measured electrical impedance of the electrodes (shown in FIG. 33). The proposed mechanism is based on binding molecular recognition elements (MREs) such as antibodies or binding proteins between electrode digits. MREs bind specifically to a particular biomolecule (in this case the biomolecule detected by that sensor), this binding is then designed to facilitate the binding of a modified gold nanoparticle to the biomolecule/MRE complex. Thus the presence of the target biomolecule leads to bound nanoparticles between the electrodes, leading to a measurable change in impedance.

In order to design the appropriate IDEs for this application, simulations were carried out to determine the ideal dimensions and conditions for this biosensor. These simulations were set up to test factors such as the ideal dimensions of the electrodes, the effect of bound nanoparticles on the electrodes, and the best electrode materials. Next, based in part on these simulation results, electrodes were fabricated using standard photolithographic microfabrication techniques.

Simulations

To perform finite element method simulations COMSOL Multiphysics software was used. This allowed for identification of frequency ranges and electrode dimensions that are more sensitive to bound gold nanoparticles. Simulations were run on different electrode geometric parameters in order to optimize the IDE design for electrochemical impedance spectroscopy (EIS). In order to simplify the simulations a 2D setup was used. Due to the symmetry of the electrode setup, impedance results from the 2D setup can be used to calculate the 3D setup as follows:

$$Z = \frac{v_{app}}{(N_e - 1)L_e\sqrt{J_x^2 + J_y^2}} \tag{5}$$

Where $N_e$ is the total number of electrode digits, $L_e$ is the length of the electrodes, $J_x$ and $J_y$ are the current densities in the simulated plane, and $v_{app}$ is the applied voltage. An assumption made by this set up is that the electrodes only interact with their nearest pair. The difference in impedance when simulations with multiple electrodes were run compared to when only a single pair was run were negligible. In order for the system of achieve linear behavior the applied voltage was chosen to be less than the thermal voltage (about 25 mV) [12]. To model the double layer the sterically modified Poisson-Boltzmann model is used. Where differential capacitance can be described for single valence ions as [13]:

$$C = \frac{\epsilon}{4\pi\lambda_D}\cosh\left(\frac{\phi_0}{2}\right)\frac{\sqrt{2}\left|\sinh\frac{\phi_0}{2}\right|}{\cosh\phi_0\sqrt{\ln(\cosh\phi_0)}} \tag{6}$$

Here $\epsilon$ is the permittivity, $\lambda_D$ is the Debye length, and $$\phi_0 = \frac{e\Phi}{k_B T}$$

where $\phi$ is the electrostatic potential.

The height of all simulated electrode systems was 50 nm. This was chosen because it is the standard thickness of deposited layers in the photolithography process used. A range of digit gap sizes and ratios of digit width to gap size were simulated from 1 to 100 MHz for gold electrodes fabricated on borosilicate glass. This allows for comparison of different geometric properties as well as identification of the frequency ranges which provide optimal sensitivity. The sensitivity was evaluated by comparing the impedance spectrum with and without gold nanoparticles. The gold nanoparticles had a radius of 30 nm which was chosen based on commercial availability and were simulated such that they covered 10% of the area between electrodes. The sensitivity value was dependent on the location of gold nanoparticles in the gap so a wide range of gold nanoparticle positions were simulated for each frequency and the resulting sensitivities were averaged. The sensitivity is calculated as:

$$S = \frac{|Z_{no\ GNPs} - Z_{GNPs}|}{Z_{no\ GNPs}} * 100 \qquad (7)$$

The peak sensitivities of a range of gap sizes and the cutoff frequencies representing the optimal measurement range value are plotted in FIG. 34, keeping the ratio of gap to electrode size at 1:2. Similarly plots for a range of electrode to gap size ratios are plotted keeping the gap size at 2 μm in FIG. 35.

As can be seen from FIGS. 34-35, reducing the gap size between digits and reducing the electrode digit width relative to the gap size both result in increases in sensitivity. However both the peak sensitivity value and the size of the ideal frequency measurement range increases with a decrease in gap size, and decreases with a reduction in the electrode digit width relative to the gap size. The reason why the location of the ideal test frequencies is important is because electronic systems capable of measuring the impedance spectrum of the electrodes would be easier to implement with greater accuracy if the measurement frequencies are lower and restricted to a smaller range. For this reason reduction of gap size to digit size ratios, either alone or in tandem with reduction in the electrode gap size would provide optimal sensitivity. The cost per electrode and electrode yield needs to be accounted for as well. As a result when selecting dimensions for fabricating electrodes the smallest dimensions that can be achieved with standard photolithography techniques, and minimal defects was chosen.

Figure 36:
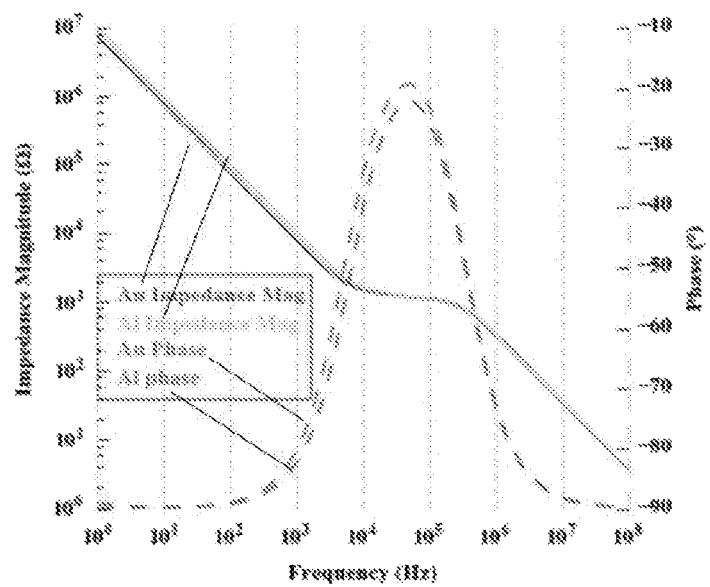
FIG. 36 is a plot of impedance magnitude and phase of aluminum and gold electrodes with a 2 μm and 1:2 gap-to-digit ratio.
Figure 37:
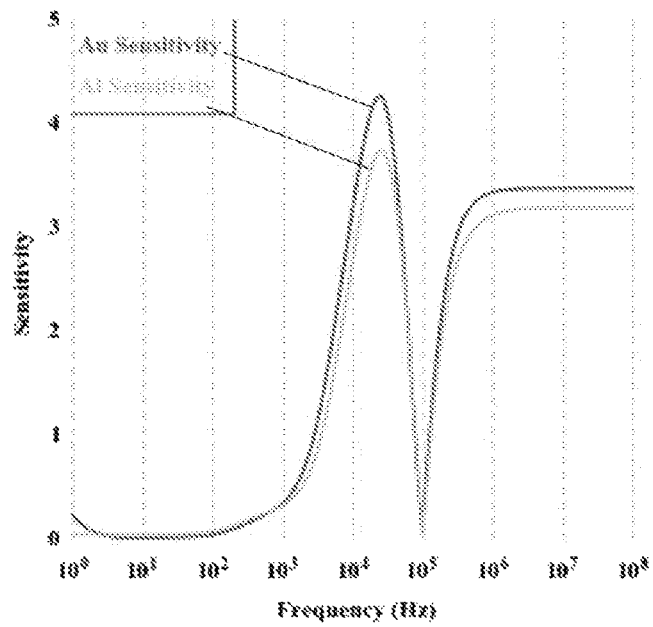
FIG. 37 is a plot comparing the sensitivity of gold and aluminum electrodes to bound gold nanoparticles over a range of measurement frequencies.

In addition to this simulations were performed for aluminum electrodes with a 1 nm aluminum oxide layer fabricated on a silicon wafer with a 0.5 μm thermally grown oxide layer. This was simulated with a 2 μm digit gap, a 1:2 gap to digit ratio, and 10% gold nanoparticle area coverage in the gap. Although gold is commonly used as a material due to biocompatibility [14] aluminum on silicon would be less expensive to fabricate and an aluminum oxide layer is formed that can prevent degradation of the electrodes. The impedance magnitudes and phases of the two different electrodes are plotted in FIG. 36. FIG. 37 compares the sensitivities over a range of frequencies between these two electrodes. As can be seen the aluminum electrodes are marginally less sensitive than the gold having a peak value of 3.74% and 4.26%.

Electrode Fabrication

Figure 38:
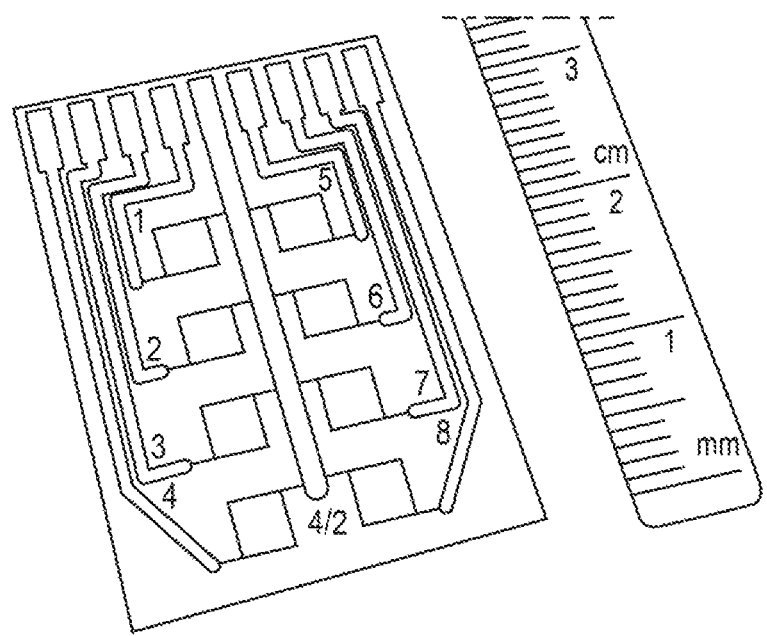
FIG. 38 is an image of aluminum electrodes patterned on silicon dioxide.

Based on these COMSOL simulations, particularly those comparing electrode spacing, a photomask was made for making IDE chips using photolithography. The mask pattern has six "electrode chips" with eight separate IDEs on each chip. Based on the simulations, an electrode digit width of 4 μm was chosen with a gap spacing of 2 μm. Simulations show that this size should be sufficient for high sensitivity detection of gold nanoparticles. While smaller dimensions should result in more sensitivity, dimensions were kept large enough for standard photolithographic techniques to reduce the cost per electrode and the number of defects. Using the mask, electrodes were made using standard photolithography, sputtering, and wet etching. Two variations of the chips were made. The first were 50 nm thick aluminum electrodes (which naturally form a thin aluminum oxide layer on them) patterned on silicon dioxide grown on silicon wafers, shown in FIG. 38. The second were 50 nm thick gold electrodes patterned on borosilicate glass (with a chromium adhesion layer).

Figure 39:
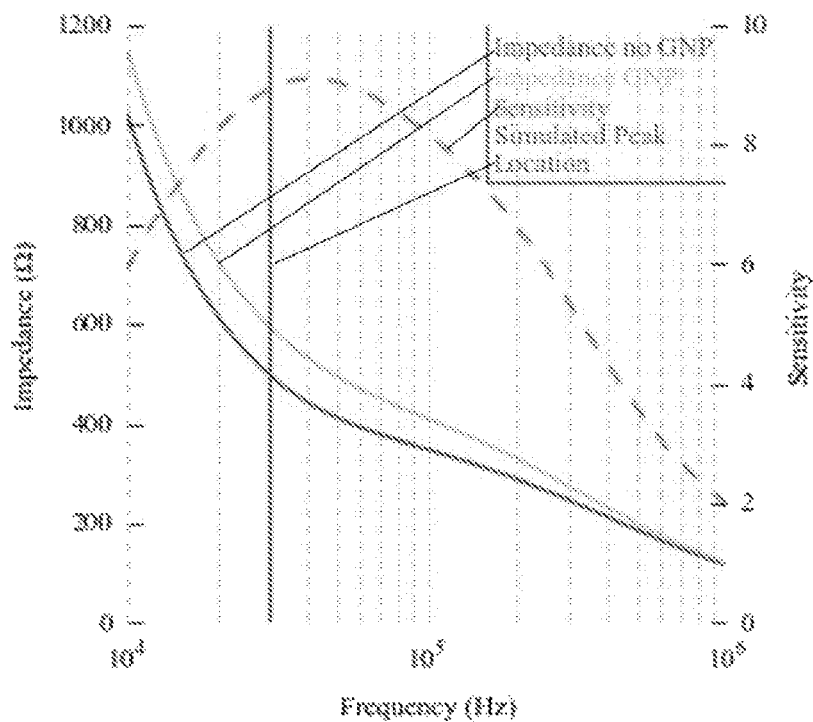
FIG. 39 is a plot of impedance magnitude with and without GNPs.
Figure 40:
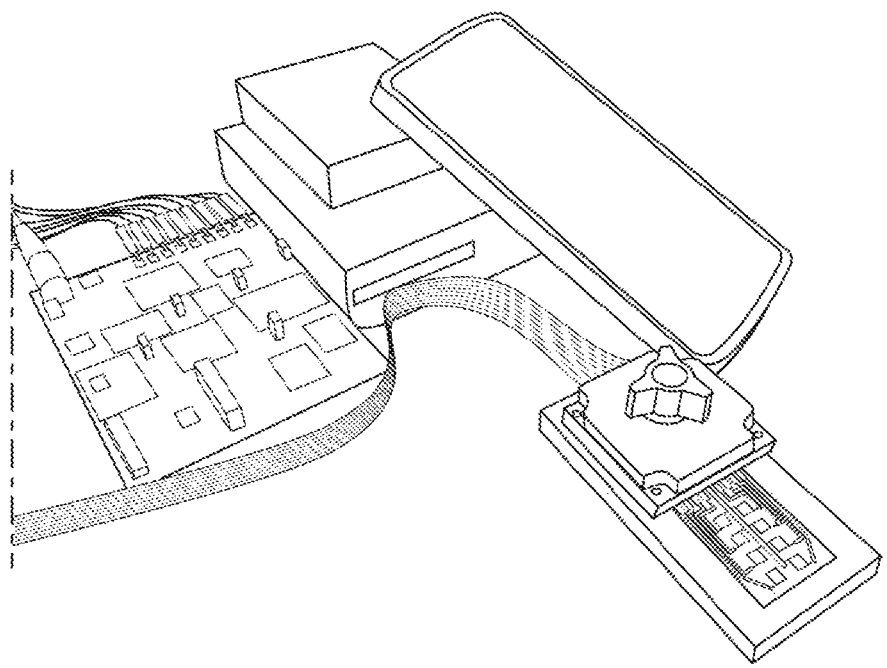
FIG. 40 is a photo of sensor equipment used for the demonstration, including the sensor board hardware, sensor case, smart phone for controlling the sensor and electrode chips for measuring FIG. 41-A is an example of the basic layout of an interdigitated gold electrode.

Preliminary experiments were run to test the proposed detection mechanism. Here gold nanoparticles were directly chemically bound between the electrodes without the presence of a target molecule. Aluminum electrodes were used as opposed to the gold because the aluminum had fewer defects from fabrication. To perform EIS a Biologic SP-200 potentiostat was used. Early results show that the form of the EIS curve is very similar to simulated, but is shifted to slightly to higher frequencies. This is apparent in FIG. 39 depicting a range of measured frequencies and the calculated sensitivity. Here the location of the simulated peak is depicted by a red line. As can be seen the actual peak lies at a higher frequency. It should be noted that the value of the measured peak sensitivity is higher than the simulated peak value. This is likely because the surface coverage of gold nanoparticles is greater in the experimental results than the 10% simulated.

Conclusions

Interdigitated electrode chips were designed and fabricated based on the results of simulations of their effectiveness in an impedance-based biosensor system. Since the IDEs used for this biosensor are fabricated using photolithography, testing many different types of electrodes with different dimensions would be incredibly time-consuming and expensive. The purpose of these simulations was to test the effectiveness of a wide range of different conditions as to narrow down the design for the fabricated electrodes. Conditions such as ranges of electrode dimensions, electrode material, and impedance measurement frequency were simulated for their effect on electrode sensitivity to gold nanoparticles. These simulations showed that in general smaller electrode gaps and a higher digit to gap ratio for the electrodes results in more sensitive detection. Additionally, simulations showed only a small difference in performance between gold and aluminum electrodes. Based on these simulations, gold and aluminum electrodes were made using photolithography.

Future work will focus on more characterization and measuring the fabricated electrodes. Impedance spectroscopy will be used to measure the impedance of different electrodes over a range of frequencies and then compare these results to the simulations. The effectiveness of the aluminum and gold electrodes will be compared in relation to their sensitivity and reliability. The effect of gold nanoparticles on the electrodes will be tested, and compared to the simulations.

References

1. E. Yoo and S. Lee, "Glucose biosensors: An overview of use in clinical practice," *Sensors*, vol. 10, pp. 4558-4576, 2010.
2. J. Wang, "Glucose biosensors: 40 years of advances and challenges," *Electroanalysis*, vol. 13, no. 12, pp. 983-988, 2001.
3. A. Hierlemann and O. Brand, "Microfabrication techniques for chemical/biosensors," *Proc. IEEE*, vol. 91, no. 6, pp. 839-863, 2003.
4. C. Savran and S. Knudsen, "Micromechanical detection of proteins using aptamer-based receptor molecules," *Anal. Chem.*, vol. 76, no. 11, pp. 3194-3198, 2004.
5. M. Moreno, V. M. Gonzalez, E. Rincón, a Domingo, and E. Domínguez, "Aptasensor based on the selective electrodeposition of protein-linked gold nanoparticles on screen-printed electrodes.," *Analyst*, vol. 136, no. 9, pp. 1810-5, May 2011.
6. B. Jang and A. Hassibi, "Biosensor systems in standard CMOS processes: fact or fiction?," *Ind. Electron. IEEE Trans.*, vol. 56, no. 4, pp. 979-985, 2009.
7. A. Bonanni, I. Fernández-Cuesta, X. Borrisé, F. Pérez-Murano, S. Alegret, and M. Valle, "DNA hybridization detection by electrochemical impedance spectroscopy using interdigitated gold nanoelectrodes," *Microchim. Acta*, vol. 170, pp. 275-281, April 2010.
8. R. Ehret, W. Baumann, M. Brischwein, a Schwinde, and B. Wolf, "On-line control of cellular adhesion with impedance measurements using interdigitated electrode structures," *Med. Biol. Eng. Comput.*, vol. 36, no. 3, pp. 365-70, May 1998.
9. J. Ahn, T. H. Lee, T. Li, K. Heo, S. Hong, J. Ko, Y. Kim, Y.-B. Shin, and M.-G. Kim, "Electrical immunosensor based on a submicron-gap interdigitated electrode and gold enhancement," *Biosens. Bioelectron.*, vol. 26, no. 12, pp. 4690-6, August 2011.
10. R. Ehret, W. Baumann, M. Brischwein, a Schwinde, K. Stegbauer, and B. Wolf, "Monitoring of cellular behaviour by impedance measurements on interdigitated electrode structures," *Biosens. Bioelectron.*, vol. 12, no. 1, pp. 29-41, January 1997.
11. S. Radke and E. Alocilja, "Design and fabrication of a microimpedance biosensor for bacterial detection," *Sensors Journal, IEEE*, vol. 4, no. 4, pp. 434-440, 2004.
12. G. Barbero, a. L. Alexe-Ionescu, and I. Lelidis, "Significance of small voltage in impedance spectroscopy measurements on electrolytic cells," *J. Appl. Phys.*, vol. 98, no. 11, 2005.
13. A. a Kornyshev, "Double-Layer in Ionic Liquids: Paradigm Change?," *J. Phys. Chem. B*, vol. 111, no. 20, pp. 5545-5557, 2007.
14. A. Manickam, A. Chevalier, M. McDermott, A. D. Ellington, and A. Hassibi, "A CMOS Electrochemical Impedance Spectroscopy (EIS) Biosensor Array," *IEEE Trans. Biomed. Circuits Syst.*, vol. 4, no. 6, pp. 379-90, December 2010.

Example 3—Live Demonstration: Portable Impedance-Based Biosensor System for Metabolomic Sensing Abstract Point-of-care biosensor devices can be important tools for monitoring and diagnosing health conditions in areas where conventional lab based testing is not practical or possible. A versatile, inexpensive, and portable biosensor has been designed to detect a variety of metabolites for metabolomic testing and disease diagnosis. The sensor works by detecting the electrical impedance change of microfabricated interdigitated electrodes when gold nanoparticles bind to the electrodes in the presence of a target biomolecule. This impedance change is detected by a custom designed handheld device that can be controlled using a smartphone for optimal ease of use and convenience, while still remaining inexpensive.

Demonstration Setup

This demonstration is of the circuitry and software involved in a portable impedance-based biosensor system. The purpose of the demo is to show a protable impedance-based biosensor which can be used to measure trace amounts of biological substances (such as DNA, proteins or metabolites). Impedance measurements of microfabricated electrodes over a range of frequencies can be measured. The sensor will show the changes in impedance caused directly by changes to the interdigitated electrodes. These changes can be caused by the introduction of buffer solutions, or by binding gold nanoparticles to the electrodes.

The equipment required for the demonstration will consist of the biosensor circuit board, the sensor itself, a smartphone with the control software, and microfabricated sensor electrodes for measurements. A laptop computer will also be used to display information relevant to the sensor functions.

Visitor Experience

Visitors to the demo can experience the user interface of the sensor and real-time impedance measurements of the sensor electrodes. Because this sensor is designed for simple, portable use, the demo will also showcase the user interface for the biosensor system. This interface is designed to be simple to operate and give clear measurement results. The sensor device itself can be controlled both using a computer and using a smart phone application, with devices connecting to the sensor via Bluetooth.

Earlier Publications

There have been three major publications directly associated with this demonstration. The first (publication 1) is a journal paper which describes the basic detection principle of the biosensor. The other two are more recent conference publications. Publication 2 describes the design of the impedance detection hardware used to measure electrical impedance of the electrodes. Publication 3 goes more in-depth on the detection mechanism, as well as showing actual impedance measurements of microfabricated sensor electrodes.

References

1. MacKay, S.; Hermansen, P.; Wishart, D.; Chen, J. Simulations of interdigitated electrode interactions with gold nanoparticles for impedance-based biosensing applications. Sensors (Switzerland) 2015, 15, 22192-22208. http://www.mdpi.com/1424-8220/15/9/22192
2. Yu, X.; Esanu, M.; MacKay S.; "An Impedance Detection Circuit for Applications in a Portable Biosensor System," *Circuits and Systems (ISCAS), 2016 IEEE International Symposium on*
3. Hermansen, P.; Mackay, S.; Wishart, D.; Chen, J. "Simulations and Design of Microfabricated Interdigitated Electrodes for Use in a Gold Nanoparticle Enhanced Biosensor," *38th Annual International Conference of the IEEE Engineering in Medicine and Biology Society.*

Example 4—an Impedance Detection Circuit for Applications in a Portable Biosensor System Abstract As the world's population ages, healthcare costs become heavy burdens worldwide. Portable point-of-care diagnostic devices, such as glucose meters, can significantly reduce the costs associated with patient care. There are many of small biological molecules present in biological samples which are of interest in healthcare applications. In this paper, a simple low-cost impedance detection circuit has been designed to detect different biomolecules such as DNA, proteins and other metabolites. In particular, the impedance across an electrode will change due to the binding of target biomolecules and gold nanoparticles. Experimental results show that the device can measure impedance changes with accuracy in the range of ±3%.

Introduction

There are many different approaches to the design of point-of-care biosensors, including optical detection methods, detection based on biomolecule mass and electrical detection [1]. Each method has its own merits and limitations, and can be well suited to different specific applications. Of these methods, electrical detection is particularly well suited for quick and simple detection of biomolecules [2]. Within the field of electrical detection, there are various specific techniques including detection using currents from electrochemical reactions [3], changes in electrical capacitance [4] and changes in electrical impedance [5, 6]. Electrical biomolecule sensor designs often depend on binding target biomolecules directly to electrodes to cause changes in electrical properties. The layout and design of electrodes used in these applications can also vary to optimize electrical signals [7, 8].

Figure 41A:
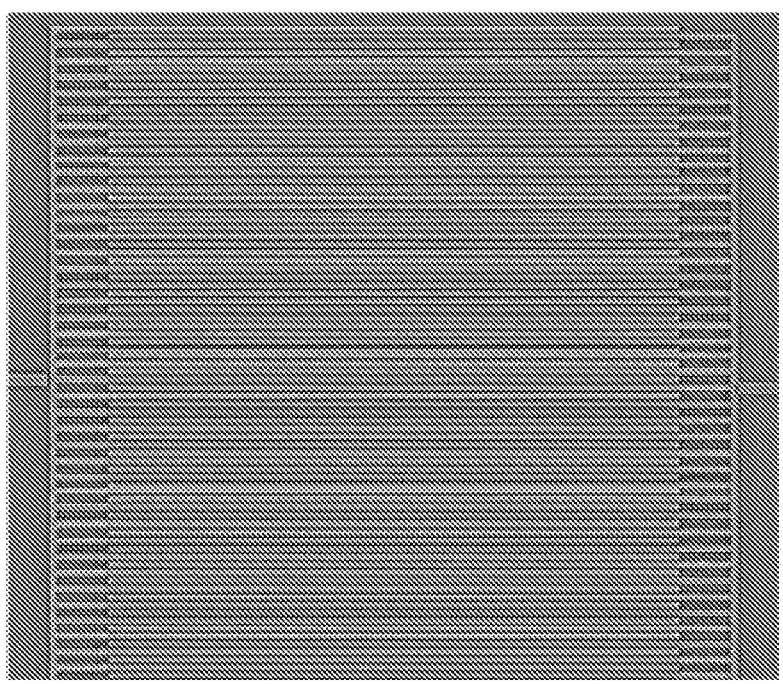
FIG. 41-B is an example of target biomolecules (e.g. DNA) binding to both modified electrodes and gold nanoparticles to disrupt the electric field between electrode digits.
Figure 41B:
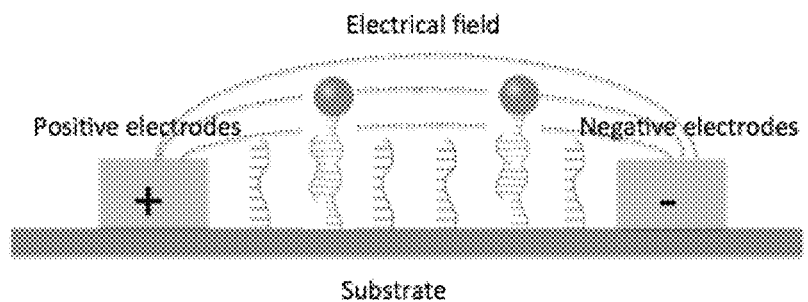

Binding proteins or DNA aptamers attached to these electrodes are used to capture target biomolecules (such as specific protein or DNA). The actual impedance change in this design is achieved using signal enhancing gold nanoparticles [9]. Nanoparticles can either be bound to target biomolecules for competitive assays or attached to secondary binding molecules to attach to the electrode surface when target biomolecules are present, as shown in FIGS. 41A-41B.

Although there have been some similar designs [7, 8], our design is unique in its simplicity. Other designs often rely on impedance spectroscopy for determining impedance changes, which requires large and expensive equipment for measurements. In our biosensor, the design of the electrode and the signal enhancement of the gold nanoparticles will allow for biomolecule detection using a simple measurement of changes in the impedance magnitude of the electrode at a set of frequencies (within 100 Hz to 100 KHz). With these requirements, it is possible to make a biosensor which is both inexpensive and small enough to be portable.

The requirements for the impedance magnitude measuring device were determined by preliminary tests of fabricated gold interdigitated electrodes. From these tests, it was determined that the circuit should provide an AC voltage at between 1-100 kHz and be capable of measuring impedance of RC components (i.e., resistors, capacitors, and the combination of them) in the range between 500Ω and 2 kΩ. This range of impedance change is sufficient for detecting biological samples.

We present in this paper an impedance measurement system that can be applied to measure the impedance changes across the interdigitated electrodes with targeting biomolecules. Several impedance measurement techniques for biomedical applications have been proposed in [10, 11], however this proposed system provides an inexpensive method that can monitor the changes of the impedance in real-time. In addition to being powered by a USB cable, this system can also be powered by a battery, which makes it portable and easy for data analysis and processing on a computer.

Proposed Architecture

Figure 42:
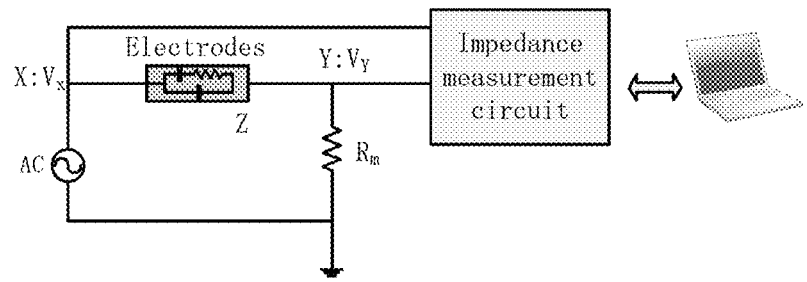
FIG. 42 is an RC circuit model of interdigitated gold electrodes bound with targeting biomolecules surrounded by a buffer solution.

The interdigitated gold electrode system in the proposed biosensor design can be modeled as the RC circuit shown in FIG. 42. In order to measure the magnitude of the impedance of the samples, the gold electrodes are connected with a resistor, which is sized based on the range of expected impedance values and in series with the electrodes, and an AC power source generating a sinusoidal wave is applied across the samples and the resistor. A circuit is proposed to measure the impedance magnitude of the sample, as shown in FIG. 42. It consists of an AC power source capable of performing a sweep between 100 Hz to 100 kHz, the electrode system to be measured, an impedance measurement circuit, and a computer to display the measured results. Assuming the sample has an impedance of Z consisting of a reactive component X and a resistive component $R_z$, the following equation can be used to relate the peak to peak voltages of $V_x$ and $V_y$.

$$\left| \frac{V_y}{V_x} \right| = G = \frac{R_m}{\sqrt{(R_m + R_z)^2 + X^2}} \qquad (8)$$

where $V_x$ and $V_y$ are the voltage of node X and node Y shown in FIG. 42 respectively, G is the ratio of $V_y$ to $V_x$ (the gain of the divider) and $R_m$ is the resistor connected in series with the sample. For the purposes of this paper, the value of $R_m$ is selected to be 2 k ohms. This value was chosen in order to provide the optimal maximum and minimum gain range for the expected impedance ranges (500 ohm to 2000 ohms) while keeping the minimum gain high enough that the lower voltage signal does not become susceptible to noise and other electrical effects in the measurement circuit. The proposed system will also measure the phase difference of the two voltages at $V_x$ and $V_y$. Transforming both voltages and the impedance Z to the phasor form yields the following equation $$\frac{V_y \angle \theta_1}{V_x \angle 0} = \frac{R_m}{(Z + R_m) \angle \theta_2} \qquad (9)$$

By equation (9), it becomes apparent that $\theta_1$ is equal to $-\theta_2$. $\theta_2$ can be expressed in terms of the components of the impedance and $R_m$ via the following equation $$\tan(\theta_2) = \frac{X}{(R_m + R_z)} \qquad (10)$$

Isolating for $(R_m + R_z)$ in equation (10) and substituting in equation (8) and isolating for X gives the following.

$$X = \frac{R_m}{G\sqrt{\frac{1}{\tan^2(\theta_2)} + 1}} \qquad (11)$$

Using trigonometric identities and substituting $\theta_2$ for $-\theta_1$, the equation can be simplified to its final form.

$$|X| = \left| \frac{R_m}{G} \sin(\theta_2) \right| \quad (12)$$

Substituting for X in equation (10) using equation (12) and isolating for $R_z$ gives the following.

$$R_z = R_m \left( \frac{\cos(\theta_2)}{G} - 1 \right) \quad (13)$$

The total impedance is then simply the vector sum of the resistive and reactive components.

Impedance Measurement Circuit

Figure 43:
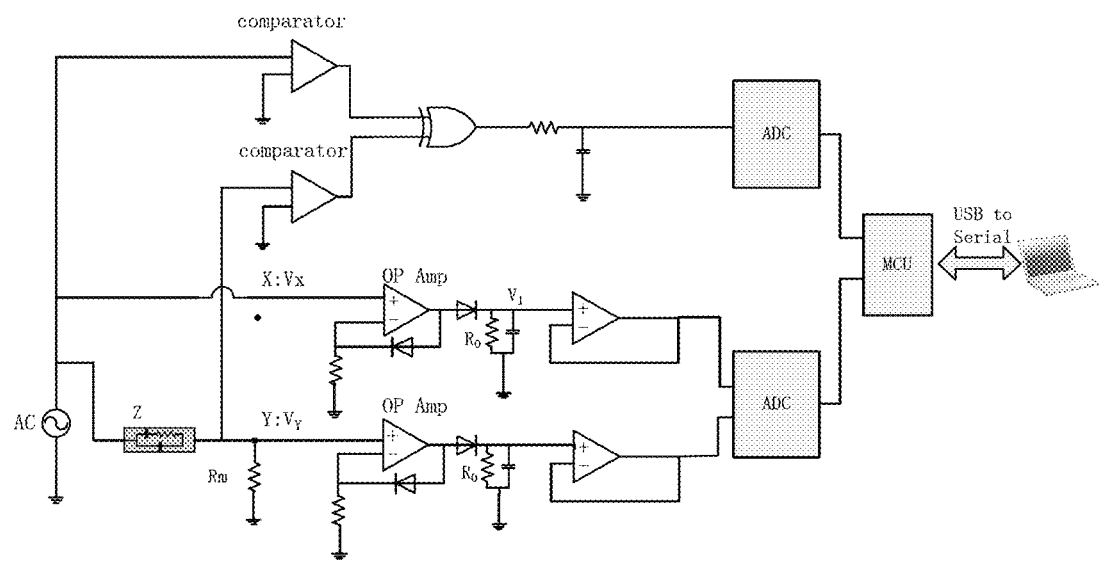
FIG. 43 is a schematic of an impedance detection circuit.
Figure 44:
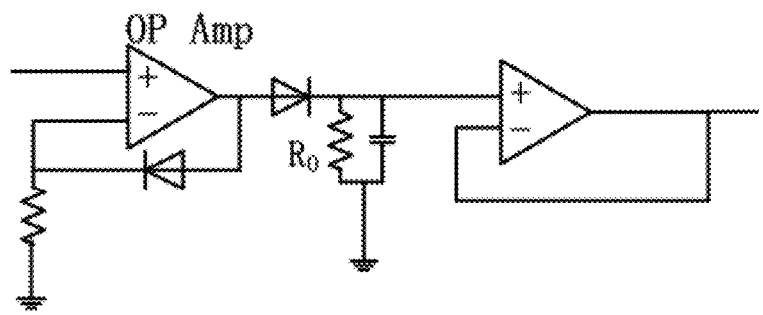
FIG. 44 is a schematic for an open loop peak detector system.
Figure 45:
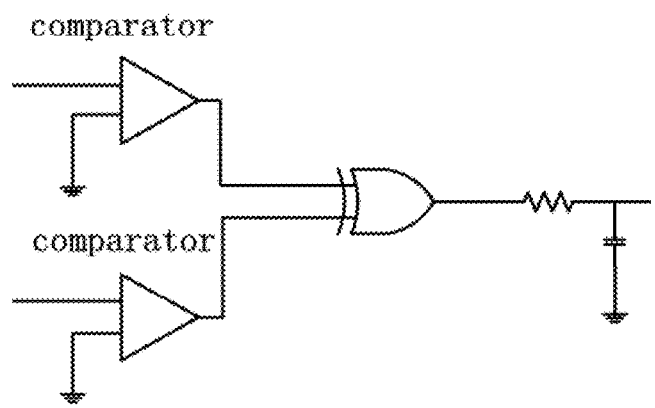
FIG. 45 is a schematic for a phase measurement system.
Figure 46:
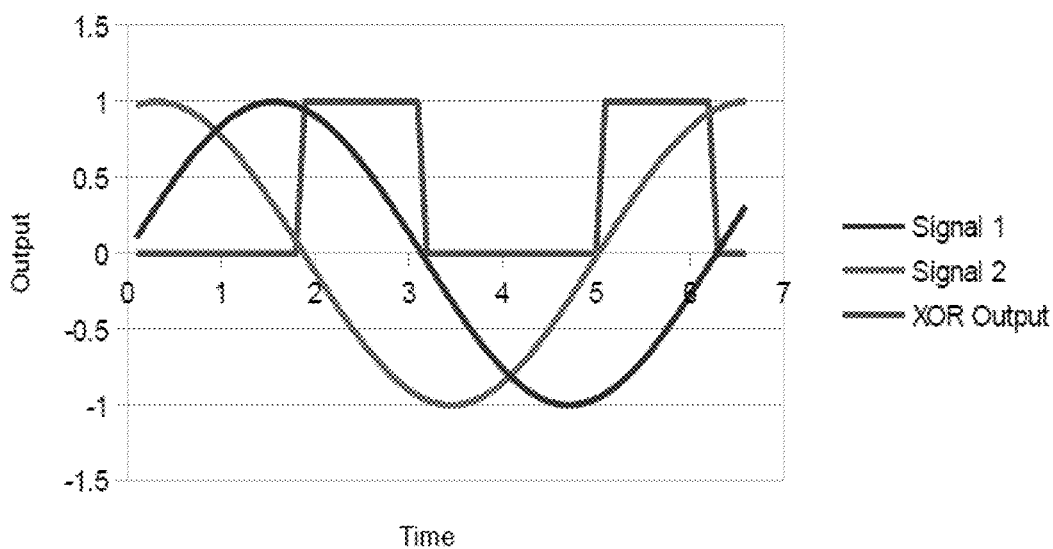
FIG. 46 is a plot of the phase measurement system.

The impedance measurement circuit is applied to measure the peak voltage value at node X and node Y as well as the phase difference between the two AC voltages at the two nodes. The detailed schematic of the impedance measurement circuit is illustrated in FIG. 43.

It consists of two active open loop rectifiers, two dual channel ADCs, two high speed CMOS comparators (one dual comparator IC), a two-input XOR gate with a low pass filter at the output and a micocontroller for reading data from the ADCs, as well as several buffers to reduce loading effect based errors. The input AC signal is supplied by an AD9837 DDS chip.

Magnitude Measurement Circuit

The magnitude measurement circuit consists of two open loop peak detectors. The design of the open loop rectifier system is based on the Linear Technologies design note 61 [13]. The open loop peak detector provides excellent performance at high frequencies, but is limited by minute differences between the forward voltage drops of the two diodes being used. To combat this effect, a class of diode known as a stabistor diode, or forward voltage reference diode, was utilized. The particular stabistor chosen was the BAS17, which has excellent low voltage characteristics. The buffer has been added in order to mitigate the effects caused by the low input resistance (~50 k ohm) of the MCP3202 ADC.

Phase Measurement Circuit

The phase measurement circuit utilizes two high speed TTL comparators configured as zero cross detectors, which output a logic value of 1 when the signal is above the zero point and a logic value of 0 when the signal is below the 0 point. The input to each comparator is the AC waveform at nodes X and Y. The output of each comparator is then goes to an input of a 2 input XOR gate. The output of the XOR gate is then a PWM signal, with a duty cycle that is directly proportional to the phase difference of the two signals. A 180 degree phase shift corresponds to a 100% duty cycle, while a 0 degree phase shift corresponds to a 0% duty cycle. The duty cycle of the signal can be determined by either direct timing, or through low pass filtering to a DC signal that can be directly read by an ADC. For the purposes of this paper, the latter method was utilized.

Measurement Results

In order to verify the effectiveness of the circuit, this impedance measurement system was applied to measure the impedance of some resistors, capacitors and RC combinations. Measurements taken with this system were compared to both theoretical values of the resistor and capacitor components and results measured with a commercial LRC meter U1733C (Agilent Technologies, Santa Clara, Calif., accuracy is 0.2%), as shown in Table. 1A.

TABLE 1A

Impedance Measurements (Magnitude Only) Taken at 10 kHz for Various Components

| Measured component | Measured Impedance at 10 kHz | | |
|---|---|---|---|
| | Circuit measurement | LRC Meter measurement | Error |
| 1k Resistor | 971.18 Ω | 996.4 Ω | 2.53% |
| 12.3 nF capacitor | 1260.12 Ω | 1273 Ω | 1.01% |
| 12.3 nF ∥ 1.75 nF | 1113.05 Ω | 1119 Ω | 0.53% |
| 1k Resistor - 12.3 nF ∥ 1.75 nF | 1473.37Ω | 1506 Ω | 2.17% |
| 1k Resistor - 12.3 nF capacitor | 1576.14 Ω | 1620 Ω | 2.71% |

Measurements in Table 1A show impedance magnitudes of various components all within the designed magnitude range (between 1 k Ω and 2 k Ω) for the final specifications for the biosensor device. For the sake of simplicity for these measurements, only the impedance magnitude (and not the phase) was recorded, and one representative frequency, 10 kHz, was used for these measurements. This frequency was chosen because it kept the chosen components in the desired impedance range, was in the specified range for the device and was one of the frequencies the LCR meter can produce. As seen from these results, for all of the components tested, including resistors, capacitors, and combinations of these, there is less than a 3% error between the impedance measuring circuit and the LCR meter.

Figure 47:
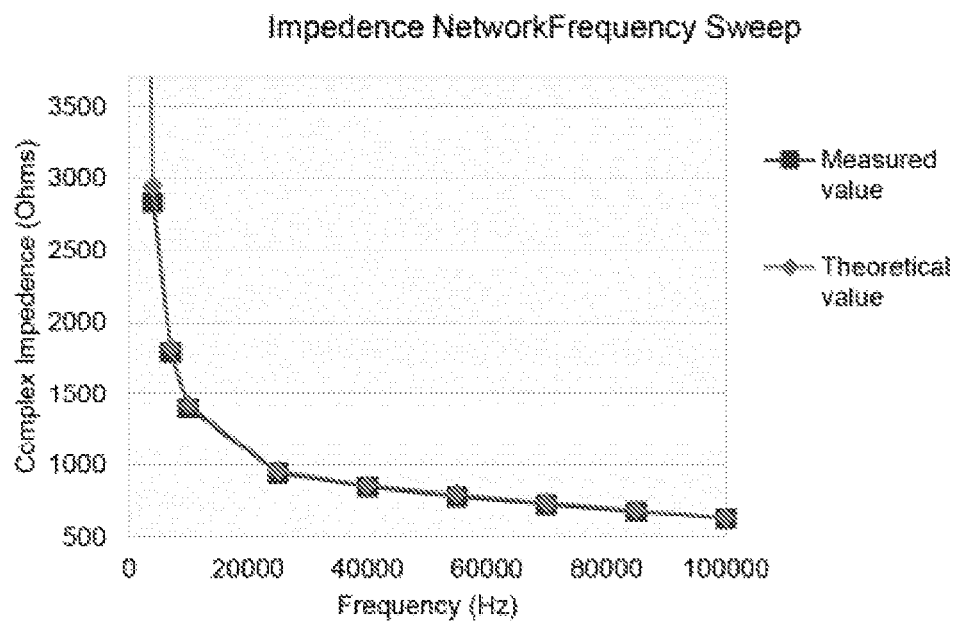
FIG. 47 is a graph comparing measured impedance values to theoretical values for components representative of an interdigitated electrode in a buffer solution.

Next, the performance of the impedance circuit over its designed frequency range was tested. Measurements were taken at several set input frequencies between 1 kHz and 100 kHz on a circuit that is representative of an actual biosensor electrodes, shown by the equivalent circuit in FIG. 42. This tested circuit consisted of a 471 pF capacitor in series with a 1 kΩ resistor both in parallel with a 1759 pF capacitor. The results of impedance measurements for this system were compared to the theoretical values at set frequencies and are shown in FIG. 47.

Overall, there is very close agreement between the measured values and calculated theoretical values, with the largest deviations at lower frequencies, at 12% error at 10 kHz, but much smaller errors above that, with all other measurements at higher frequencies within 3% error. This large error at 10 kHz is due to the measured RC components having an impedance higher than 2K ohms at this frequency, which is outside the designed magnitude range.

Figure 48:
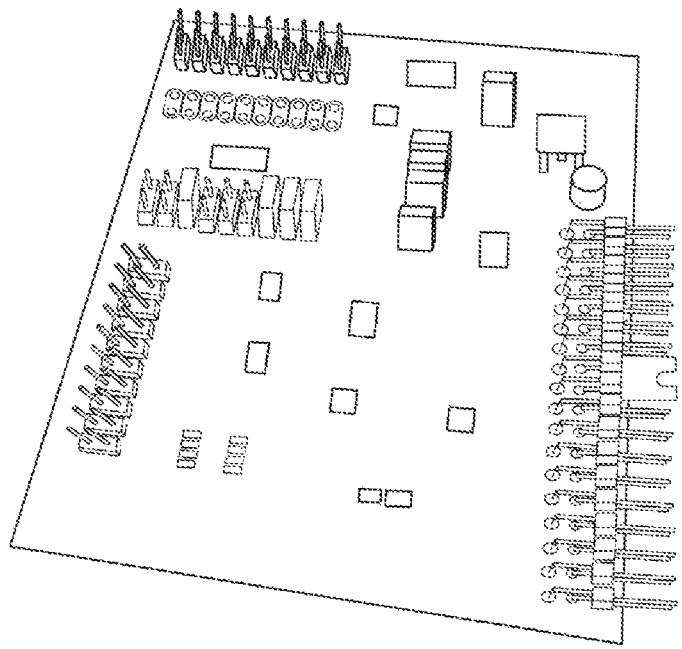
FIG. 48 is an image of a design for the impedance detection circuit.

The designed system is shown in FIG. 48. The total cost of the system built on PCB under $40, which is much cheaper than the commercial RLC meters (usually cost at least $100). Compared to the commercial LRC meter and other impedance meters, this designed system has several advantages including inexpensive components, functioning at a range of frequencies rather than several set frequencies. Moreover, this impedance detection circuit can be customized to integrate with the interdigitated gold electrodes biosensor device to make a portable real-time sensor system. Additionally, the device can be connected to a computer for data output, recording, and processing, a necessary step for any biosensor applications.

Conclusion

The paper presents a design for a biosensor system dedicated to biomolecule detection. This system applies interdigitated electrodes to measure the impedance magnitude changes across the electrodes due to different impedance of the solutions. This system provides a real-time measurement of the impedance changes at a range of frequencies and displays the results on a computer. Compared to commercial LCR meters, the proposed system is much cheaper and could be powered either by batteries or by a USB cable; therefore it is possible to make it an inexpensive portable device for simple and quick detection of biomolecules. Experiments of measuring the impedance of RC components have verified the effectiveness of the system. In addition, this system works at a range of frequencies, which makes it flexible for measuring different biomolecules at an optimal frequency. Future work will focus on refining the AC source, including a step-down stage to only deliver very low voltages to any biosensor electrodes, and computer communication for data processing.

References

1. S. Song, L. Wang, J. Li, C. Fan, and J. Zhao, "Aptamer-based biosensors," TrAC Trends Anal. Chem., vol. 27, no. 2, pp. 108-117, 2008.
2. J. Ahn, T. H. Lee, T. Li, K. Heo, S. Hong, J. Ko, Y. Kim, Y.-B. Shin, and M.-G. Kim, "Electrical immunosensor based on a submicron-gap interdigitated electrode and gold enhancement," Biosens. Bioelectron., vol. 26, no. 12, pp. 4690-6, August 2011.
3. L. Bonel, J. Vidal, P. Duato, and J. Castillo, "An electrochemical competitive biosensor for ochratoxin A based on a DNA biotinylated aptamer," Biosens. Bioelectron., vol. 26, no. 7, pp. 3254-3259, 2011.
4. C. Berggren and P. Stålhandske, "A feasibility study of a capacitive biosensor for direct detection of DNA hybridization," Electroanalysis, vol. 11, no. 3, pp. 156-160, 1999.
5. Y. Peng, D. Zhang, Y. Li, H. Qi, Q. Gao, and C. Zhang, "Label-free and sensitive faradic impedance aptasensor for the determination of lysozyme based on target-induced aptamer displacement," Biosens. Bioelectron., vol. 25, no. 1, pp. 94-9, September 2009.
6. A. Bonanni, I. Fernández-Cuesta, X. Borrisé, F. Pérez-Murano, S. Alegret, and M. Valle, "DNA hybridization detection by electrochemical impedance spectroscopy using interdigitated gold nanoelectrodes," Microchim. Acta, vol. 170, pp. 275-281, April 2010.
7. Y. Iwasaki and M. Morita, "Electrochemical measurements with interdigitated array microelectrodes," Curr. Sep., vol. 1, no. 13, pp. 2-8, 1995.
8. A. Cohen and R. Kunz, "Large-area interdigitated array microelectrodes for electrochemical sensing," Sensors Actuators B Chem., pp. 23-29, 2000.
9. S. MacKay, D. Wishart, J. Z. Xing and J. Chen, "Developing trends in aptamer-based biosensor devices and their applications," IEEE Transactions on Biomedical Circuits and Systems, vol. 8, no. 1, pp. 4-14.2014.
10. C. Donfack, M. Sawan and Y. Savaria, "Fully integrated AC impedance measurement technique for implantable electrical stimulation applications," the fifth Annual Conf. International FES Society, Aalborg, 2000.
11. C. Donfack, M. Sawan and Y. Savaria, "Implantable measurement technique dedicated to the monitoring of electrode-nerve contact in bladder stimulators," Med. Biol. Eng. Comput. Vol. 38, no. 4, pp. 465-468.2000.
12. P. Van Gerwen, W. Laureyn, W. Laureys, G. Huyberechts, M. De Beeck, K. Baert, J. Suls, W. Sansen, P. Jacobs, L. Hermans and R. Mertens, "Nanoscaled interdigitated electrode arrays for biochemical sensors," Sensors and Actuators b-Chemical, vol. 49, no. 1, pp. 73-80, 1998.
13. J. Williams. "Linear Technology Application Note 61: Practical Circuitry for Measurements and Control Problems," August 1994.

Example 5—Using Impedance Measurements to Characterize Surface Modified with Gold Nanoparticles Abstract With the increased practice of preventative healthcare to help reduce costs worldwide, sensor technology improvement is vital to patient care. Point-of-care (POC) diagnostics can reduce time and lower labor in testing, and can effectively avoid transporting costs because of portable designs. Label-free detection allows for greater versatility in the detection of biological molecules. Here we describe the use of an impedance-based POC biosensor that can detect changes in the surface modification of a micro-fabricated chip using impedance spectroscopy. Gold nanoparticles (GNPs) have been employed to evaluate the sensing ability of our new chip using impedance measurements. Furthermore, we used impedance measurements to monitor surface functionalization progress on the sensor's interdigitated electrodes (IDEs). Electrodes made from aluminum and gold were employed and the results were analyzed to compare the impact of electrode material. GNPs coated with mercaptoundecanoic acid were also used as a model of biomolecules to greatly enhance chemical affinity to the silicon substrate. The portable sensor can be used as an alternative technology to ELISA (enzyme-linked immunosorbent assays) and polymerase chain reaction (PCR)-based techniques.

Introduction

Biosensors are a popular research area because of their vast potential for improving healthcare. The ability to test for a specific biomarker can help detect diseases such as cancer while they are still localized. (1, 2) While there are technologies in existence that can perform such tasks, they often require samples to be tested at a laboratory dedicated to this purpose. Both transporting and testing the sample can be expensive and time-consuming, making a point-of-care design ideal in terms of time and cost efficiency. (3, 4) Various bio-sensing techniques have been proposed using optical, (5-7) electrical, (8, 9) and mechanical (10-12) detection methods. Compared to optical methods of detection, impedance tests are easier to use and more versatile. The equipment often required for optical detection is too large, complex, and expensive for portable point-of-care testing. However, optical methods tend to achieve high sensitivity, which is why they are commonly used. (13) Mechanical methods, on the other hand, can yield specific and sensitive results, but they are much more prone to inaccuracies due to temperature and pH changes. (14)

Figure 49:
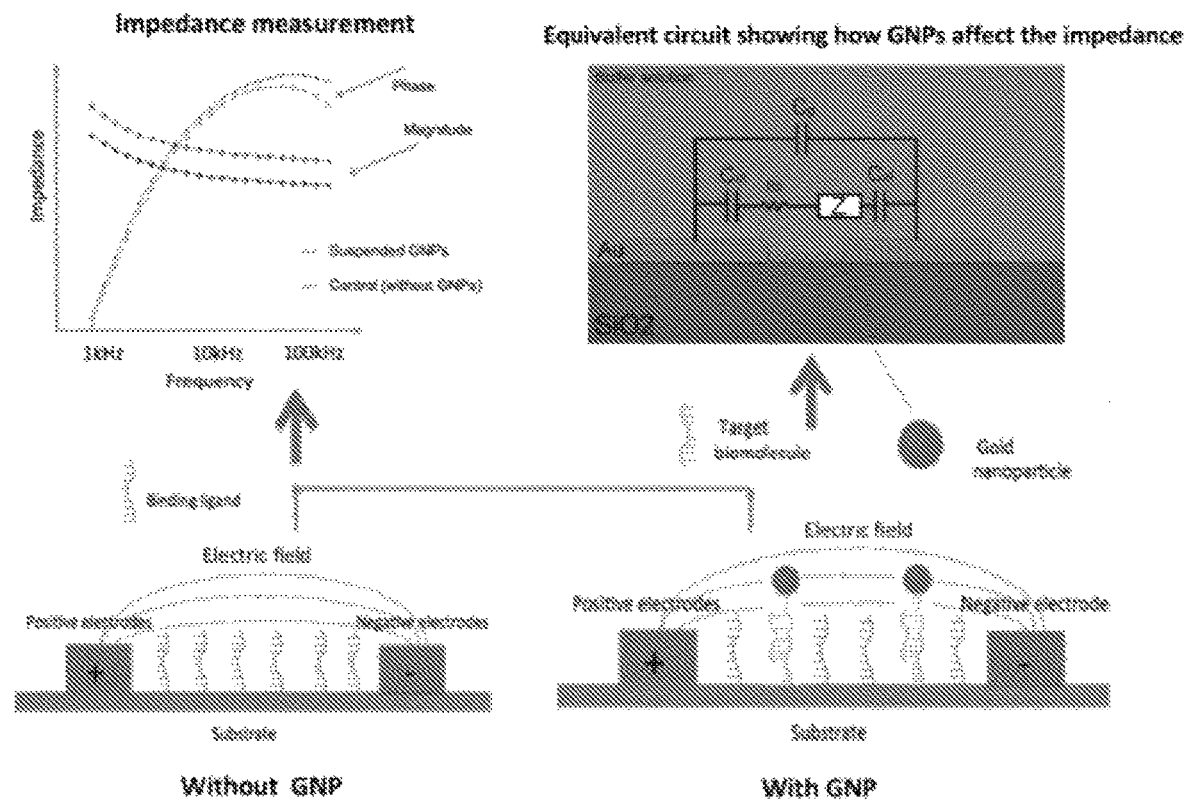
FIG. 49 is a diagram of gold nanoparticles bound by target biomolecules disrupting the electric field between electrodes, causing a change in impedance.

Impedance-based detection methods have been shown to have a lower maximum sensitivity than other techniques. (15) However, we can enhance the sensitivity of the impedance measurements by using gold nanoparticles (GNPs). (16) Such a design yields more precise results. The mechanism by which GNPs affect the impedance of the system can be represented using the equivalent circuit shown in FIG. 49. This circuit is a combination of the double layer capacitance of the electrode digits ($C_{dl}$), the physical capacitance of the electrode ($C_g$), the resistance of the surrounding buffer solution ($R_s$), and the impedance introduced by the bound nanoparticles (Z). Since this is a non-faradic system that does not depend on electron transfer from electrochemical reactions, complex elements, such as electron transfer resistance and mass transfer resistance are not required. (17) The GNPs provide a change in impedance through the phenomenon of double layer capacitance. Charges in the solution surrounding the nanoparticles build up around the oppositely charged surface of the GNP. This forms two layers of charge (double layer). The build-up of charge closely resembles the effects of a capacitor. Consequently, the GNPs provide a capacitive change when bound to the surface between electrodes. Nanoparticles have been used in a variety of biological applications, such as drug and gene delivery, cancer therapy, and protein detection. (18) GNPs have been shown to be highly adjustable in their modification, (15, 19) and assorted methods for binding GNPs using aptamers exist. (20, 21) An aptamer is a biological molecule that can bind to a specific substance with extremely high specificity. They are typically constructed from oligonucleotides or peptides.

Figure 50A:
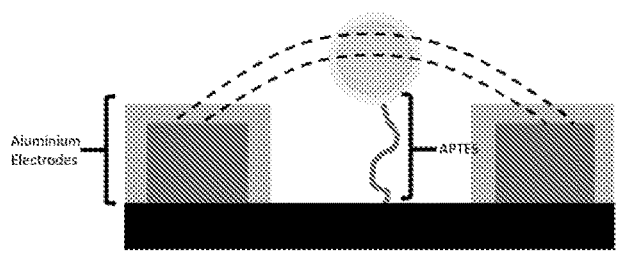
FIG. 50-A is a schematic of aluminum electrodes with oxide coating and electric field lines.

Microfabricated chips with interdigitated electrodes (IDEs) were used to characterize surface modification with GNPs (FIGS. 50A-50F). IDE sensing chips were created to have 3 mm×3 mm squares of IDEs on a silicon dioxide substrate (refer to FIGS. 50C-50D). The electrodes were created using standard photolithographic microfabrication techniques to create 2 µm of spacing between electrode digits that are 4 µm wide. Evidence has shown that the smaller the spacing, the more sensitive the impedance is to the presence of chemical species in between IDEs. (22) Some example results from these simulations using COMSOL Multiphysics are shown in FIGS. 50E-50F. These results show the layout of the simulation along with the associated electric field distribution, and the simulated sensitivity of IDEs to bound nanoparticles. Results show a specific distribution of sensitivities for nanoparticles bound to IDEs as well as the predicted behavior and frequency range of interest for impedance measurements. The purpose of experiments presented here are as proof-of-concept experiments of the detection principle shown by the simulations. The change in impedance should rely only on the binding of nanoparticles, so directly binding GNPs chemically to IDEs should result in the same effect as the simulations. The simulation also proves the efficacy of this method to be used with molecular recognition elements for future biosensing applications.

Figure 50B:
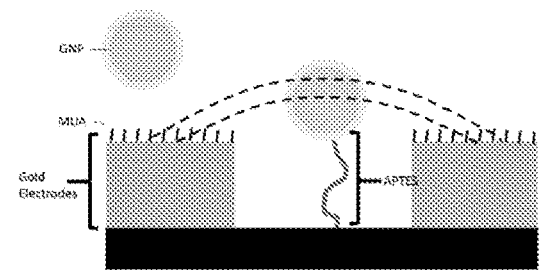

Tests were performed on chips made of either aluminum or gold electrodes (FIGS. 50A-50B). Aluminum electrodes have the benefit of having a naturally occurring aluminum oxide layer. Aluminum oxide is an excellent dielectric increasing the capacitive character of our design. This is preferable because the primary cause of impedance change detected is a change in capacitance from the addition of GNPs. Gold electrodes are far more chemically stable. Its noble metal features allow for less corrosion and unwanted chemical reactions in buffer and salt solutions. Gold does not react with most biological molecules making it useful for sensing these types of molecules. However, the weak adhesion affinity of the gold on silicon dioxide substrate makes its microfabrication much more difficult and expensive. While aluminum electrodes are easier and more reliable to fabricate, gold electrodes are much more resistant to corrosion and have greater biocompatibility. Another benefit for gold electrodes is their affinity for molecules with thiol groups. This allows for surface modifications of the electrodes themselves after microfabrication.

Modifications of the electrode surfaces using a self-assembled monolayer were also investigated. (23) It has been shown to reduce corrosion, (24, 25) and it was hypothesized that it would mimic the effect of the oxide layer on aluminum electrodes (FIG. 50A). This was accomplished by modifying the gold IDEs with MUA via its thiol group (FIG. 50B). Other researchers have performed similar procedures. (25, 26) This type of modification is well-defined and can be used to bind certain molecules to a surface. (27, 28) Here, the experimental results performed on chips with both aluminum and gold electrodes that have been chemically activated to covalently bind with surface modified GNPs are shown and discussed. Firstly, the IDEs were coated with (3-Aminopropyl)triethoxysilane (APTES) at different concentrations. The GNPs were coated with MUA facilitating the binding with chemical modified electrode. At each APTES concentration, GNPs were bound using EDC/NHS chemistry as a model for biological binding. This is to investigate the effects of the GNPs solely and prove the theoretical concept previously reported. Due to the versatility of GNPs modification, the sensor should allow for the detection of a variety of biological molecules. Modifications have been characterized through impedance spectroscopy and with an atomic force microscope (AFM). These results are compared with simulation results that have been performed using the design of the chip, which have been previously reported. (16, 29) COMSOL Multiphysics software was used to create simulations of IDEs with a range of dimensions, buffers, and nanoparticle positions. The position of the nanoparticle in relation to the IDE was also simulated for the distance from the surface of the electrode. These simulation results showed that there was no significant change in sensitivity based on the separating distance between the nanoparticle and the IDEs substrate as long as it never exceeds the height of the electrode digits. This result is particularly relevant for future tests involving different recognition elements. DNA, proteins, and antibodies can have very different sizes, so nanoparticles modified with these biomolecules would bind to the electrodes at different separating distance. The results of these simulations show that regardless of the recognition element used, the sensitivity should remain the same.

Methods

Basic Impedance Tests

A polydimethylsiloxane (PDMS) well covering was placed on top of the chip, which provided a well to hold a solution of electrolyte over each well. PDMS well coverings were constructed to have a perfectly flat bottom surface to ensure a water-tight seal on the microfabricated electrodes. 50 µL of 150 µM KCl solution were placed onto each well as an electrolyte. KCl is a very simple solution and for our purposes we wished to simplify certain aspects of the experiments. The concentration of KCl carried a current between electrodes as an electrolyte and lowered the effect of extraneous substances from changing the ionic strength of the solution such as carbon dioxide. Carbon dioxide dissolving from air and becoming ionized carbonic acid could increase the electrolyte's ionic strength. Therefore, the ionic strength needed to be high enough to limit the effect this phenomenon may have. However, if the ionic strength of the solution is too high, its impedance overshadows any changes in surface modification.

This sensor design is intended to be used as a biosensor in future applications. In general, biological samples that would be tested have much higher ion concentrations than our measurement buffer used in the current studies. This factor has to be taken into consideration when designing the sensor. Biological conditions have ionic concentrations that are likely too high for this detection to work properly. However, when biological samples are used, the chemical binding part of the sensing is the only part that requires these concentrations. After exposure to the biological sample (and resulting biological conditions), the sample is removed and a "measurement buffer" with the appropriate ionic concentration is added for the impedance measurement to take place.

Impedance measurements were done using a voltage amplitude of 10 mV, and a frequency sweep of 10 kHz to 1 MHz for the aluminum electrodes and a larger sweep of 1 kHz to 1 MHz for gold electrodes. Each frequency was tested five times and their average was used. Impedance spectroscopy was carried out using an electrochemical measurement station (IS, SP-200, BioLogic Inc.). After testing, chips were rinsed with milli-Q water, sonicated in milli-Q water and then washed using ethanol.

Synthesis and Surface Functionalization of GNPs:

The synthesis of the GNPs followed the Turkevich-Frens method using trisodium citrate dihydrate (TSC) (Sigma-Aldrich) as both a reducing and dispersion agent. Hydrogentetrachloroaurate trihydrate ($HAuCl_4.3H_2O$) (Sigma-Aldrich, 99.9%) was employed as a gold precursor, where the synthesis and the nanoparticle washing were performed as previously reported. (30) The prepared NPs were characterized by transmission electron microscopy (Philips 410 TEM), inductive plasma couple combined with atomic emission spectroscopy (Thermo Scientific iCAP 7000 Series) and optical spectroscopy (Agilent 8453 UV-vis Spectrophotometer).

The surface functionalization of the GNPs was carried out as follows. To a 5 mL dispersion of GNPs with an estimated concentration 0.22 µM, a 5 mL aqueous solution consisting of 2 mM Poly(ethylene glycol) methyl ether thiol Molecular Weight 800 (mPEG-SH, Sigma-Aldrich) and 2 mM of 11-Mercaptoundecanoic acid (MUA) (Sigma-Aldrich) was added drop wise. The concentration of MUA was selected to be 20% (V/V). The reaction solution was stirred overnight to ensure sufficient functionalization of the nanoparticles. Then the MUA-GNPs were collected by centrifugation at 13000 rpm for 10 min. The MUA-GNPs were washed by redispersing the NPs plate in Milli-Q water. The last two steps were repeated two more times to completely remove the unbound thiol compounds. The nanoparticles surface's functionalization was evaluated by zeta potential measurement (Zetasizer Malvern).

APTES Modification: Before treating the IDEs with APTES, oxygen plasma cleaning (FIGS. 51A-51D were used to clean and activate the silicon surface. APTES ethanolic solutions of different concentrations (2, 5, 7 and 10%) were freshly prepared. APTES solutions were individually drop casted on the top of the IDEs and incubated for 2 hours. Afterward, the APTES solution was removed and the IDEs were washed several times using absolute ethanol. After rinsing and sonication in both milli-Q water and ethanol, impedance tests were performed.

MUA-GNPs/APTES Modified IDEs Binding:

The binding of the MUA-GNPs to the APTES-IDEs was performed using EDC/NHS bioconjugation chemistry. (31) The carboxylic group at the nanoparticles surface was activated by addition of 30 mM N-Hydroxysuccinimide (NHS (Sigma-Aldrich, 98%), and 15 mM N-(3-Dimentylaminopropyl)-N'-ethylcarbodiimide (EDC, Sigma-Aldrich) in MES buffer (Sigma-Aldrich), to MUA-GNPs dispersion. A PDMS template cover with 8 well was fixed over the chip, where each well set directly over each IDEs. Later, 50 µL of the activated MUA-GNPs were added in each well and the IDEs were incubated overnight to complete the binding. The NPs solution was discarded from each well and all IDEs were washed several times with Milli-Q water removing unbound NPs. The chip was then rinsed and sonicated one last time, and impedance measurements were performed.

Gold Electrode Surface Modification:

The thiol groups on the MUA is bound to the gold IDEs (FIG. 50B). Thiol groups have a high affinity for gold. (32) A 50 µL solution of 1 mM MUA was placed on each well for overnight to allow for adsorption of the MUA to the surface of the electrodes. This creates a layer of a long-chain alkane with a carboxy-functional group on the end. This functional group helps to prevent molecules from chemically binding to the surface. After this was accomplished, the electrode was modified by APTES and GNPs in the same way as above.

Results

Figure 51E:
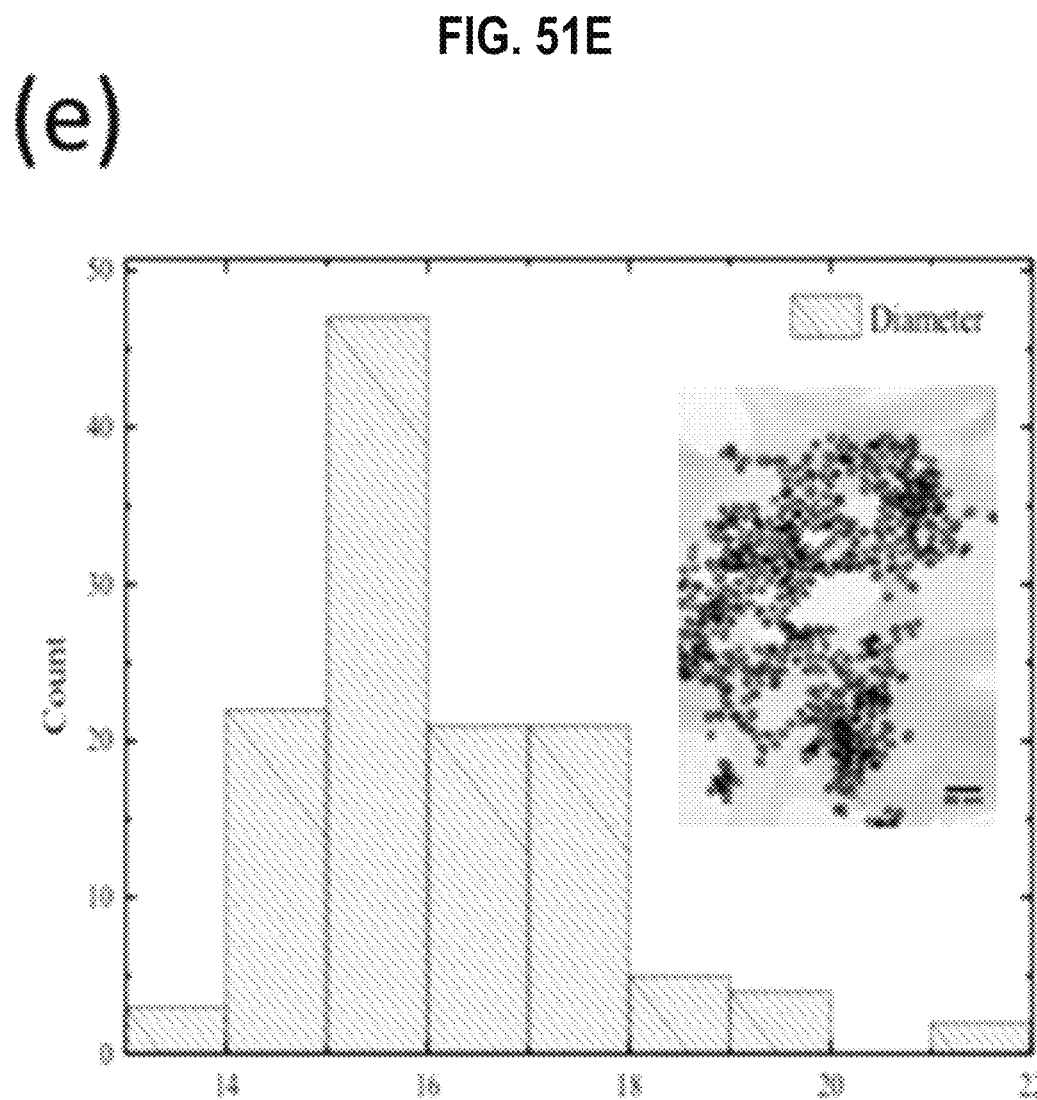
FIG. 51-B is a diagram of Silicon IDE chip after microfabrication. Oxygen plasma removes the silicon oxide layer and it is replaced with hydroxy groups.
Figure 51F:
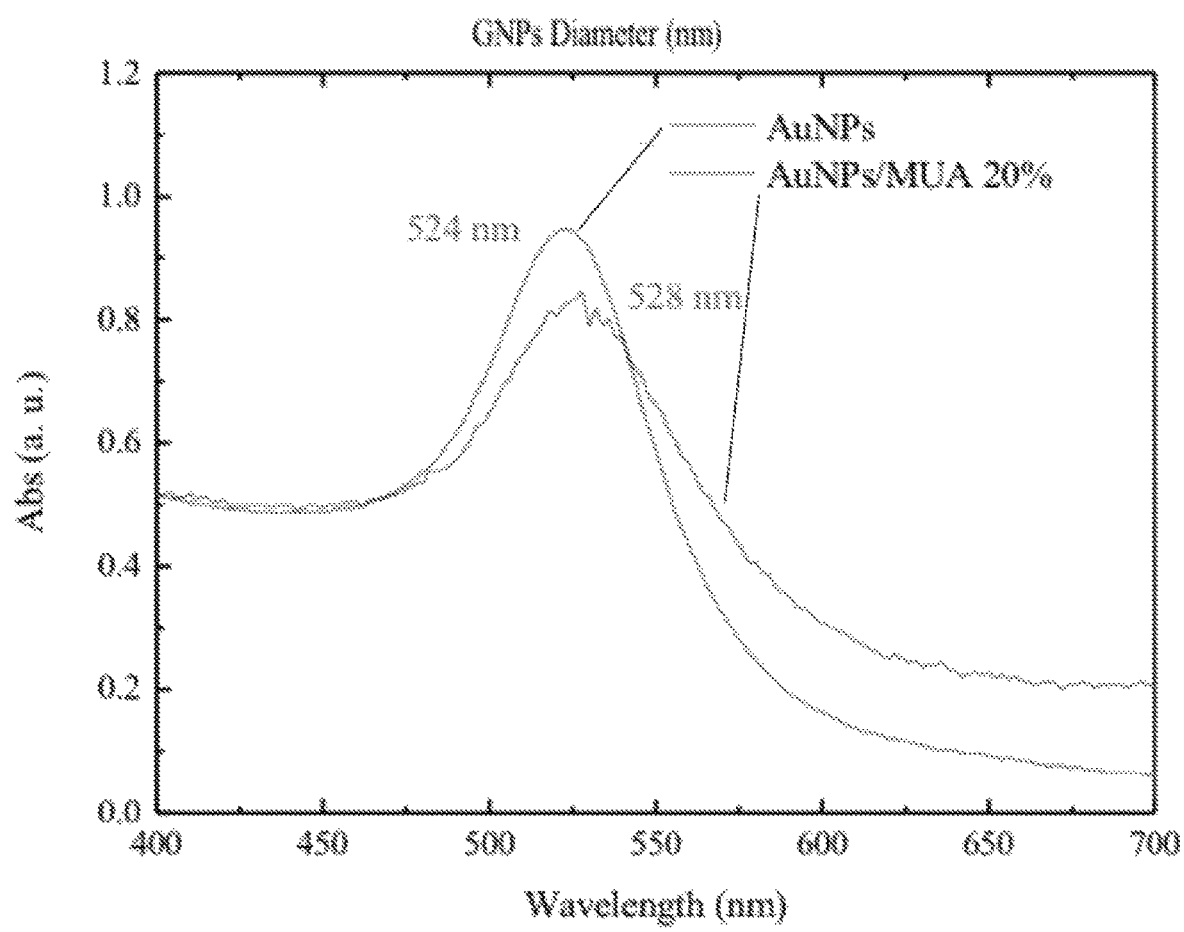

Gold Nanoparticles Synthesis and Surface Modification:

The GNPs prepared by Turkevich-Frens method (33) showed monodispersion with average diameter of 16±2 nm as estimated from measuring the diameter of 125 nanoparticles (refer to the insert of FIG. 51E). The UV-Vis absorption of the GNPs exhibited a typical plasmonic absorption with maximum at 524 nm (refer to FIG. 51F). (34) This maximum was red shifted to 528 nm with modifying the NPs surface by MUA and mPEG-SH indicating the efficient surface coating. The surface coating of the GNPs was further confirmed using DLS and ζ-potential measurements. After coating the GNPs with MUA and mPEG-SH, the hydrodynamic size decreased from 110±15 nm to 55±5 nm, and the ζ-potential decreased from −23 mV to −15 mV. The alteration in the hydrodynamic size might be attributed to the nature of the interaction of the surface modifier with the surround monolayer of the solvent. However, the decrease in the NPs surface charge might be due to the attachment of the mPEG-SH molecules to the surface of the NPs. The use of mPEG-SH was found enhancing the dispersion stability of the GNPs in aqueous medium after surface modification. This is due to the hydrophilic nature of mPEG-SH.

The hydrodynamic size of the nanoparticles represents not only the size of the nanoparticles with the coating layer but also the interfacial zone consists of the first adjacent layers of the solvent surrounding the nanoparticle itself. This interfacial zone is defined by the nature and capacity of the coating molecular layer to interact with the surrounding solvent molecules, which in turn depends on the functional groups anchored to the coating molecules. In the case of MUA, there is only one carboxylic group attached by an aliphatic chain of eleven carbon atoms to the surface of GNPs. The interaction of the surrounding solvent molecules with the GNPs occurred through only one carboxylic group. On the other hand, the sodium citrate surfactant molecule has three carboxylic groups and one hydroxyl group. One of these carboxylic groups attaches directly to the nanoparticle surface, increasing its dispersion stability, while the rest are interacting with the surrounding solvent molecules through hydrogen bonding. This could increase the number of water molecules attracted the GNPs, and consequently, increases the hydrodynamic size.

Effect of Oxygen Plasma on Electrodes and Impedance Measurements:

From Tables 2A and 3A, we can clearly see a lower average impedance in all oxygen plasma results. The change in the surface chemistry due to oxygen plasma cleaning is also noticed in the lower coefficient of variation across all frequencies. The oxygen plasma cleaning (refer to FIGS. 51A-51D) was used to clean the surface of the electrode and activate the silicon dioxide substrate for coating with APTES by initiating hydroxyl groups. The hydroxyl groups affected the average impedance of the IDE.

TABLE 2A

The Average Impedance Magnitude of the Baseline Test of Four Different Wells at Three Different Frequencies

| Baseline Tests | Average Impedance Magnitude (Ohms) | Standard Deviation (Ohms) | Coefficient of Variation |
|---|---|---|---|
| 10 kHz | 869.5 | 143.9 | 0.165 |
| 100 kHz | 601.5 | 59.5 | 0.0989 |
| 1 MHz | 194.2 | 30.8 | 0.159 |

TABLE 3A

The Average Impedance Magnitude of the Impedance Test After Exposing The Chip to Oxygen Plasma.

| Baseline Tests | Average Impedance Magnitude (Ohms) | Standard Deviation (Ohms) | Coefficient of Variation |
|---|---|---|---|
| 10 kHz | 735.9 | 103.9 | 0.141 |
| 100 kHz | 562.6 | 53.7 | 0.0954 |
| 1 MHz | 156.2 | 8.38 | 0.0536 |

Impedance Measurements of GNPs on Gold and Aluminum IDEs:

Surface modification clearly has an effect on the impedance from FIGS. 52A-52F. Modification with GNPs created an increase in impedance due to double layer capacitance. The surface bound GNPs act as capacitors because they form a double layer around their surface. (35) This increase in capacitive character of the chip is noticed in the decrease in the phase of the graph. The greatest change in impedance can be found near 100 kHz. In regards to detecting changes in the surface modification, the middle frequency range is ideal. This is because lower frequencies can be more prone to changes in the variation between measurements. At high frequencies, all measurements appear to converge no matter the type or amount of surface modification. The APTES serves as a binding site for the GNPs. Concentrations of the APTES solutions were varied between wells as percentages of the stock solution in order to understand the effects of surface coverage on impedance. Theoretically we should see an increasing trend in FIG. 52C. This is because the more APTES that is added to the chip, the more binding sites available to the GNPs. This in turn, leads to more GNPs on the surface which can create a larger change impedance. Instead, from our experimental results, we see increases from 2% to 5% and 7% to 10% APTES concentration, with a sharp drop between 5% to 7%. The sharp drop is likely due to an oversaturation of APTES between the electrodes.

Figure 52A:
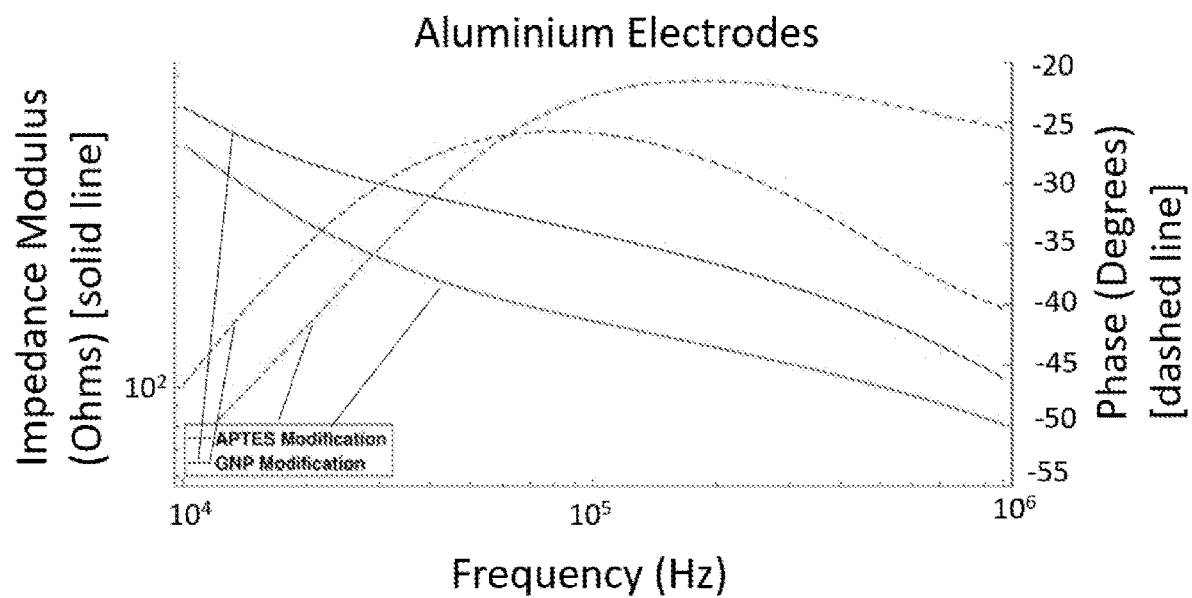
FIG. 52-A is a Bode graph of the impedance measurement after APTES and after GNP modification on a gold IDE.
Figure 52B:
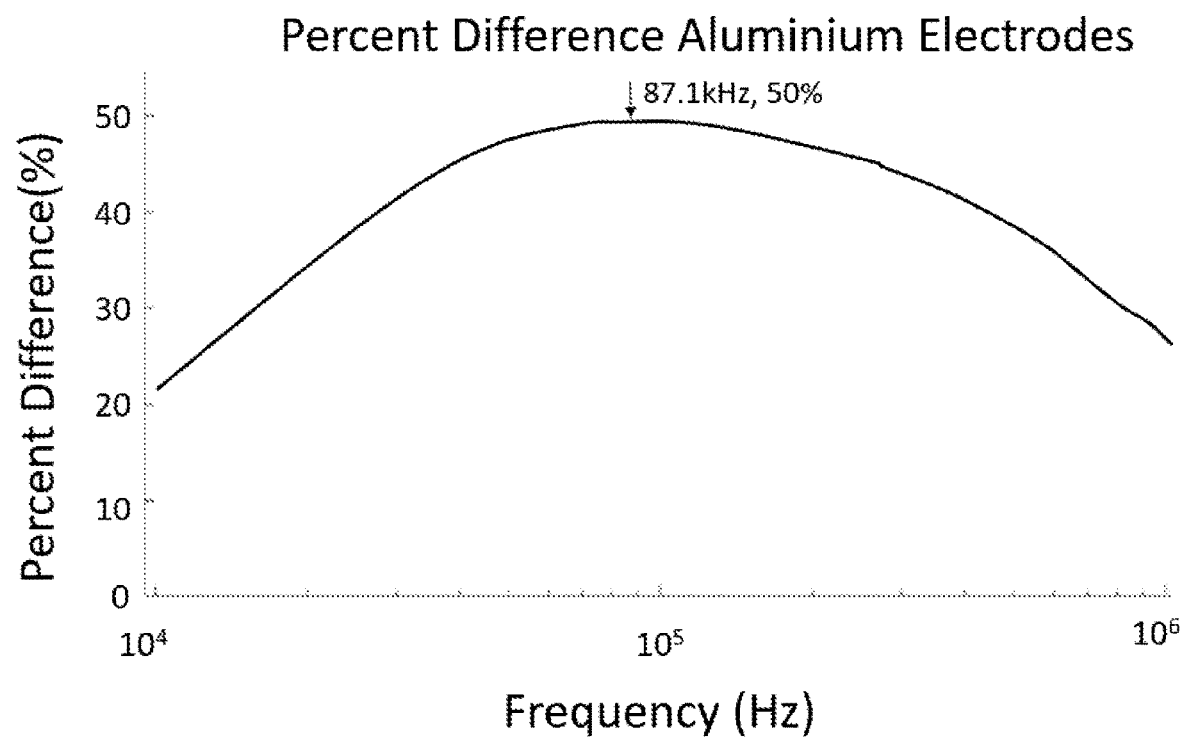
Figure 52C:
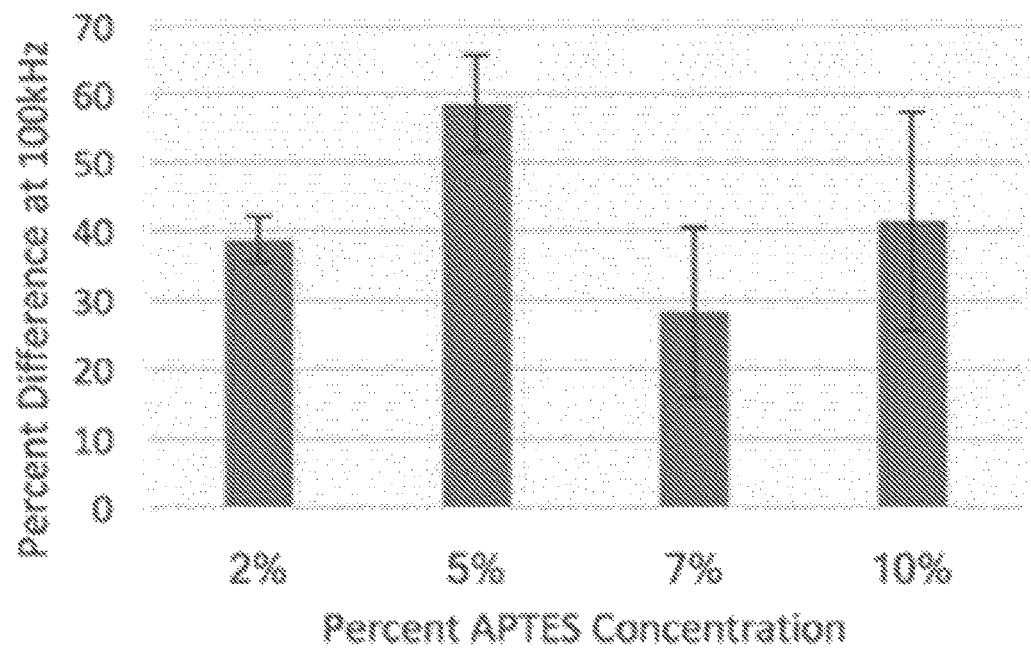
Figure 52D:
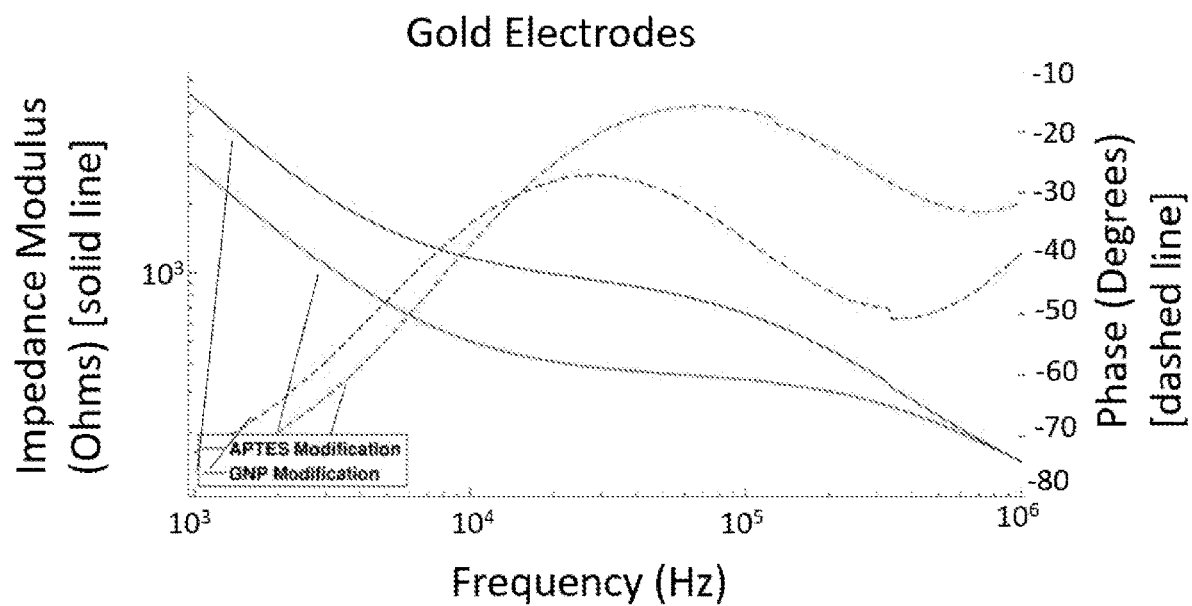

The error bars in FIG. 52C come from the standard deviation of multiple tests taken with the same APTES concentrations. Error between results could be due to a number of factors. Electrode chips were manufactured using wet etching techniques that can have errors in fabrication. All microfabrication techniques have some error associated with the area of fabrication. This causes different chips to have slightly different dimensions, in different areas of the chip.

Compared to simulation results of a virtual chip with the same dimensions and electrode material, an increase due to the surface modification with GNPs matches our experimental results. (16) Simulation results also predicted a peak percent change at a specific frequency, which we see in FIG. 52B. It is important to recognize that compared to some electrochemical impedance spectroscopy designs, our impedance measurements take place after surface modification, not during a reduction-oxidation reaction between a molecule and the surfactant[6]. This allows for the optimization of adsorption of GNPs or other biological molecules to the surface to improve precision and accuracy.

Impedance Measurements of GNPs on Gold IDEs:

In experimentation, a larger frequency range of the gold electrodes was taken, to encompass the graph shape. This allows us to compare the shapes of the graphs more easily. The fact that we need to do this suggest the impedance of the gold electrodes are more resilient to changes in the frequency. Since the impedance of a capacitor is related to the frequency and the impedance of a resistor is not, it suggests that the gold is more resistive than their aluminum counterparts. The addition of GNPs to the surface leads to a higher impedance and increases the capacitive character of the chip. We can tell the chip is more capacitive from the decrease in phase. Comparing FIGS. 52A and 52D note that aluminum and gold have very similar shapes and trends, despite the difference in their IDE materials. Simulations predicted that the differences between gold and aluminum electrodes would not be great. (16) However, there was a difference in how closely the change in impedance correlated with the APTES concentration. For gold electrodes, the graph of percent difference versus APTES concentration has again shown the more GNPs the greater the change in impedance. This trend could allow for the construction of a concentration curve, which could be used to predict the concentration of GNPs added to the surface.

The error in the impedance tests of gold electrode chips is in general higher than the error for the aluminum electrode chips. As previously mentioned, microfabrication can yield chips with slightly different dimensions. Gold is more difficult to work with in regards to microfabrication, because of its natural chemical stability. The chemicals required to etch gold tend to be corrosive enough to destroy other structures on the chip that should be kept fixed. Inevitably, gold electrode chips are slightly over-etched, leading to more spacing between the electrodes.

Characterizing the Distribution of GNPs on IDEs:

The parabolic shape shown in FIG. 52B allows us to easily optimize the frequency that we measure. The average maximum frequency from our results is around 85.7 kHz. This contrasts with simulation predictions, where the peak frequency was on the order of 30 kHz. (16) Optimization of the frequency is important as it could lead to higher sensitivity. This peak frequency could shift depending on how GNPs are bound to the surface. Therefore, the peak frequency could depend on the target biomolecule of interest. There is a correlation between APTES concentration and impedance change. This is because when the APTES concentration is changed in solution, it changes the surface coverage of the binding sites available for GNP binding. This directly affects how many GNPs can bind to the surface, and thus we can see the effect the amount of GNPs has on the surface of the chip. To validate this finding, atomic force microscopy (AFM) was also used to check the distribution of GNPs on the surface of the sensor chip.

Figure 52E:
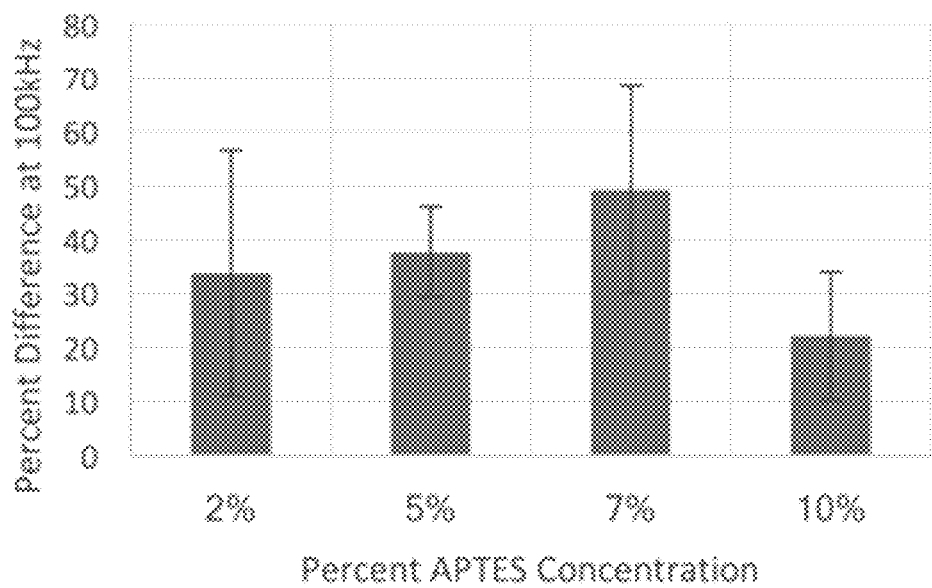
Figure 52F:
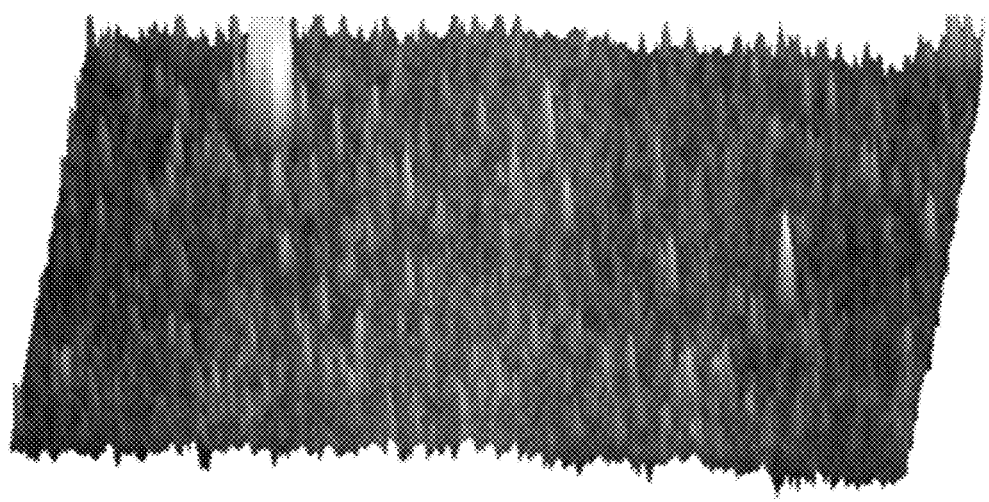

Based on FIG. 52F, we can clearly see the GNPs are on the surface as the validation of our impedance results. With the exception of the large pillar of GNPs at the top left of FIG. 52F, the distribution of GNPs is very uniform with no localized pitting. The clumping of GNPs on the electrodes is something that should be avoided, as it can sometimes create unpredicted impedance results.

Figure 53A:
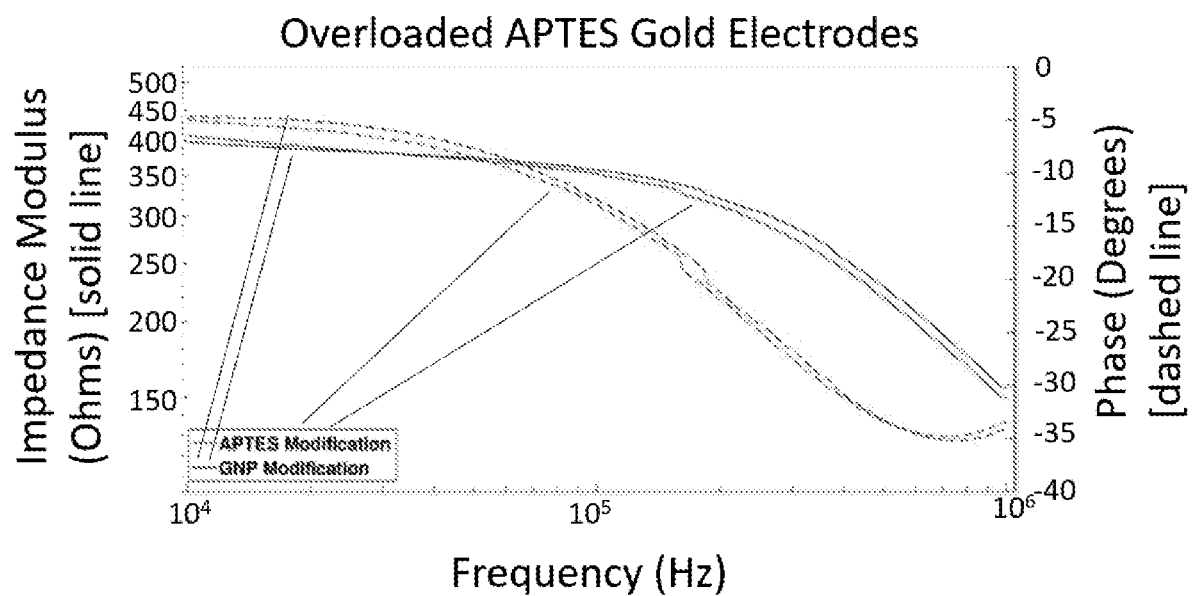
FIG. 53-A is a graph of impedance measurement for a GNP test with a higher concentration of APTES.
Figure 53B:
Figure 53C:
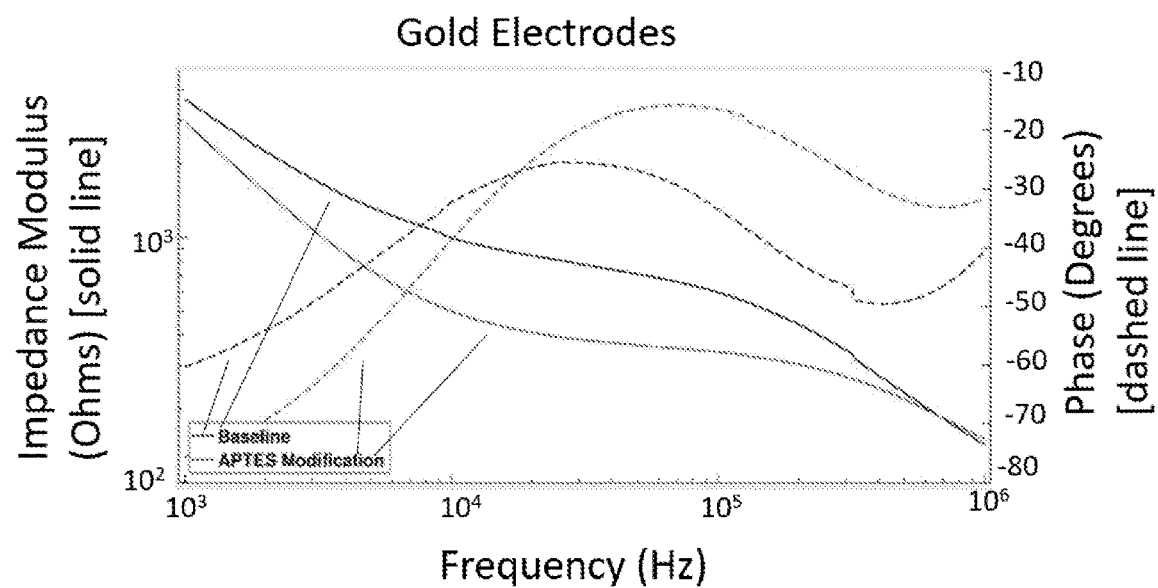

Oversaturation of APTES:

Oversaturation of APTES on the surface can interfere with GNP binding. FIGS. 53A-53E show the effects of higher concentrations of APTES being added to the surface. Based on the impedance measurement graph, there is little to no change from the GNP modification, and the graph has a very different shape in both the phase and the magnitude. From this graph, it indicates that the chip is short-circuited because of APTES accumulated between IDEs, showing a low impedance and near zero phase. FIG. 53B visibly shows the higher APTES concentrations forming three-dimensional complexes, rather than a uniform surface coverage. (36) GNP binding likely did not occur because the upper layers of APTES blocked the binding sites, which is supported from the diminutive change in the impedance measurement graph. From FIG. 53C the decrease in impedance magnitude after a typical APTES surface modification suggests that APTES has some semiconductor properties when adsorbed onto a surface. The addition of APTES to the surface of the electrode leads to a lower impedance in the gold IDEs as well as the aluminum IDEs. This decrease occurs over all frequencies, but tends to affect the middle frequencies more heavily than the extremes. This again validates the theory that changes in surface coating is not the dominant factor of the impedance at extreme frequencies.

In FIGS. 52C and 52E it is shown that there is a sharp drop at higher concentrations of APTES. Oversaturation is a likely cause of this for a several reasons. FIG. 53A shows an extreme case of oversaturation of APTES causing a lower change in impedance between APTES and GNP modification, which matches FIGS. 52C and 52E. Aluminum electrode chip results showed a much larger error in the average percent difference at higher APTES concentrations. The formation of 3-D layers over a surface is not particularly well-defined, as there are many different geometries possible. It is plausible that different geometries would give different impedance magnitudes as more or less binding sites are covered with APTES. This would make the changes in impedance less predictable, however some binding sites would still remain open allowing for an overall increase in impedance change. The oversaturation effect made itself more apparent at a higher APTES concentration in aluminum than the in gold. The gold electrodes are, in general, more over-etched, so there is more space between the electrodes. This means it can hold more APTES on its surface before becoming oversaturated, which is shown in our aluminum versus gold results.

The oversaturation of APTES gives unpredictability and a lower detectable change. Thus, it is important that the silicon substrate is not oversaturated with APTES. It is for this reason that 7% concentration was chosen as our maximum usable concentration for gold electrodes. While higher concentrations of APTES surface coverage could theoretically yield higher changes in impedance magnitude, they also carry more risk of short-circuiting and three-dimensional complexes on the surface.

Effect of Clumped GNPs and MUA Surface Modification:

GNPs have a tendency to aggregate. The theory behind this phenomenon is well-characterized. (37, 38) Many groups use this as a method of detection, especially optical methods. (39-41) However, for the purposes of this design, aggregation is a source of error, since it can cause non-uniform binding on the surface. These results are particularly interesting as simulations did not consider the effects of this phenomenon on the impedance and sensitivity of our sensor. Simulations always assumed a uniform coverage of 10% GNPs, with 30 nm diameter. (16) However, GNP diameters naturally vary through random error and aggregation, which has a significant effect on its capacitance. (35)

Figure 53D:
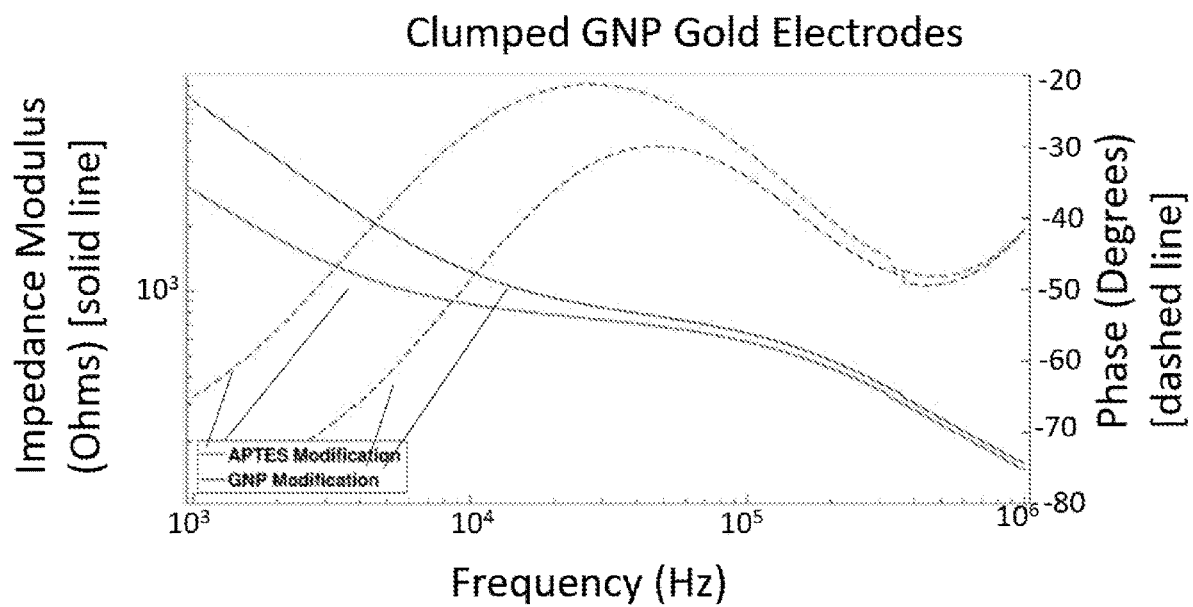
Figure 53E:
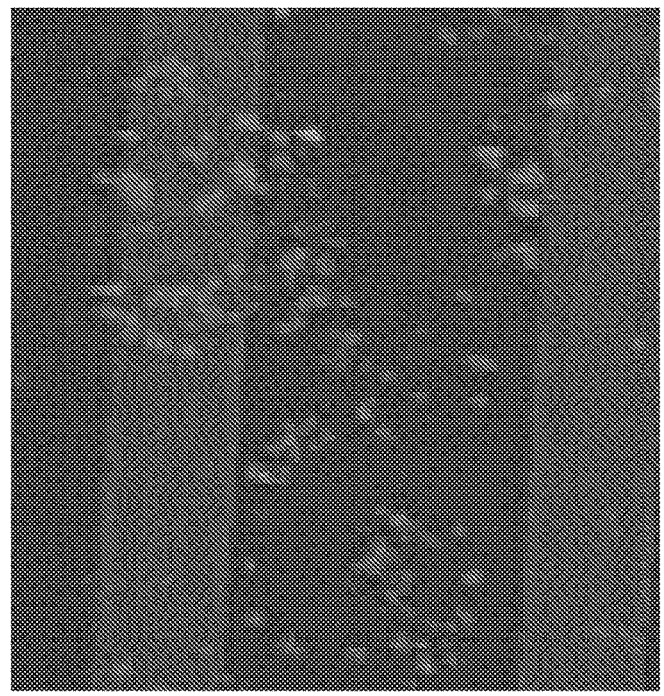

According to the impedance measurement graph in FIG. 53D for a chip with large amounts of GNP aggregation, the maximum change from APTES modification to GNP modification is at a much lower frequency than with the previous results with more uniform GNP distribution (FIGS. 52A-52F). The GNP modification still always increases the impedance. A decreasing phase is typical, however, its shift to the right is inconsistent with other GNP modification tests. The decrease is still likely due to the double layer capacitance of the GNPs. Note that there is very little change at the middle and higher frequencies. Non-uniform surface modification can cause more variation in impedance between tests. From the FIG. 53E, it can be seen that many GNPs aggregated near the electrodes. In these tests, gold IDEs were used, suggesting the possibility that metallic bonding between the two gold substances was affecting results.

Figure 54A:
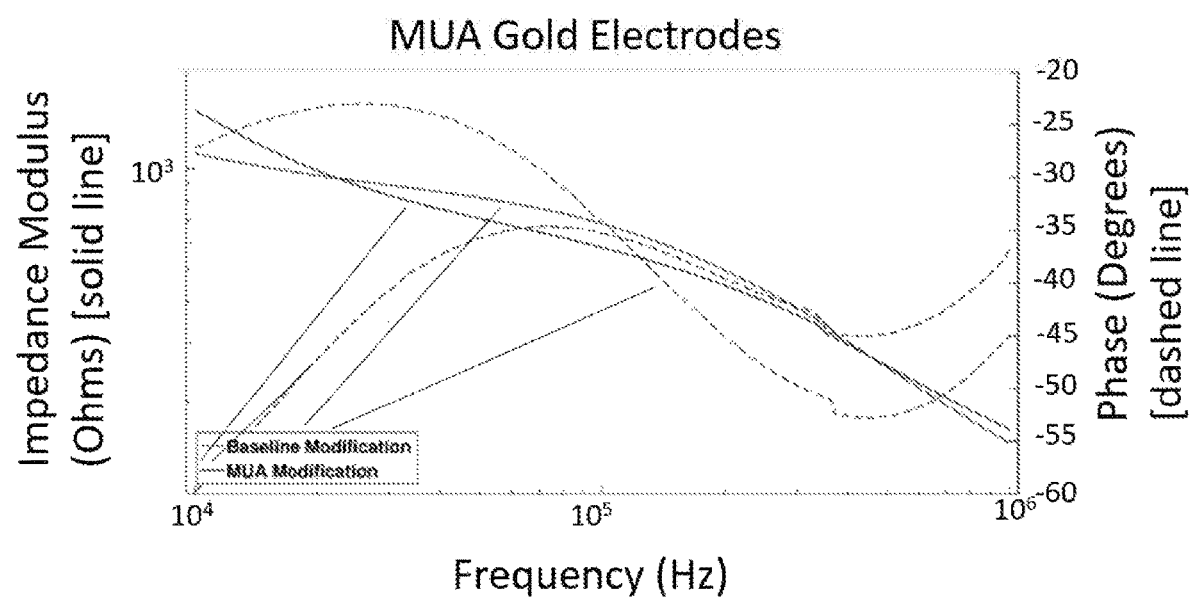
FIG. 54-A is a plot comparing the baseline measurement, with no modification and the measurement taken after the electrodes were modified with MUA.
Figure 54B:
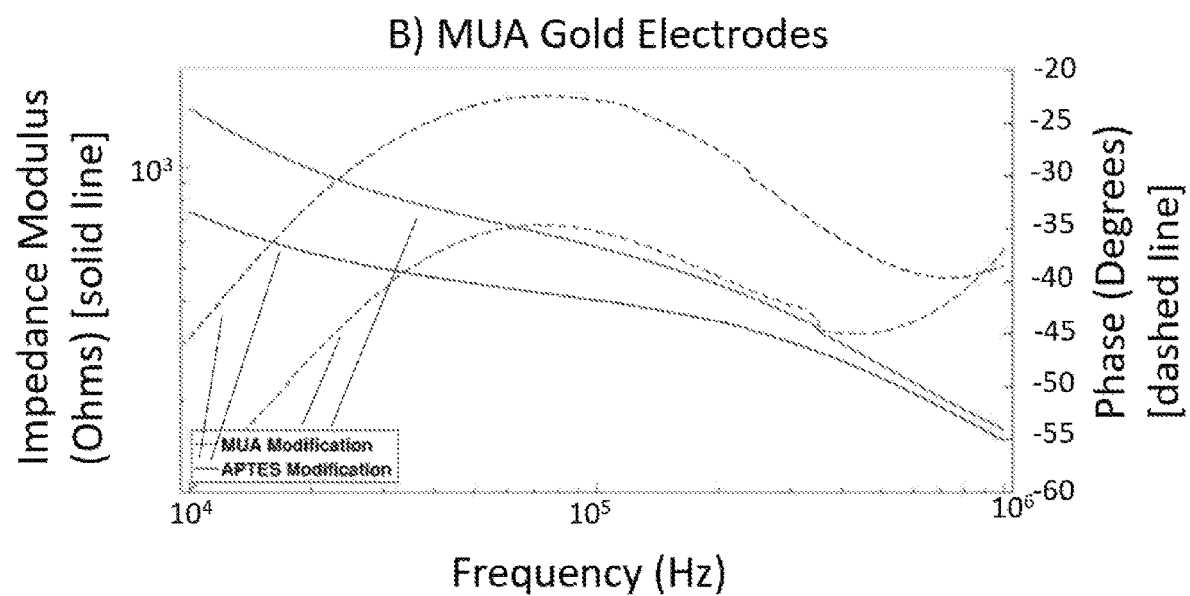
Figure 54C:
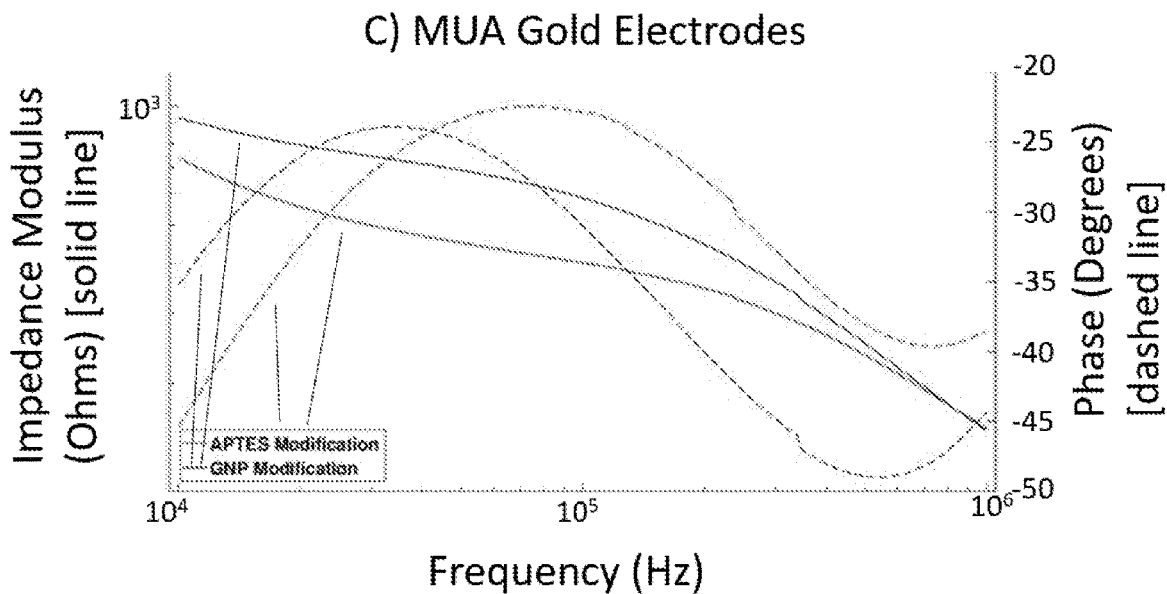
Figure 54D:
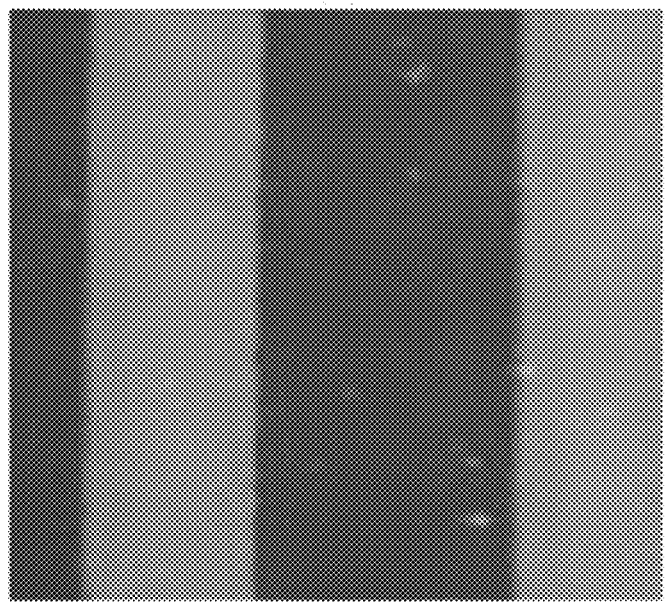

In an attempt to prevent clumping of GNPs on the electrodes, the possibility of a self-assembled monolayer was explored as data has shown that they can reduce corrosion. (24) We can see from FIG. 54A that the addition of an extra layer over the gold IDEs leads to little to no change in the impedance magnitude. This is ideal, since a massive change in impedance magnitude from MUA could overshadow changes in GNP concentration. The capacitive effect of the layer, however, is noticeable, as we can clearly see the downward shift in the phase component of the impedance. Lack of interference between the electrode surface modification and the substrate modification is vital to produce similar results as we have seen with unmodified electrodes. From the impedance results, electrode modification does not appear to interrupt the effects of the spacing modification as indicated in FIGS. 54B and 54C. This graph matches the patterns of the graphs that were previously shown in the aluminum and gold results, where impedance magnitude increased between APTES and GNP measurements. The decrease in impedance after APTES modification also follows the trend shown in FIG. 54C. However, perhaps most importantly, this limited the clumping of GNPs on the IDEs (refer to FIG. 54D.

Discussions

We have characterized many surface modifications of our IDE chip design using both impedance measurement and an AFM. Electrode material, electrode modification, and substrate modification were all investigated. Impedance results showed that surface modification with APTES generally lowered the impedance magnitude over all frequencies. The adsorption of GNPs to the APTES binding sites increased the impedance through double layer capacitance. Tests were performed that show we can detect changes in concentration using GNPs. We found that aluminum IDEs acted similar to gold IDEs in impedance tests. They produced similar trends under the same surface modifications in comparison with themselves and simulation tests. While aluminum is both easier and cheaper to microfabricate electrode chips, gold has been shown to be more chemically stable, and will not interfere with many biological molecules. (42, 43) It is also important to recognize that the electrode material can be changed based on the biological molecule being detected. This allows for greater adaptability and more opportunities in types of molecules that can be detected. Changes in substrate modification yielded consistent impedance changes, which allows for precise determination of changes in concentrations.

Possible sources of errors, such as oversaturation of APTES and GNP clumping were considered, and possible solutions were proposed. Errors in impedance results at each modification step showed how increased modification stabilized measurements. Optimization of the ideal frequency of a single impedance measurement for greatest sensitivity was explored and we found this frequency to be 85.7 kHz. AFM imaging revealed GNP aggregation appeared to occur more prominently near gold electrodes, likely due to the metallic bonding attraction between themselves.

The effects of modifying the surfaces of interdigitated electrodes in conjunction with the modified silicon substrate with the intent of preventing the aggregation of GNPs on the surface of the electrodes was explored. The electrical character of the chip surface becomes more capacitive as gold nanoparticles are bound between electrode digits. Aggregation of GNPs on the surfaces of the electrodes was shown to decrease compared to chips not modified with MUA. MUA was chosen to construct the self-assembled monolayer, while many other molecules have been shown to bind to gold, (44) their differing effects on impedance measurements requires further investigation. The electrode surfaces were modified only with single strands of MUA. Self-assembled monolayers can be polymerized, (25, 45) and the effects of such polymerization on impedance requires further research.

The ultimate goal is to use this biosensor to measure the presence and concentration of biological molecules, such as DNA, proteins, or metabolites. A sandwich assay can be used to attach GNPs to the surface; this can easily be modified to any available aptamers to detect any number of biological molecules. The only limitation on what can be detected is based on the availability and existence of aptamers for any given molecule. Due to the physical size of the chip and the microfabricated design, portability of the sensor is extremely feasible. Biological samples can be difficult to obtain and often can only in very small volumes. Our chip only required the addition of 50 μL solutions to the wells of the electrodes, allowing for opportunities to test very small bio-samples accurately. Due to the overall simplicity in design and miniaturization, costs of producing chips are relatively inexpensive compared to some other methods. Impedance tests can very easily be automated and programmed to work, allowing for users inexperienced with electrical circuitry to use this device such as nurses and doctors. This characteristic is vital for a point-of-care design. These characteristics of the chip allow for high versatility, for an inexpensive, portable, point-of-care biosensor device.

Conclusion

In this article, we discussed the techniques used to bind gold nanoparticles (GNPs) on interdigitated electrodes (IDEs), and the characterization and detection of the surface modifications as well. Both measurement results and simulation results suggested that we can use impedance measurements to characterize surface modified with gold nanoparticles. Such an impedance-based design make a versatile handheld, inexpensive biosensor device feasible.

References

1. R. Etzioni, N. Urban, S. Ramsey, M. McIntosh, S. Schwartz, B. Reid, J. Radich, G. Anderson, L. Hartwell, The case for early detection. *Nat. Rev. Cancer.* 3, 243-252 (2003).
2. K. C. Cary, M. R. Cooperberg, Biomarkers in prostate cancer surveillance and screening: past, present, and future, 318-329 (2013).
3. I. R. Lauks, Microfabricated Biosensors and Microanalytical Systems for Blood Analysis. *Acc. Chem. Res.* 31, 317-324 (1998).
4. M. Mascini, S. Tombelli, Biosensors for biomarkers in medical diagnostics. *Biomarkers.* 13, 637-657 (2008).
5. J. S. Lee, C. A. Mirkin, Chip-based scanometric detection of mercuric ion using DNA-functionalized gold nanoparticles. *Anal. Chem.* 80, 6805-6808 (2008).
6. J. S. Lee, P. A. Ulmann, M. S. Han, C. A. Mirkin, A DNA—Gold nanoparticle-based colorimetric competition assay for the detection of cysteine. *Nano Lett* 8, 529-533 (2008).
7. B. Mehta, Z. Li, M. Zaghloul, "Optical Bio Sensor Using Graphene Nano Ribbons," paper presented at Semiconductor Device Research Symposium (ISDRS), College Park, Md., USA 7-9 of Dec. 2011. Army Research Laboratory, Electrical and Computer Engineering Department of the University of Maryland, Electron Devices Society, Institute of Electrical and Electronic Engineers Inc., National Institute of Standards and Technology, National Science Foundation, The Maryland Nanocenter of the University of Maryland.
8. M. C. Rodriguez, A.-N. Kawde, J. Wang, Aptamer biosensor for label-free impedance spectroscopy detection of proteins based on recognition-induced switching of the surface charge. *Chem. Commun. (Camb).*, 4267-4269 (2005).
9. X. Chen, Z. Guo, G. Yang, J. Li, M. Li, J. Liu, X. Huang, Electrical nanogap devices for biosensing For detecting substances that are invisible to the human eye or nose, *Mater. Today.* 13, 28-41 (2010).
10. M. Su, S. Li, V. P. Dravida, Microcantilever resonance-based DNA detection with nanoparticle probes. *Appl. Phys. Lett.* 82, 3562-3564 (2003).
11. A. M. Moulin, S. J. O'Shea, M. E. Welland, Microcantilever-based biosensors. *Ultramicroscopy.* 82, 23-31 (2000).
12. J. L. Arlett, E. B. Myers, M. L. Roukes, Comparative advantages of mechanical biosensors. *Nat. Publ. Gr.* 6, 203-215 (2011).
13. V. S.-Y. Lin, K. Motesharei, K.-P. S. Dancil, M. J. Sailor, M. R. Ghadiri, A Porous Silicon-Based Optical Interferometric Biosensor. *Science (80-.).* 278, 840-843 (1997).
14. R. Raiteri, M. Grattarola, H. J. Butt, P. Skládal, Micromechanical cantilever-based biosensors. *Sensors Actuators, B Chem.* 79, 115-126 (2001).
15. P. Baptista, E. Pereira, P. Eaton, G. Doria, A. Miranda, I. Gomes, P. Quaresma, R. Franco, Gold nanoparticles for the development of clinical diagnosis methods. *Anal. Bioanal. Chem.* 391, 943-950 (2008).
16. P. Hermansen, S. Mackay, D. Wishart, J. Chen, "Simulations and Design of Microfabricated Interdigitated Electrodes for Use in a Gold Nanoparticle Enhanced Biosensor," paper presented at 38th Annual International Conference of the IEEE Engineering in Medicine and Biology Society (EMBC), Orlando, Fla., USA 16-20 Aug. 2016.
17. D. Grieshaber, R. MacKenzie, J. Vörös, E. Reimhult, Electrochemical Biosensors—Sensor Principles and Architectures. *Sensors.* 8, 1400-1458 (2008).
18. R. K. DeLong, C. M. Reynolds, Y. Malcolm, A. Schaeffer, T. Severs, A. Wanekaya, Functionalized gold nanoparticles for the binding, stabilization, and delivery of therapeutic DNA, RNA, and other biological macromolecules. *Nanotechnol. Sci. Appl.* 3, 53-63 (2010).
19. O. V Salata, Applications of nanoparticles in biology and medicine. *J. Nanobiotechnology.* 6, 1-6 (2004).

20. C. C. Huang, Y. F. Huang, Z. Cao, W. Tan, H. T. Chang, Aptamer-modified gold nanoparticles for colorimetric determination of platelet-derived growth factors and their receptors. *Anal Chem.* 77, 5735-5741 (2005).
21. S. Mackay, D. Wishart, J. Z. Xing, J. Chen, Developing trends in aptamer-based biosensor devices and their applications. *IEEE Trans. Biomed. Circuits Syst.* 8, 4-14 (2014).
22. P. Van Gerwen, W. Laureys, G. Huyberechts, M. De Baeck, K. Baert, J. Suis, A. Varlan, W. Sansen, L. Hermans, R. Mertens, Nanoscaled interdigitated electrode arrays for biochemical sensors. *Sensors Actuators B Chem.* 49, 73-80 (1998).
23. F. Cecchet, M. Marcaccio, M. Margotti, F. Paolucci, S. Rapino, P. Rudolf, Redox mediation at 11-mercaptoundecanoic acid self-assembled monolayers on gold. *J. Phys. Chem. B.* 110, 2241-2248 (2006).
24. F. P. Zamborini, R. M. Crooks, Corrosion Passivation of Gold by n-Alkanethiol Self-Assembled Monolayers: Effect of Chain Length and End Group. *Langmuir.* 14, 3279-3286 (1998).
25. T. Kim, Q. Ye, L. Sun, K. C. Chan, R. M. Crooks, Polymeric self-assembled monolayers 0.5. Synthesis and characterization of omega-functionalized, self-assembled diacetylenic and polydiacetylenic monolayers. *Langmuir.* 12, 6065-6073 (1996).
26. C. E. Jordan, a G. Frutos, a J. Thiel, R. M. Corn, Surface plasmon resonance imaging measurements of DNA hybridization adsorption and streptavidin/DNA multilayer formation at chemically modified gold surfaces. *Anal. Chem.* 69, 4939-4947 (1997).
27. Y. Song, Z. Li, Z. Liu, G. Wei, L. Wang, L. Sun, Immobilization of DNA on 11-mercaptoundecanoic acid-modified gold (111) surface for atomic force microscopy imaging. *Microsc. Res. Tech.* 68, 59-64 (2005).
28. M. D. Porter, T. B. Bright, D. L. Allara, C. E. D. Chidsey, Spontaneously Organized Molecular Assemblies. 4. Structural Characterization of n-Alkyl Thiol Monolayers on Gold by Optical Ellipsometry, Infrared Spetcroscopy, and Electrochemistry. *J. Am. Chem. Soc.* 109, 3559-3568 (1987).
29. S. MacKay, P. Hermansen, D. Wishart, J. Chen, Simulations of interdigitated electrode interactions with gold nanoparticles for impedance-based biosensing applications. *Sensors (Switzerland).* 15, 22192-22208 (2015).
30. G. N. Abdelrasoul, B. Farkas, I. Romano, A. Diaspro, S. Beke, Nanocomposite scaffold fabrication by incorporating gold nanoparticles into biodegradable polymer matrix: Synthesis, characterization, and photothermal effect. *Mater. Sci. Eng. C.* 56, 305-310 (2015).
31. D. Lin, T. Tang, D. Jed Harrison, W. E. Lee, A. B. Jemere, A regenerating ultrasensitive electrochemical impedance immunosensor for the detection of adenovirus. *Biosens. Bioelectron.* 68, 129-134 (2015).
32. J. C. Love, L. A. Estroff, J. K. Kriebel, R. G. Nuzzo, G. M. Whitesides, Self-assembled monolayers of thiolates on metals as a form of nanotechnology. *Chem. Rev.* 105, 1103-1169 (2005).
33. J. Turkevich, P. C. Stevenson, J. Hillier, A Study of the Nucleation and Growth Processes in the Synthesis of Colloidal Gold. *Discuss. Faraday,* 55-75 (1949).
34. J. Kimling, M. Maier, B. Okenve, V. Kotaidis, H. Ballot, A. Plech, Turkevich Method for Gold Nanoparticle Synthesis Revisited.pdf. *J. Phys. Chem. B.* 110, 15700-15707 (2006).
35. S. Chen, R. W. Murray, S. W. Feldberg, Quantized Capacitance Charging of Monolayer-Protected Au Clusters. *J. Phys. Chem. B.* 102, 9898-9907 (1998).
36. A. A. Golub, A. I. Zubenko, B. V. Zhmud, γ-APTES Modified Silica Gels: The Structure of the Surface Layer. *J. Colloid Interface Sci.* 179, 482-487 (1996).
37. T. Kim, C. H. Lee, S. W. Joo, K. Lee, Kinetics of gold nanoparticle aggregation: Experiments and modeling. *J. Colloid Interface Sci.* 318, 238-243 (2008).
38. S. K. Ghosh, T. Pal, Interparticle Coupling Effect on the Surface Plasmon Resonance of Gold Nanoparticles: From Theory to Applications. *Chem. Rev.* 107, 4797-4862 (2007).
39. R. Elghanian, J. J. Storhoff, R. C. Mucic, R. L. Letsinger, C. A. Mirkin, Selective Colorimetric Detection of Polynucleotides Based on the Distance-Dependent Optical Properties of Gold Nanoparticles. *Science (80-.).* 277, 1078-1080 (1997).
40. W. Zhao, W. Chiuman, M. A. Brook, Y. Li, Simple and rapid colorimetric biosensors based on DNA aptamer and noncrosslinking gold nanoparticle aggregation. *ChemBioChem.* 8, 727-731 (2007).
41. H. Li, L. Rothberg, Colorimetric detection of DNA sequences based on electrostatic interactions with unmodified gold nanoparticles. *Proc. Natl. Acad. Sci. U.S.A* 101, 14036-9 (2004).
42. R. Shukla, V. Bansal, M. Chaudhary, A. Basu, R. R. Bhonde, M. Sastry, Biocompatibility of gold nanoparticles and their endocytotic fate inside the cellular compartment: A microscopic overview. *Langmuir.* 21, 10644-10654 (2005).
43. A. L. Crumbliss, S. C. Perine, J. Stonehuerner, K. R. Tubergen, J. Zhao, R. W. Henkens, Colloidal gold as a biocompatible immobilization matrix suitable for the fabrication of enzyme electrodes by electrodeposition. *Biotechnol. Bioeng.* 40, 483-490 (1992).
44. C. D. Bain, G. M. Whitesides, Formation of monolayers by the coadsorption of thiols on gold: variation in the head group, tail group, and solvent. *J. Am. Chem. Soc.* 111, 7155-7164 (1989).
45. R. Schmidt, T. Zhao, J.-B. Green, D. J. Dyer, Photoinitiated Polymerization of Styrene from Self-Assembled Monolayers on Gold. *Langmuir.* 18, 1281-1287 (2002).

In the present disclosure, the structure, features, accessories, and alternatives of specific embodiments described herein and shown in the Figures are intended to apply generally to all of the teachings of the present disclosure, including to all of the embodiments described and illustrated herein, insofar as they are compatible. In other words, the structure, features, accessories, and alternatives of a specific embodiment are not intended to be limited to only that specific embodiment unless so indicated.

In addition, the steps and the ordering of the steps of methods described herein are not meant to be limiting. Methods comprising different steps, different number of steps, and/or different ordering of steps are also contemplated.

The above-described embodiments are intended to be examples only. Alterations, modifications and variations can be effected to the particular embodiments by those of skill in the art without departing from the scope, which is defined solely by the claims appended hereto.

What is claimed is:

1. A biosensor chip configured to detect a target biomolecule in a sample, the biosensor chip comprising:

a detection device comprising a substrate, and first and second spaced-apart electrodes disposed at the substrate, with a gap between the electrodes of 1.5 to 5 µm;

a first, molecular recognition element (MRE) bound to the substrate between the first and second electrodes, the MRE being adapted to bind with the target biomolecule; and nanoparticles having a second MRE bound to their surfaces, wherein an electrical impedance across the first and second electrodes changes in response to an immobilization of the nanoparticles between the first and second electrodes due to binding of the target biomolecule with the first MRE and binding of the target biomolecule with the second MRE, and the nanoparticles have a diameter of at most 120 nm.

2. The biosensor chip of claim 1, wherein the first and second electrodes form part of an interdigitated microelectrode array such that the first electrode is formed into an array of first digits and the second electrode is formed into an array of second digits interdigitated with the array of first digits, and wherein the first MRE is bound to the substrate between adjacent digits of the first and second electrodes.

3. The biosensor chip of claim 2, wherein the change in impedance is caused at least in part by a double layer capacitance formed in a solution surrounding the nanoparticles.

4. The biosensor chip of claim 1, wherein the nanoparticles are gold nanoparticles.

5. The biosensor chip of claim 4, wherein the first and second MREs are one of an aptamer, an antibody, a binding protein, an RNA fragment, or a DNA fragment; and
the first and second electrodes comprise at least one of gold or aluminum.

6. The biosensor chip of claim 1, wherein the nanoparticles are coated with mercaptoundecanoic acid (MUA).

7. The biosensor chip of claim 1, wherein the first and second MREs are one of an aptamer, an antibody, a binding protein, an RNA fragment, or a DNA fragment.

8. A biosensor system for detecting a target biomolecule in a sample, comprising:
the biosensor chip of claim 1, and
a biosensor electronic device configured for measuring the impedance across the first and second electrodes of the biosensor chip at one or more frequencies in the range of 50 kHz to 500 kHz.

9. The biosensor system of claim 8, further comprising an electronic display device communicatively coupled to the biosensor electronic device, the display device configured to display information that is responsive to changes in the electrical impedance across the first and second electrodes of the biosensor chip.

10. The biosensor system of claim 9, wherein the biosensor electronic device is configured to detect a change in the electrical impedance across the first and second electrodes using impedance spectroscopy.

11. The biosensor system of claim 9, wherein the information displayed comprises concentration of the target biomolecule in the sample.

12. The biosensor system of claim 8, wherein the biosensor electronic device is configured for measuring the impedance across the first and second electrodes at one or more frequencies, and configured to determine the presence or absence of the target biomolecule in the sample based on the one or more impedance measurements.

13. The biosensor system of claim 8, wherein the biosensor electronic device comprises:
a central processing unit,
memory,
an input/output interface configured to couple to the biosensor chip,
optionally a video adapter, and
optionally a communications subsystem.

14. The biosensor chip of claim 1, wherein the first and second electrodes comprise at least one of gold or aluminum.

15. The biosensor chip of claim 1, wherein the first and second electrodes are modified with a pacifying self-assembled monolayer.

16. The biosensor chip of claim 1, wherein the surface of the substrate has been modified using 3-aminopropyltriethoxy silane (APTES) to activate the substrate towards selective chemical binding with the MRE.

17. A method of detecting a target biomolecule in a sample with the biosensor chip of claim 1, comprising:
exposing the biosensor chip to the sample, to bind the target biomolecule to the first MRE and the second MRE and immobilize the nanoparticles between the first and second electrodes;
measuring the electrical impedance across the first and second electrodes; and
detecting the presence of the target biomolecule in the sample based on the measured electrical impedance.

18. The method of claim 17, wherein the nanoparticles are gold nanoparticles.

19. The method of claim 17, further comprising measuring the impedance across the first and second electrodes at one or more frequencies in the range of 50 kHz to 500 kHz.

20. The method of claim 17, further comprising displaying on an electronic display device information that is responsive to changes in the electrical impedance across the first and second electrodes.

* * * * *